(12) United States Patent
Scheiflinger et al.

(10) Patent No.: US 7,033,590 B1
(45) Date of Patent: Apr. 25, 2006

(54) FACTOR IX/FACTOR IXA ACTIVATING ANTIBODIES AND ANTIBODY DERIVATIVES

(75) Inventors: Friedrich Scheiflinger, Vienna (AT); Randolf Kerschbaumer, Vienna (AT); Falko-Guenter Falkner, Orth/Donau (AT); Friedrich Dorner, Vienna (AT); Hans-Peter Schwarz, Vienna (AT)

(73) Assignee: Baxter Aktiengesellschaft, Vienna (AT)

( * ) Notice: Subject to any disclaimer, the term of this patent is extended or adjusted under 35 U.S.C. 154(b) by 462 days.

(21) Appl. No.: 09/661,992

(22) Filed: Sep. 14, 2000

(30) Foreign Application Priority Data

Sep. 14, 1999 (AT) .............................................. 1576/99

(51) Int. Cl.
*A61K 39/395* (2006.01)
*A61K 38/04* (2006.01)
*C12N 5/20* (2006.01)
*C07K 16/00* (2006.01)
*C07K 16/34* (2006.01)

(52) U.S. Cl. ............... 424/145.1; 435/326; 530/388.25; 530/387.1; 530/327; 530/328; 530/389.3

(58) Field of Classification Search .............. 530/387.3, 530/388.25, 389.3, 327, 328; 424/133.1, 424/145.1; 435/326
See application file for complete search history.

(56) References Cited

U.S. PATENT DOCUMENTS

| 4,395,396 A | 7/1983 | Eibl et al. |
| 4,873,316 A | 10/1989 | Meade et al. |
| 5,932,706 A | 8/1999 | Mertens et al. |
| 6,391,299 B1 * | 5/2002 | Blackburn et al. |
| 6,632,927 B1 * | 10/2003 | Adair et al. |

FOREIGN PATENT DOCUMENTS

| WO | WO95/13300 | 5/1995 |
| WO | WO97/26010 | 7/1997 |
| WO | WO99/01476 | 1/1999 |

OTHER PUBLICATIONS

Panka et al. Variable region framework differences result in decreased or increased affinity of variant anti-digoxin antibodies. Proc Natl Acad Sci U S A. 85(9):3080-3084, 1988.*

Rudikoff et al. Single amino acid substitution altering antigen-binding specificity. Proc Natl Acad Sci U S A. 79(6):1979-1983, 1982.*

Ames, R.S. et al., *Conversion of Murina Fabs Isolated From a Combinatorial Phage Display Library to Full Length Immunoglobulins*, J. Immunol. Methods, pp. 177-186 (1995).

Bajaj, S.P. et al., *A Monoclonal Antibody to Factor IX That Inhibits the Factor VIII:Ca Potentiation of Factor X Activation*, The Journal of Biological Chemistry, 260(21), pp. 11574-11580 (1985).

Bessos, H., et al., *The Characterization of a Panel of Monoclonal Antibodies to Human Coagulation Factor IX*, Thrombosis Research, 40, pp. 863-867 (1985).

Cao, Y. et al., *Bispecific Antibodies as Novel Bioconjugates*, Bioconjugate Chemistry, 9(6); pp. 635-644 (1998).

Cohen, F.E., et al., *The Combinatorial Approach, Protein Structure Prediction—A Practical Approach* (Ed. M.J.E. Sternberg), Oxford University Press, Ch. 9, pp. 207-227 (1996).

Engelhardt, O., et al., *Two Step Cloning of Antibody Variable Domains in a Phage Display Vector*, Biotechniques, 17, p. 44-46 (1994).

Esser, C., et al., *Immunoglobulin Class Switching: Molecular and Cellular Analysis*, Annu. Rev. Immunol., 8, p. 717-735 (1990).

Evan, G.I., et al., *Isolation of Monoclonal Antibodies Specific for Human c–myc Proto–Oncogene Product*, Mol. Cell. Biol., 5(12), p. 3610-3616 (1985).

Fay, P.J., et al., *Factor VIIIa A2 Subunit Residues 558-565 Represent a Factor IXa Interactive Site*, Journal of Biological Chemistry, 269(32), p. 20522-20527 (1994).

Frazier, D., et al., *Mapping of Monoclonal Antibodies to Human Factor IX*, Blood, 74(3), p. 971-977 (1989).

Gao, C., et al., *Making Artifical Antibodies: A Format for Phage Display of Combinatorial Heterodimeric Arrays*, Proc. Natl. Acad. Sci., 96, p. 6025-6030 (1999).

Grassy, G., et al., *Computer–Assisted Rational Design of Immunosuppressive Compounds*, Nature Biotechnology, 16, p. 748-752 (1998).

Greer, J., et al., *Application of the Three–Dimensional Structures of Protein Target Molecules in Structure–Based Drug Design*, Journal of Medicinal Chemistry, 37(8), p. 1035-1054 (1994).

Harlow, E., et al., *2. Antibody Molecules, Antibodies—A Laboratory Manual*; pp. 7-22 (1988).

Harlow, E., et al., *3. Antibody–Antigen Interactions, Antibodies—A Laboratory Manual*; p. 23-35 (1988).

Harlow, E., et al., *6. Monoclonal Antibodies, Antibodies—A Laboratory Manual*; p. 139-243 (1988).

Hochuli, E., et al., *Genetic Approach to Facilitate Purfication of Recombinant Proteins with a Novel Metal Chelate Adsorbent*, Biotechnology, 6, p. 1321-1325 (1988).

Huston, J.S., et al., *Medical Applications of Single–Chain Antibodies*, Intern. Rev. Immunol., 10, p. 195-217 (1993).

(Continued)

*Primary Examiner*—Christina Chan
*Assistant Examiner*—Maher Haddad
(74) *Attorney, Agent, or Firm*—Townsend and Townsend and Crew LLP

(57) ABSTRACT

An antibody or antibody derivative against factor IX/activated factor IX (FIXa) which increases the procoagulant activity of FIXa.

22 Claims, 61 Drawing Sheets

OTHER PUBLICATIONS

Jones, D.T., et al., *Protein Folds and Their Recognition from Sequence, Protein Structure Prediction—A Practive Approach* (Ed. M.J.E. Sternberg), Oxford University Press, Ch. 8, p. 174–206 (1996).

Jones, P.T., et al., *Replacing the Complementarity–Determining Regions in a Human Antibody with Those from a Mouse*, Nature, 321, p. 522–525 (1986).

Jorquera, J.I., et al., *Synthetic Peptides Derived from Residues 698 to 710 of Factor VIII Inhibit Factor IXa Activity*, Circulation, 86, Abstract No. 2725, p. I–685 (1992).

Karpen, M.E., et al., *Modelling Protein Conformation by Molecular Mechanics and Dynamics, Protein Structure Prediction—A Practical Approach* (Ed. M.J.E. Sternberg), Oxford University Press, Ch. 10, p. 229–261 (1996).

Kemp, D.S., *Peptidomimetics and the Template Approach to Nucleation of B–sheets and a–helices in Peptides*, TIBTECH8, p. 249–255 (1990).

Kerschbaumer, R.J., et al, *pDAP2: A Vector for Construction of Alkaline Phosphatase Fusion–Proteins, Immunotechnology*, 2, p. 145–150 (1996).

Kerschbaumer, R.J. et al., *Single–Chain Fv Fusion Proteins Suitables as Coating and Detecting Reagents in a Double Antibody Sandwich Enzyme–Linked Immunosorbent Assay, Analytical Biochemistry*, 249, p. 219–227 (1997).

Lane, R.D., *A Short–Duration Polyethylene Glycol Fusion Technique for Increasing Production of Monoclonal Antibody–Secreting Hybridomas, Journal of Immunological Methods*, 81, p. 223–227 (1985).

Lenting, P.J., et al., *The Sequence $Glu^{1811}$–$Lys^{1818}$ of Human Blood Coagulation Factor VIII Comprises a Binding Site for Activated Factor IX, Journal of Biological Chemistry*, 271(4), p. 1935–1940 (1996).

Liles, D.K., et al, *The Factor VIII Peptide Consisting of Amino Acids 698 to 712 Enhances Factor IXa Cleavage of Factor X, Blood*, 90(1), Abstract No. 2054, p. 463a (1997).

Lin, H–F., et al, *A Coagulation Factor IX–Deficient Mouse Model for Human Hemorphilia B, Blood*, 90(10), p. 3962–3966 (1997).

Malik, P., et al., *Multiple Display of Foreign Peptide Epitopes on Filamentous Bacteriophage Virions, Phage Display of Peptides and Proteins* (Ed. B. K. Kay et al.), Academic Press, p. 127–139 (1996).

Mann, K.G., et al., *Surface–Dependent Reactions of the Vitamin K–Dependent Enzyme Complexes, Blood*, 76(1), p. 1–16 (1990).

Mikaelsson, M., et al., *Standardization of VIII:C Assays: A Manufactorer's View, Scandinavian Journal of Haematology* (Ed. Nilsson et al.), 33, p. 79–86 (1984).

Nilsson, I.M. et al., *Induction of Split Tolerance and Clinical Cure in High–Responding Hemophiliacs with Factor IX Antibodies, Proc. Natl. Acad. Sci. USA*, 83, p. 9169–9173 (1986).

Persic, L., et al., *An Integrated Vector System For The Eukaryotic Expression of Antibodies of Their Fragments After Selection From Phase Display Libraries, Genes*, p. 9–18 (1997).

Pluckthun, A., et al., *New Protein Engineering Approaches to Multivalent and Bispecific Antibody Fragments, Immunotechnology*, 3, p. 83–105 (1997).

Raag, R., et al., *Single–Chain Fvs, FASEB Journal*, 9(1), pp. 73–80 (1995).

Rees, A.R., et al., *Antibody Combining Sites: Structure and Prediction, Protein Structure Prediction—A Practical Approach* (Ed. M.J.E. Sternberg), Oxford University Press, Ch. 7, p. 141–172 (1996).

Roitt, I.M., et al., *Molecules which Recognize Antigen, Immunology*, $2^{nd}$ Edition, p. 5.1–5.11 (1989).

Sadler, J.E., et al., *Hemophila A, Hemophilia B, and von Willebrand's Disease, The Molecular Basis of Blood Diseases* (Ed. G. Stamatoyannopoulos et al.), p. 575–630 (1987).

Vaughan, T.J., et al., *Human Antibodies By Design, Nature Biotechnology*, p. 535–539 (1998).

Winter, G., et al., *Making Antibodies by Phage Display Technology, Annu. Rev. Immunol.*, 12, p. 433–455 (1994).

Zhong, D., et al., *Some Human Inhibitor Antibodies Interface with Factor VIII Binding to Factor IX, Blood*, 92(1), p. 136–142 (1998).

\* cited by examiner

Mouse V_H back primers (containing SfiI-site):

VH1BACK-SfiI    5' C ATG CCA TGA CTC GCG GCC CAG CCG GCC ATG GCC SAG GTS MAR CTG CAG
                SAG TCW GG 3' (SEQ.ID.NO. 50)

VH1BACKSfi     5' GTC CTC GCA ACT GCG GCC CAG CCG GCC ATG GCC GAG GTG CAG CTT CAG GAG TCA
               GG 3' (SEQ.ID.NO. 51)

VH2BACKSfi     5' GTC CTC GCA ACT GCG GCC CAG CCG GCC ATG GCC GAT GTG CAG CTT CAG GAG TCR
               GG 3' (SEQ.ID.NO. 52)

VH3BACKSfi     5' GTC CTC GCA ACT GCG GCC CAG CCG GCC ATG GCC CAG GTG CAG CTG AAG SAG TCA
               GG 3' (SEQ.ID.NO. 53)

VH4/6BACKSfi   5' GTC CTC GCA ACT GCG GCC CAG CCG GCC ATG GCC GAG GTY CAG CTG CAR CAR TCT
               GG 3' (SEQ.ID.NO. 54)

VH5/9BACKSfi   5' GTC CTC GCA ACT GCG GCC CAG CCG GCC ATG GCC CAG GTY CAR CTG CAG CAG YCT
               GG 3' (SEQ.ID.NO. 55)

VH7BACKSfi     5' GTC CTC GCA ACT GCG GCC CAG CCG GCC ATG GCC GAR GTG AAG CTG GTG GAR TCT
               GG 3' (SEQ.ID.NO. 56)

VH8BACKSfi     5' GTC CTC GCA ACT GCG GCC CAG CCG GCC ATG GCC GAG GTT CAG CTT CAG CAG TCT
               GG 3' (SEQ.ID.NO. 57)

VH10BACKSfi    5' GTC CTC GCA ACT GCG GCC CAG CCG GCC ATG GCC GAA GTG CAG CTG KTG GAG WCT
               GG 3' (SEQ.ID.NO. 58)

VH11BACKSfi    5' GTC CTC GCA ACT GCG GCC CAG CCG GCC ATG GCC CAG ATC CAG TTG CTG CAG TCT
               GG 3' (SEQ.ID.NO. 59)

FIG. 12-1

Mouse J_H forward primers (containing 1/2 linker-sequence and AscI-site):

VH1FOR2LiAsc    5' ACC GCC AGA GGC GCG CCC ACC TGA ACC GCC TCC ACC TGA GGA GAC GGT
                GAC CGT GGT CCC TTG GCC CC 3' (SEQ.ID.NO. 60)

JH1FORLiAsc     5' ACC GCC AGA GGC GCG CCC ACC TGA ACC GCC TCC ACC TGA GGA GAC GGT
                GAC CGT GGT CCC 3' (SEQ.ID.NO. 61)

JH2FORLiAsc     5' ACC GCC AGA GGC GCG CCC ACC TGA ACC GCC TCC ACC TGA GGA GAC TGT
                GAG AGT GGT GCC 3' (SEQ.ID.NO. 62)

JH3FORLiAsc     5' ACC GCC AGA GGC GCG CCC ACC TGA ACC GCC TCC ACC TGC AGA GAC AGT
                GAC CAG AGT CCC 3' (SEQ.ID.NO. 63)

JH4FORLiAsc     5' ACC GCC AGA GGC GCG CCC ACC TGA ACC GCC TCC ACC TGA GGA GAC GGT
                GAC TGA GGT TCC 3' (SEQ.ID.NO. 64)

FIG. 12-2

IUPAC-Code: M=A/C, W=A/T, R=A/G, Y=C/T, S=C/G, K=G/T, H=A/C/T, D=A/G/T, V=A/C/G, B=T/C/G.

Primers for cloning mouse V_K genes

Mouse V_K back primers (containing AscI-site and 1/2 linker-sequence):

| | |
|---|---|
| VK2BACK-LiAscI | 5' GGT TCA GAT GGG CGC GCC TCT GGC GGT GGC GGA TCG GAC ATT GAG CTC ACC CAG TCT CCA 3' (SEQ.ID.NO. 65) |
| VK1BACKLi Asc | 5' GGT TCA GAT GGG CGC GCC TCT GGC GGT GGC GGA TCG GAC ATT GTG ATG WCA CAG TCT CC 3' (SEQ.ID.NO. 66) |
| VK2BACKLi Asc | 5' GGT TCA GAT GGG CGC GCC TCT GGC GGT GGC GGA TCG GAT GTT KTG ATG ACC CAA ACT CC 3' (SEQ.ID.NO. 67) |
| VK3BACKLi Asc | 5' GGT TCA GAT GGG CGC GCC TCT GGC GGT GGC GGA TCG GAT ATT GTG ATR ACB CAG GCW GC 3' (SEQ.ID.NO. 68) |
| VK4BACKLi Asc | 5' GGT TCA GAT GGG CGC GCC TCT GGC GGT GGC GGA TCG GAC ATT GTG CTG ACM CAR TCT GC 3' (SEQ.ID.NO. 69) |
| VK5BACKLi Asc | 5' GGT TCA GAT GGG CGC GCC TCT GGC GGT GGC GGA TCG SAA AWT GTK CTC ACC CAG TCT CC 3' (SEQ.ID.NO. 70) |
| VK6BACKLi Asc | 5' GGT TCA GAT GGG CGC GCC TCT GGC GGT GGC GGA TCG GAY ATY VWG ATG ACM CAG WCT CC 3' (SEQ.ID.NO. 71) |
| VK7BACKLi Asc | 5' GGT TCA GAT GGG CGC GCC TCT GGC GGT GGC GGA TCG CAA ATT GTT CTC ACC CAG TCT CC 3' (SEQ.ID.NO. 72) |
| VK8BACKLi Asc | 5' GGT TCA GAT GGG CGC GCC TCT GGC GGT GGC GGA TCG TCA TTA TTG CAG GTG CTT GTG GG 3' (SEQ.ID.NO. 73) |

FIG. 13-1

Mouse J_K forward primers (containing NotI-site):

JK1NOT10   5' GAG TCA TTC TGC GGC CGC CCG TTT GAT TTC CAG CTT GGT GCC 3'
           (SEQ.ID.NO. 74)

JK2NOT10   5' GAG TCA TTC TGC GGC CGC CCG TTT TAT TTC CAG CTT GGT CCC 3'
           (SEQ.ID.NO. 75)

JK3NOT10   5' GAG TCA TTC TGC GGC CGC CCG TTT TAT TTC CAG TCT GGT CCC 3'
           (SEQ.ID.NO. 76)

JK4NOT10   5' GAG TCA TTC TGC GGC CGC CCG TTT TAT TTC CAA CTT TGT CCC 3'
           (SEQ.ID.NO. 77)

JK5NOT10   5' GAG TCA TTC TGC GGC CGC CCG TTT CAG CTC CAG CTT GGT CCC 3'
           (SEQ.ID.NO. 78)

IUPAC-Code: K=G/T, M=A/C, W=A/T, R=A/G, Y=C/T, S=C/G, H=A/C/T, D=A/G/T, V=A/C/G, B=T/C/G.

|  |  |  |  |  |  |  |  |  |  |  |  |  |  |
|---|---|---|---|---|---|---|---|---|---|---|---|---|---|
| +1 | E | V | K | L | V | E | S | G | P | E | L | K | K | P | G |
| 1 | GAG | GTG | AAG | CTG | GTG | GAG | TCT | GGA | CCT | GAG | CTG | AAG | AAG | CCT | GGA |

| +1 | E | T | V | K | I | S | C | K | A | S | G | Y | I | F | T |
|---|---|---|---|---|---|---|---|---|---|---|---|---|---|---|---|
| 46 | GAG | ACA | GTC | AAG | ATC | TCC | TGC | AAG | GCT | TCT | GGG | TAT | ATC | TTC | ACA |

| +1 | N | Y | G | M | N | W | V | K | Q | A | P | G | K | G | L |
|---|---|---|---|---|---|---|---|---|---|---|---|---|---|---|---|
| 91 | AAC | TAT | GGA | ATG | AAC | TGG | GTG | AAG | CAG | GCT | CCA | GGA | AAG | GGT | TTA |

| +1 | K | W | M | G | W | I | N | T | Y | T | G | E | P | T | Y |
|---|---|---|---|---|---|---|---|---|---|---|---|---|---|---|---|
| 136 | AAG | TGG | ATG | GGC | TGG | ATA | AAC | ACC | TAC | ACT | GGA | GAG | CCA | ACA | TAT |

| +1 | A | D | D | F | K | G | R | F | A | F | S | L | E | T | S |
|---|---|---|---|---|---|---|---|---|---|---|---|---|---|---|---|
| 181 | GCT | GAT | GAC | TTC | AAG | GGA | CGG | TTT | GCC | TTC | TCT | TTG | GAA | ACC | TCT |

| +1 | A | S | T | A | Y | L | Q | I | N | N | L | K | N | E | D |
|---|---|---|---|---|---|---|---|---|---|---|---|---|---|---|---|
| 226 | GCC | AGC | ACT | GCC | TAT | TTG | CAG | ATC | AAC | AAC | CTC | AAA | AAT | GAG | GAC |

| +1 | T | A | T | Y | F | C | A | L | Y | G | N | S | P | K | G |
|---|---|---|---|---|---|---|---|---|---|---|---|---|---|---|---|
| 271 | ACG | GCT | ACA | TAT | TTC | TGT | GCA | TTA | TAT | GGT | AAC | TCC | CCT | AAG | GGG |

*linker*

| +1 | F | A | Y | W | G | Q | G | T | L | V | T | V | S | A | G |
|---|---|---|---|---|---|---|---|---|---|---|---|---|---|---|---|
| 316 | TTT | GCT | TAC | TGG | GGC | CAA | GGG | ACT | CTG | GTC | ACT | GTC | TCT | GCA | GGT |

VL

| +1 | G | G | G | S | G | G | R | A | S | G | G | G | G | S | D |
|---|---|---|---|---|---|---|---|---|---|---|---|---|---|---|---|
| 361 | GGA | GGC | GGT | TCA | GGT | GGG | CGC | GCC | TCT | GGC | GGT | GGC | GGA | TCG | GAT |

| +1 | I | Q | M | T | Q | S | P | K | F | L | L | V | S | A | G |
|---|---|---|---|---|---|---|---|---|---|---|---|---|---|---|---|
| 406 | ATT | CAG | ATG | ACA | CAG | TCT | CCC | AAA | TTC | CTG | CTT | GTA | TCA | GCA | GGA |

FIG. 14-1

```
+1      D   R   V   T   I   T   C   K   A   S   Q   S   V   S   N
451     GAC AGG GTT ACC ATA ACC TGC AAG GCC AGT CAG AGT GTG AGT AAT

+1      D   V   A   W   Y   Q   Q   K   P   G   Q   S   P   K   L
496     GAT GTA GCT TGG TAC CAA CAG AAG CCG GGG CAG TCT CCT AAA CTA

+1      L   M   Y   Y   A   S   N   R   Y   T   G   V   P   D   R
541     CTG ATG TAC TAT GCA TCC AAT CGC TAC ACT GGA GTC CCT GAT CGC

+1      F   T   G   S   G   Y   G   T   D   F   T   F   T   I   S
586     TTC ACT GGC AGT GGA TAT GGG ACG GAT TTC ACT TTC ACC ATC AGC

+1      T   V   Q   A   E   D   L   A   V   Y   F   C   Q   Q   D
631     ACT GTG CAG GCT GAA GAC CTG GCA GTT TAT TTC TGT CAG CAG GAT

+1      Y   G   S   P   P   T   F   G   G   G   T   K   L   E   I
676     TAT GGC TCT CCT CCC ACG TTC GGA GGG GGC ACC AAG CTG GAA ATT

+1      K   R
721     AAA CGG
```

FIG. 14-2

```
        VH
 +1      E    V    Q    L    V    E    S    G    G    G    L    V    K    P    G
  1     GAA  GTG  CAG  CTG  GTG  GAG  TCT  GGG  GGA  GGC  CTA  GTG  AAG  CCT  GGA

+1      G    S    L    K    L    S    C    A    A    S    G    F    T    F    S
 46     GGG  TCC  CTG  AAA  CTC  TCC  TGT  GCA  GCC  TCT  GGA  TTC  ACT  TTC  AGT

+1      T    Y    T    M    S    W    V    R    Q    T    P    E    K    R    L
 91     ACC  TAT  ACC  ATG  TCT  TGG  GTT  CGC  CAG  ACT  CCG  GAG  AAG  AGG  CTG

+1      E    W    V    A    T    I    S    S    G    G    S    Y    T    Y    Y
136     GAG  TGG  GTC  GCA  ACC  ATT  AGT  AGT  GGT  GGT  AGT  TAC  ACC  TAC  TAT

+1      P    D    S    V    R    G    R    F    T    I    S    R    D    N    A
181     CCA  GAC  AGT  GTG  AGG  GGC  CGA  TTC  ACC  ATC  TCC  AGA  GAC  AAT  GCC

+1      K    N    T    L    Y    L    Q    M    S    S    L    K    S    E    D
226     AAG  AAC  ACC  CTG  TAC  CTG  CAA  ATG  AGC  AGT  CTG  AAG  TCT  GAG  GAC

+1      T    A    M    Y    Y    C    T    R    D    G    G    H    G    Y    G
271     ACA  GCC  ATG  TAT  TAC  TGT  ACA  AGA  GAT  GGG  GGA  CAC  GGG  TAC  GGT

+1      S    S    F    D    Y    W    G    Q    G    T    T    L    T    V    S
316     AGT  AGC  TTT  GAC  TAC  TGG  GGC  CAA  GGC  ACC  ACT  CTC  ACA  GTC  TCC linker
 +1      S    G    G    G    G    S    G    G    R    A    S    G    G    G    G
361     TCA  GGT  GGA  GGC  GGT  TCA  GGT  GGG  CGC  GCC  TCT  GGC  GGT  GGC  GGA VL
 +1      S    Q    I    V    L    T    Q    S    P    L    S    L    P    V    S
406     TCG  CAA  ATT  GTG  CTC  ACC  CAG  TCT  CCA  CTC  TCC  CTG  CCT  GTC  AGT
```

FIG. 15-1

```
+1       L   G   D   Q   A   S   I   S   C   R   S   S   Q   S   I
451     CTT GGA GAT CAA GCC TCC ATC TCT TGC AGA TCT AGT CAG AGC ATT

+1       V   H   S   N   G   N   T   Y   L   E   W   Y   L   Q   K
496     GTA CAT AGT AAT GGA AAC ACC TAT TTA GAA TGG TAC CTG CAG AAA

+1       P   G   Q   S   P   K   L   L   I   Y   K   V   S.  N   R
541     CCA GGC CAG TCT CCA AAG CTC CTG ATC TAC AAA GTT TCC AAC CGA

+1       F   S   G   V   P   D   K   F   S   G   S   G   S   G   T
586     TTT TCT GGG GTC CCA GAC AAA TTC AGT GGC AGT GGA TCA GGG ACA

+1       D   F   T   L   K   I   S   R   V   E   A   E   D   L   G
631     GAT TTC ACA CTC AAG ATC AGC AGA GTG GAG GCT GAG GAT CTG GGA

+1       V   Y   Y   C   F   Q   G   S   H   V   P   W   T   F   G
676     GTT TAT TAC TGC TTT CAA GGT TCA CAT GTT CCG TGG ACG TTC GGT

+1       G   G   T   K   L   E   I   K   R
721     GGA GGC ACC AAG CTG GAA ATC AAA CGG
```

FIG. 15-2

```
+1    E    V    Q    L    Q    E    S    G    G    G    L    V    K    P    G
 1    GAG  GTG  CAG  CTT  CAG  GAG  TCA  GGG  GGA  GGC  TTA  GTG  AAG  CCT  GGA

+1    G    S    L    K    L    S    C    A    A    S    G    F    T    F    S
 46   GGG  TCC  CTG  AAA  CTC  TCC  TGT  GCA  GCC  TCT  GGA  TTC  ACT  TTC  AGT

+1    S    Y    T    M    S    W    V    R    Q    T    P    E    K    R    L
 91   AGC  TAT  ACC  ATG  TCT  TGG  GTT  CGC  CAG  ACT  CCG  GAG  AAG  AGG  CTG

+1    E    W    V    A    T    I    S    S    G    G    S    S    T    Y    Y
 136  GAG  TGG  GTC  GCA  ACC  ATT  AGT  AGT  GGT  GGT  AGT  TCC  ACC  TAC  TAT

+1    P    D    S    V    K    G    R    F    T    I    S    R    D    N    A
 181  CCA  GAC  AGT  GTG  AAG  GGC  CGA  TTC  ACC  ATC  TCC  AGA  GAC  AAT  GCC

+1    K    N    T    L    Y    L    Q    M    S    S    L    R    S    E    D
 226  AAG  AAC  ACC  CTG  TAC  CTG  CAA  ATG  AGC  AGT  CTG  AGG  TCT  GAG  GAC

+1    T    A    M    Y    Y    C    T    R    E    G    G    F    T    V
 271  ACA  GCC  ATG  TAT  TAC  TGT  ACA  AGA  GAG  GGG  GGT  GGT  TTC  ACC  GTC

+1    N    W    Y    F    D    V    W    G    A    G    T    L    V    T    V
 316  AAC  TGG  TAC  TTC  GAT  GTC  TGG  GGC  GCA  GGG  ACT  CTG  GTC  ACT  GTC linker
+1    S    A    G    G    G    G    S    G    G    R    A    S    G    G    G
 361  TCT  GCA  GGT  GGA  GGC  GGT  TCA  GGT  GGG  CGC  GCC  TCT  GGC  GGT  GGC VL
+1    G    S    E    N    V    L    T    Q    S    P    A    S    L    A    V
 406  GGA  TCG  GAA  AAT  GTG  CTC  ACC  CAG  TCT  CCA  GCT  TCT  TTG  GCT  GTG
```

FIG. 16-1

```
+1   S    L    G    Q    R    A    T    I    S    C    R    A    S    E    S
451  TCT  CTA  GGG  CAG  AGG  GCC  ACC  ATA  TCC  TGC  AGA  GCC  AGT  GAA  AGT

+1   V    D    S    Y    G    Y    N    F    M    H    W    Y    Q    Q    I
496  GTT  GAT  AGT  TAT  GGC  TAT  AAT  TTT  ATG  CAC  TGG  TAT  CAG  CAG  ATA

+1   P    G    Q    P    P    K    L    L    I    Y    R    A    S    N    L
541  CCA  GGA  CAG  CCA  CCC  AAA  CTC  CTC  ATC  TAT  CGT  GCA  TCC  AAC  CTA

+1   E    S    G    I    P    A    R    F    S    G    S    G    S    R    T
586  GAG  TCT  GGG  ATC  CCT  GCC  AGG  TTC  AGT  GGC  AGT  GGG  TCT  AGG  ACA

+1   D    F    T    L    T    I    N    P    V    E    A    D    D    V    A
631  GAC  TTC  ACC  CTC  ACC  ATT  AAT  CCT  GTG  GAG  GCT  GAT  GAT  GTT  GCA

+1   T    Y    Y    C    Q    Q    S    N    E    D    P    L    T    F    G
676  ACC  TAT  TAC  TGT  CAG  CAA  AGT  AAT  GAG  GAT  CCG  CTC  ACG  TTC  GGT

+1   T    G    T    R    L    E    I    K    R
721  ACT  GGG  ACC  AGA  CTG  GAA  ATA  AAA  CGG
```

FIG. 16-2

```
       VH
        V   Q   L   Q   E   S   G   G   G   L   V   K   P   G   G   S   L   K   L
+1      GAG GTG CAG CTT CAG GAG TCA GGG GGA GGC TTA GTG AAG CCT GGA GGG TCC CTG AAA CTC
 +1 1   CTC CAC GTC GAA GTC CTC AGT CCC CCT CCG AAT CAC TTC CCT CCC AGG GAC TTT GAG

S   C   A   A   S   G   F   I   F   S   Y   T   M   S   W   V   R   Q   T
+1      TCC TGT GCA GCC TCT GGA TTC ATT TTT AGT AGT TAT ACC ATG TCT TGG GTT CGC CAG ACT
 +1 61  AGG ACA CGT CGG AGA CCT AAG TAA AAA TCA TCA ATA TGG TAC AGA ACC CAA GCG GTC TGA

P   E   K   R   L   E   W   V   A   T   I   S   S   G   G   S   Y   T   Y
+1      CCG GAG AAG AGG CTG GAG TGG GTC GCA ACC ATT AGT AGT GGT GGT TCC TAC ACC TAT TAT
 +1 121 GGC CTC TTC TCC GAC CTC ACC CAG CGT TGG TAA TCA TCA CCA CCA AGG ATG TGG ATA ATA

P   D   S   V   K   G   R   F   T   I   S   R   D   N   A   K   N   T   L   Y
+1      CCA GAC AGT GTG AAG GGC CGA TTC ACC ATC TCC AGA GAC AAT GCC AAG AAC ACC CTG TAC
 +1 181 GGT CTG TCA CAC TTC CCG GCT AAG TGG TAG AGG TCT CTG TTA CGG TTC TTG TGG GAC ATG

L   Q   M   S   S   L   K   S   E   D   T   A   M   Y   Y   C   T   R   T   L   T   V
+1      CTG CAA ATG AGC AGT CTG AAG TCT GAG GAC ACA GCC ATG TAT TAC TGT ACA ACT CTC ACA GTC
 +1 241 GAC GTT TAC TCG TCA GAC TTC AGA CTC CTG TGT CGG TAC ATA ATG ACA TGT TGA GAG TGT CAG

G   G   Y   Y   Y   N   W   F   D   V   W   G   A   G   T   T   L   T   V
+1      GGT GGT TAT TAC TAC AAC TGG TTT GAT GTC TGG GGC GCA GGG ACC ACG CTC ACC GTC
 +1 301 CCA CCA ATA ATG ATG TTG ACC AAA CTA CAG ACC CCG CGT CCC TGG TGC GAG TGG CAG

VL
            linker
        S   S   G   G   G   G   S   P   A   S   L   A   V   S   L   G   Q   R   A   T   I   S   C
+1      TCC TCA GGT GGA GGC GGT TCA CCA GCT TCT TTG GCT GTG TCT CTA GGG CAG AGG GCC ATT AGC
 +1 361 AGG AGT CCA CCT CCG CCA AGT GGT CGA AGA AAC CGA CAC AGA GAT CCC GTC TCC CGG TAA CTC L   T   Q   S   P   A   S   L   A   V   S   L   G   Q   R   A   T   I   S   C
+1      CTC ACN CAG TCT CCA GCT TCT TTG GCT GTG TCT CTA GGG CAG AGG GCC ACC ATA TCC TGC
 +1 421 GAG TGN GTC AGA GGT CGA AGA AAC CGA CAC AGA GAT CCC GTC TCC CGG TGG TAT AGG ACG
```

FIG. 17-1

```
       R   A   S   E   S   V   D   S   Y   G   K   S   F   M   H   W   Y   Q   Q   K
+1   AGA GCC AGT GAA AGT GTT GAT AGT TAT GGC AAG AGT TTT ATG CAC TGG TAC CAG CAG AAA
481  TCT CGG TCA CTT TCA CAA CTA TCA ATA CCG TTC TCA AAA TAC GTG ACC ATG GTC GTC TTT

P   G   Q   Q   P   P   K   L   I   Y   R   A   S   N   L   E   S   G   I   P
+1   CCA GGG CAG CAG CCA CCC AAA CTC ATC TAT CGT GCA TCC AAC CTA GAA TCT GGG ATC CCT
541  GGT CCC GTC GTC GGT GGG TTT GAG TAG ATA GCA CGT AGG TTG GAT CTT AGA CCC TAG GGA

A   R   F   S   G   S   R   T   D   F   T   L   T   I   N   P   V   E
+1   GCC AGG TTC AGT GGC AGT GGG TCT AGG ACA GAC TTC ACC CTC ACC ATT AAT CCT GTG GAG
601  CGG TCC AAG TCA CCG TCA CCC AGA TCC TGT CTG AAG TGG GAG TGG TAA GGA CAC CTC

A   D   D   V   A   T   Y   Y   C   Q   Q   S   N   E   D   P   L   T   F   G
+1   GCC GAT GAT GTT GCN ACC TAT TAC TGT CAG CAA AGT AAT GAG GAT CCC CTC ACG TTC GGT
661  CGG CTA CTA CAA CGN TGG ATA ATG ACA GTC GTT TCA TTA CTC CTA GGG GAG TGC AAG CCA

A   G   T   R   L   E   I   K   R
+1   GCT GGG ACC AGA CTG GAA ATA AAA CGG
721  CGA CCC TGG TCT GAC CTT TAT TTT GCC
```

FIG. 17-2

```
      PelB-Leader
  +1   M    K    Y    L    L    P    T    A    A    A    G    L    L    L
   1  ATG  AAA  TAC  CTA  TTG  CCT  ACG  GCA  GCC  GCT  GGA  TTG  TTA  TTA
      TAC  TTT  ATG  GAT  AAC  GGA  TGC  CGT  CGG  CGA  CCT  AAC  AAT  AAT VH
  +1   L    A    A    Q    P    A    M    A    E    V    K    L    V    E
  43  CTC  GCG  GCC  CAG  CCG  GCC  ATG  GCG  GAG  GTG  AAG  CTG  GTG  GAG
      GAG  CGC  CGG  GTC  GGC  CGG  TAC  CGC  CTC  CAC  TTC  GAC  CAC  CTC +1   S    G    G    G    L    V    K    P    G    G    S    L    K    L
  85  TCT  GGG  GGA  GGC  TTA  GTG  AAG  CCT  GGA  GGG  TCC  CTG  AAA  CTC
      AGA  CCC  CCT  CCG  AAT  CAC  TTC  GGA  CCT  CCC  AGG  GAC  TTT  GAG +1   S    C    A    A    S    G    F    T    F    S    S    Y    T    M
 127  TCC  TGT  GCA  GCC  TCT  GGA  TTC  ACT  TTC  AGT  AGC  TAT  ACC  ATG
      AGG  ACA  CGT  CGG  AGA  CCT  AAG  TGA  AAG  TCA  TCG  ATA  TGG  TAC +1   S    W    V    R    Q    T    P    E    K    R    L    E    W    V
 169  TCT  TGG  GTT  CGC  CAG  ACT  CCG  GAG  AAG  AGG  CTG  GAG  TGG  GTC
      AGA  ACC  CAA  GCG  GTC  TGA  GGC  CTC  TTC  TCC  GAC  CTC  ACC  CAG +1   A    T    I    S    S    G    G    S    T    Y    Y    P    D
 211  GCA  ACC  ATT  AGT  AGT  GGN  GGT  AGT  TCC  ACC  TAC  TAT  CCA  GAC
      CGT  TGG  TAA  TCA  TCA  CCN  CCA  TCA  AGG  TGG  ATG  ATA  GGT  CTG +1   S    V    K    G    R    F    T    I    S    R    D    N    A    K
 253  AGT  GTG  AAG  GGC  CGA  TTC  ACC  ATC  TCC  AGA  GAC  AAT  GCC  AAG
      TCA  CAC  TTC  CCG  GCT  AAG  TGG  TAG  AGG  TCT  CTG  TTA  CGG  TTC +1   N    T    L    Y    L    Q    M    S    S    L    R    S    E    D
 295  AAC  ACC  CTG  TAC  CTG  CAA  ATG  AGC  AGT  CTG  AGG  TCT  GAG  GAC
      TTG  TGG  GAC  ATG  GAC  GTT  TAC  TCG  TCA  GAC  TCC  AGA  CTC  CTG +1   T    A    M    Y    Y    C    T    R    E    G    G    G    F    T
 337  ACA  GCC  ATG  TAT  TAC  TGT  ACA  AGA  GAG  GGG  GGT  GGT  TTC  ACC
      TGT  CGG  TAC  ATA  ATG  ACA  TGT  TCT  CTC  CCC  CCA  CCA  AAG  TGG +1   V    N    W    Y    F    D    V    W    G    A    G    T    S    V
 379  GTC  AAC  TGG  TAC  TTC  GAT  GTC  TGG  GGC  GCA  GGA  ACC  TCA  GTC
      CAG  TTG  ACC  ATG  AAG  CTA  CAG  ACC  CCG  CGT  CCT  TGG  AGT  CAG linker
  +1   T    V    S    S    G    G    G    G    S    G    G    R    A    S
 421  ACC  GTC  TCC  TCA  GGT  GGA  GGC  GGT  TCA  GGT  GGG  CGC  GCC  TCT
      TGG  CAG  AGG  AGT  CCA  CCT  CCG  CCA  AGT  CCA  CCC  GCG  CGG  AGA
```

FIG. 26-1

```
                                        │VL
     +1   G    G    G    G    S   │ D    I    V    L    T    Q    S    P    A
    463  GGC  GGT  GGC  GGA  TCG   GAC  ATT  GTG  CTG  ACA  CAG  TCT  CCA  GCT
         CCG  CCA  CCG  CCT  AGC   CTG  TAA  CAC  GAC  TGT  GTC  AGA  GGT  CGA

+1   S    L    A    V    S    L    G    Q    R    A    T    I    S    C
    505  TCT  TTG  GCT  GTG  TCT  CTA  GGG  CAG  AGG  GCC  ACC  ATA  TCC  TGC
         AGA  AAC  CGA  CAC  AGA  GAT  CCC  GTC  TCC  CGG  TGG  TAT  AGG  ACG

+1   R    A    S    E    S    V    D    S    Y    G    Y    N    F    M
    547  AGA  GCC  AGT  GAA  AGT  GTT  GAT  AGT  TAT  GGC  TAT  AAT  TTT  ATG
         TCT  CGG  TCA  CTT  TCA  CAA  CTA  TCA  ATA  CCG  ATA  TTA  AAA  TAC

+1   H    W    Y    Q    Q    I    P    G    Q    P    P    K    L    L
    589  CAC  TGG  TAT  CAG  CAG  ATA  CCA  GGA  CAG  CCA  CCC  AAA  CTC  CTC
         GTG  ACC  ATA  GTC  GTC  TAT  GGT  CCT  GTC  GGT  GGG  TTT  GAG  GAG

+1   I    Y    R    A    S    N    L    E    S    G    I    P    A    R
    631  ATC  TAT  CGT  GCA  TCC  AAC  CTA  GAG  TCT  GGG  ATC  CCT  GCC  AGG
         TAG  ATA  GCA  CGT  AGG  TTG  GAT  CTC  AGA  CCC  TAG  GGA  CGG  TCC

+1   F    S    G    S    G    S    R    T    D    F    T    L    T    I
    673  TTC  AGT  GGC  AGT  GGG  TCT  AGG  ACA  GAC  TTC  ACC  CTC  ACC  ATT
         AAG  TCA  CCG  TCA  CCC  AGA  TCC  TGT  CTG  AAG  TGG  GAG  TGG  TAA

+1   N    P    V    E    A    D    D    V    A    T    Y    Y    C    Q
    715  AAT  CCT  GTG  GAG  GCT  GAT  GAT  GTT  GCA  ACC  TAT  TAC  TGT  CAG
         TTA  GGA  CAC  CTC  CGA  CTA  CTA  CAA  CGT  TGG  ATA  ATG  ACA  GTC

+1   Q    S    N    E    D    P    L    T    F    G    T    G    T    R
    757  CAA  AGT  AAT  GAG  GAT  CCG  CTC  ACG  TTC  GGT  ACT  GGG  ACC  AGA
         GTT  TCA  TTA  CTC  CTA  GGC  GAG  TGC  AAG  CCA  TGA  CCC  TGG  TCT

│Spacer            │Alkaline phosphatase
     +1   L    E    I    K    R   │ A    A    A    A   │ R    A    P    E    M
    799  CTG  GAA  ATA  AAA  CGG   GCG  GCC  GCA  GCC   CGG  GCA  CCA  GAA  ATG
         GAC  CTT  TAT  TTT  GCC   CGC  CGG  CGT  CGG   GCC  CGT  GGT  CTT  TAC +1   P    V    L    E    N    R    A    A    Q    G    D    I    T    A
    841  CCT  GTT  CTG  GAA  AAC  CGG  GCT  GCT  CAG  GGC  GAT  ATT  ACT  GCA
         GGA  CAA  GAC  CTT  TTG  GCC  CGA  CGA  GTC  CCG  CTA  TAA  TGA  CGT +1   P    G    G    A    R    R    L    T    G    D    Q    T    A    A
    883  CCC  GGC  GGT  GCT  CGC  CGT  TTA  ACG  GGT  GAT  CAG  ACT  GCC  GCT
         GGG  CCG  CCA  CGA  GCG  GCA  AAT  TGC  CCA  CTA  GTC  TGA  CGG  CGA +1   L    R    D    S    L    S    D    K    P    A    K    N    I    I
    925  CTG  CGT  GAT  TCT  CTT  AGC  GAT  AAA  CCT  GCA  AAA  AAT  ATT  ATT
         GAC  GCA  CTA  AGA  GAA  TCG  CTA  TTT  GGA  CGT  TTT  TTA  TAA  TAA
```

FIG. 26-2

```
     +1   L    L    I    G    D    G    M    G    D    S    E    I    T    A
     463  TTG  CTG  ATT  GGC  GAT  GGG  ATG  GGG  GAC  TCG  GAA  ATT  ACT  GCC
          AAC  GAC  TAA  CCG  CTA  CCC  TAC  CCC  CTG  AGC  CTT  TAA  TGA  CGG

+1   A    R    N    Y    A    E    G    A    G    G    F    F    K    G
     505  GCA  CGT  AAT  TAT  GCC  GAA  GGT  GCG  GGC  GGC  TTT  TTT  AAA  GGT
          CGT  GCA  TTA  ATA  CGG  CTT  CCA  CGC  CCG  CCG  AAA  AAA  TTT  CCA

+1   I    D    A    L    P    L    T    G    Q    Y    T    H    Y    A
     1051 ATA  GAT  GCC  TTA  CCG  CTT  ACC  GGG  CAA  TAC  ACT  CAC  TAT  GCG
          TAT  CTA  CGG  AAT  GGC  GAA  TGG  CCC  GTT  ATG  TGA  GTG  ATA  CGC

+1   L    N    K    K    T    G    K    P    D    Y    V    T    D    S
     1093 CTG  AAT  AAA  AAA  ACC  GGC  AAA  CCG  GAC  TAC  GTC  ACC  GAC  TCG
          GAC  TTA  TTT  TTT  TGG  CCG  TTT  GGC  CTG  ATG  CAG  TGG  CTG  AGC

+1   A    A    S    A    T    A    W    S    T    G    V    K    T    Y
     1135 GCT  GCA  TCA  GCA  ACC  GCC  TGG  TCA  ACC  GGT  GTC  AAA  ACC  TAT
          CGA  CGT  AGT  CGT  TGG  CGG  ACC  AGT  TGG  CCA  CAG  TTT  TGG  ATA

+1   N    G    A    L    G    V    D    I    H    E    K    D    H    P
     1177 AAC  GGC  GCG  CTG  GGC  GTC  GAT  ATT  CAC  GAA  AAA  GAT  CAC  CCA
          TTG  CCG  CGC  GAC  CCG  CAG  CTA  TAA  GTG  CTT  TTT  CTA  GTG  GGT

+1   T    I    L    E    M    A    K    A    A    G    L    A    T    G
     1219 ACG  ATT  CTG  GAA  ATG  GCA  AAA  GCC  GCA  GGT  CTG  GCG  ACC  GGT
          TGC  TAA  GAC  CTT  TAC  CGT  TTT  CGG  CGT  CCA  GAC  CGC  TGG  CCA

+1   N    V    S    T    A    E    L    Q    D    A    T    P    A    A
     1261 AAC  GTT  TCT  ACC  GCA  GAG  TTG  CAG  GAT  GCC  ACG  CCC  GCT  GCG
          TTG  CAA  AGA  TGG  CGT  CTC  AAC  GTC  CTA  CGG  TGC  GGG  CGA  CGC

+1   L    V    A    H    V    T    S    R    K    C    Y    G    P    S
     1303 CTG  GTG  GCA  CAT  GTG  ACC  TCG  CGC  AAA  TGC  TAC  GGT  CCG  AGC
          GAC  CAC  CGT  GTA  CAC  TGG  AGC  GCG  TTT  ACG  ATG  CCA  GGC  TCG

+1   A    T    S    E    K    C    P    G    N    A    L    E    K    G
     1345 GCG  ACC  AGT  GAA  AAA  TGT  CCG  GGT  AAC  GCT  CTG  GAA  AAA  GGC
          CGC  TGG  TCA  CTT  TTT  ACA  GGC  CCA  TTG  CGA  GAC  CTT  TTT  CCG

+1   G    K    G    S    I    T    E    Q    L    L    N    A    R    A
     1387 GGA  AAA  GGA  TCG  ATT  ACC  GAA  CAG  CTG  CTT  AAC  GCT  CGT  GCC
          CCT  TTT  CCT  AGC  TAA  TGG  CTT  GTC  GAC  GAA  TTG  CGA  GCA  CGG

+1   D    V    T    L    G    G    G    A    K    T    F    A    E    T
     1429 GAC  GTT  ACG  CTT  GGC  GGC  GGC  GCA  AAA  ACC  TTT  GCT  GAA  ACG
          CTG  CAA  TGC  GAA  CCG  CCG  CCG  CGT  TTT  TGG  AAA  CGA  CTT  TGC
```

FIG. 26-3

```
      +1  A    T    A    G    E    W    Q    G    K    T    L    R    E    Q
    1471  GCA  ACC  GCT  GGT  GAA  TGG  CAG  GGA  AAA  ACG  CTG  CGT  GAA  CAG
          CGT  TGG  CGA  CCA  CTT  ACC  GTC  CCT  TTT  TGC  GAC  GCA  CTT  GTC

+1  A    Q    A    R    G    Y    Q    L    V    S    D    A    A    S
    1513  GCA  CAG  GCG  CGT  GGT  TAT  CAG  TTG  GTG  AGC  GAT  GCT  GCC  TCA
          CGT  GTC  CGC  GCA  CCA  ATA  GTC  AAC  CAC  TCG  CTA  CGA  CGG  AGT

+1  L    N    S    V    T    E    A    N    Q    Q    K    P    L    L
    1555  CTG  AAT  TCG  GTG  ACG  GAA  GCG  AAT  CAG  CAA  AAA  CCC  CTG  CTT
          GAC  TTA  AGC  CAC  TGC  CTT  CGC  TTA  GTC  GTT  TTT  GGG  GAC  GAA

+1  G    L    F    A    D    G    N    M    P    V    R    W    L    G
    1177  GGC  CTG  TTT  GCT  GAC  GGC  AAT  ATG  CCA  GTG  CGC  TGG  CTA  GGA
          CCG  GAC  AAA  CGA  CTG  CCG  TTA  TAC  GGT  CAC  GCG  ACC  GAT  CCT

+1  P    K    A    T    Y    H    G    N    I    D    K    P    A    V
    1639  CCG  AAA  GCA  ACG  TAC  CAT  GGC  AAT  ATC  GAT  AAG  CCC  GCA  GTC
          GGC  TTT  CGT  TGC  ATG  GTA  CCG  TTA  TAG  CTA  TTC  GGG  CGT  CAG

+1  T    C    T    P    N    P    Q    R    N    D    S    V    P    T
    1681  ACC  TGT  ACG  CCA  AAT  CCG  CAA  CGT  AAT  GAC  AGT  GTA  CCA  ACC
          TGG  ACA  TGC  GGT  TTA  GGC  GTT  GCA  TTA  CTG  TCA  CAT  GGT  TGG

+1  L    A    Q    M    T    D    K    A    I    E    L    L    S    K
    1723  CTG  GCG  CAG  ATG  ACC  GAC  AAA  GCC  ATT  GAA  TTG  TTG  AGT  AAA
          GAC  CGC  GTC  TAC  TGG  CTG  TTT  CGG  TAA  CTT  AAC  AAC  TCA  TTT

+1  N    E    K    G    F    F    L    Q    V    E    G    A    S    I
    1765  AAT  GAG  AAA  GGC  TTT  TTC  CTG  CAA  GTT  GAA  GGT  GCG  TCA  ATC
          TTA  CTC  TTT  CCG  AAA  AAG  GAC  GTT  CAA  CTT  CCA  CGC  AGT  TAG

+1  D    K    Q    D    H    A    A    N    P    C    G    Q    I    G
    1807  GAT  AAA  CAG  GAT  CAT  GCT  GCG  AAT  CCT  TGT  GGG  CAA  ATT  GGC
          CTA  TTT  GTC  CTA  GTA  CGA  CGC  TTA  GGA  ACA  CCC  GTT  TAA  CCG

+1  E    T    V    D    L    D    E    A    V    Q    R    A    L    E
    1849  GAG  ACG  GTC  GAT  CTC  GAT  GAA  GCC  GTA  CAA  CGG  GCG  CTG  GAA
          CTC  TGC  CAG  CTA  GAG  CTA  CTT  CGG  CAT  GTT  GCC  CGC  GAC  CTT

+1  F    A    K    K    E    G    N    T    L    V    I    V    T    A
    1891  TTC  GCT  AAA  AAG  GAG  GGT  AAC  ACG  CTG  GTC  ATA  GTC  ACC  GCT
          AAG  CGA  TTT  TTC  CTC  CCA  TTG  TGC  GAC  CAG  TAT  CAG  TGG  CGA

+1  D    H    A    H    A    S    Q    I    V    A    P    D    T    K
    1933  GAT  CAC  GCC  CAC  GCC  AGC  CAG  ATT  GTT  GCG  CCG  GAT  ACC  AAA
          CTA  GTG  CGG  GTG  CGG  TCG  GTC  TAA  CAA  CGC  GGC  CTA  TGG  TTT

+1  A    P    G    L    T    Q    A    L    N    T    K    D    G    A
    1975  GCT  CCG  GGC  CTC  ACC  CAG  GCG  CTA  AAT  ACC  AAA  GAT  GGC  GCA
          CGA  GGC  CCG  GAG  TGG  GTC  CGC  GAT  TTA  TGG  TTT  CTA  CCG  CGT
```

FIG. 26-4

```
     +1   V   M   V   M   S   Y   G   N   S   E   E   D   S   Q
     2017 GTG ATG GTG ATG AGT TAC GGG AAC TCC GAA GAG GAT TCA CAA
          CAC TAC CAC TAC TCA ATG CCC TTG AGG CTT CTC CTA AGT GTT

+1   E   H   T   G   S   Q   L   R   I   A   A   Y   G   P
     2059 GAA CAT ACC GGC AGT CAG TTG CGT ATT GCG GCG TAT GGC CCG
          CTT GTA TGG CCG TCA GTC AAC GCA TAA CGC CGC ATA CCG GGC

+1   H   A   A   N   V   V   G   L   T   D   Q   T   D   L
     2101 CAT GCC GCC AAT GTT GTT GGA CTG ACC GAC CAG ACC GAT CTC
          GTA CGG CGG TTA CAA CAA CCT GAC TGG CTG GTC TGG CTA GAG

|His tag
     +1   F   Y   T   M   K   A   A   L   G   D   I |  A   H   H
     2143 TTC TAC ACC ATG AAA GCC GCT CTG GGG GAT ATC|GCA CAC CAT
          AAG ATG TGG TAC TTT CGG CGA GAC CCC CTA TAG|CGT GTG GTA +1   H   H   H   H   *
     2185 CAC CAT CAC CAT TAA
          GTG GTA GTG GTA ATT
```

FIG. 26-5

PelB-Leader
```
     +1   M   K   Y   L   L   P   T   A   A   A   G   L   L   L   L
      1  ATG AAA TAC CTA TTG CCT ACG GCA GCC GCT GGA TTG TTA TTA CTC
         TAC TTT ATG GAT AAC GGA TGC CGT CGG CGA CCT AAC AAT AAT GAG +1   A   A   Q   P   A   M   A   E   V   K   L   V   E   S   G
     46  GCG GCC CAG CCG GCC ATG GCG GAG GTG AAG CTG GTG GAG TCT GGG
         CGC CGG GTC GGC CGG TAC CGC CTC CAC TTC GAC CAC CTC AGA CCC +1   G   G   L   V   K   P   G   G   S   L   K   L   S   C   A
     91  GGA GGC TTA GTG AAG CCT GGA GGG TCC CTG AAA CTC TCC TGT GCA
         CCT CCG AAT CAC TTC GGA CCT CCC AGG GAC TTT GAG AGG ACA CGT +1   A   S   G   F   T   F   S   S   Y   T   M   S   W   V   R
    136  GCC TCT GGA TTC ACT TTC AGT AGC TAT ACC ATG TCT TGG GTT CGC
         CGG AGA CCT AAG TGA AAG TCA TCG ATA TGG TAC AGA ACC CAA GCG +1   Q   T   P   E   K   R   L   E   W   V   A   T   I   S   S
    181  CAG ACT CCG GAG AAG AGG CTG GAG TGG GTC GCA ACC ATT AGT AGT
         GTC TGA GGC CTC TTC TCC GAC CTC ACC CAG CGT TGG TAA TCA TCA +1   G   G   S   T   Y   Y   P   D   S   V   K   G   R   F
    226  GGN GGT AGT TCC ACC TAC TAT CCA GAC AGT GTG AAG GGC CGA TTC
         CCN CCA TCA AGG TGG ATG ATA GGT CTG TCA CAC TTC CCG GCT AAG +1   T   I   S   R   D   N   A   K   N   T   L   Y   L   Q   M
    271  ACC ATC TCC AGA GAC AAT GCC AAG AAC ACC CTG TAC CTG CAA ATG
         TGG TAG AGG TCT CTG TTA CGG TTC TTG TGG GAC ATG GAC GTT TAC +1   S   S   L   R   S   E   D   T   A   M   Y   Y   C   T   R
    316  AGC AGT CTG AGG TCT GAG GAC ACA GCC ATG TAT TAC TGT ACA AGA
         TCG TCA GAC TCC AGA CTC CTG TGT CGG TAC ATA ATG ACA TGT TCT +1   E   G   G   G   F   T   V   N   W   Y   F   D   V   W   G
    361  GAG GGG GGT GGT TTC ACC GTC AAC TGG TAC TTC GAT GTC TGG GGC
         CTC CCC CCA CCA AAG TGG CAG TTG ACC ATG AAG CTA CAG ACC CCG
```
                                                       Linker
```
     +1   A   G   T   S   V   T   V   S   S   G   G   G   S   G
    406  GCA GGA ACC TCA GTC ACC GTC TCC TCA GGT GGA GGC GGT TCA GGT
         CGT CCT TGG AGT CAG TGG CAG AGG AGT CCA CCT CCG CCA AGT CCA
```
                                                       VL
```
     +1   G   R   A   S   G   G   G   G   S   D   I   V   L   T   Q
    451  GGG CGC GCC TCT GGC GGT GGC GGA TCG GAC ATT GTG CTG ACA CAG
         CCC GCG CGG AGA CCG CCA CCG CCT AGC CTG TAA CAC GAC TGT GTC
```

FIG. 28-1

```
     +1   X    P    A    S    L    A    V    S    L    G    Q    R    A    T    I
     496  TNT  CCA  GCT  TCT  TTG  GCT  GTG  TCT  CTA  GGG  CAG  AGG  GCC  ACC  ATA
          ANA  GGT  CGA  AGA  AAC  CGA  CAC  AGA  GAT  CCC  GTC  TCC  CGG  TGG  TAT

+1   S    C    R    A    S    E    S    V    D    S    Y    G    Y    N    F
     541  TCN  TGC  AGA  GCC  AGT  GAA  AGT  GTT  GAT  AGT  TAT  GGC  TAT  AAT  TTT
          AGN  ACG  TCT  CGG  TCA  CTT  TCA  CAA  CTA  TCA  ATA  CCG  ATA  TTA  AAA

+1   M    H    W    Y    Q    Q    I    P    G    Q    P    P    K    L    L
     586  ATG  CAC  TGG  TAT  CAG  CAG  ATA  CCA  GGA  CAG  CCA  CCC  AAA  CTC  CTC
          TAC  GTG  ACC  ATA  GTC  GTC  TAT  GGT  CCT  GTC  GGT  GGG  TTT  GAG  GAG

+1   I    Y    R    A    S    N    L    E    S    G    I    P    A    R    F
     631  ATC  TAT  CGT  GCA  TCC  AAC  CTA  GAG  TCT  GGG  ATC  CCT  GCC  AGG  TTC
          TAG  ATA  GCA  CGT  AGG  TTG  GAT  CTC  AGA  CCC  TAG  GGA  CGG  TCC  AAG

+1   S    G    S    G    S    R    T    D    F    T    L    T    I    N    P
     676  AGT  GGC  AGT  GGG  TCT  AGG  ACA  GAC  TTC  ACC  CTC  ACC  ATT  AAT  CCT
          TCA  CCG  TCA  CCC  AGA  TCC  TGT  CTG  AAG  TGG  GAG  TGG  TAA  TTA  GGA

+1   V    E    A    D    D    V    A    T    Y    Y    C    Q    Q    S    N
     721  GTG  GAG  GCT  GAT  GAT  GTT  GCA  ACC  TAT  TAC  TGT  CAG  CAA  AGT  AAT
          CAC  CTC  CGA  CTA  CTA  CAA  CGT  TGG  ATA  ATG  ACA  GTC  GTT  TCA  TTA

+1   E    D    P    L    T    F    G    T    G    T    R    L    E    I    K
     766  GAG  GAT  CCG  CTC  ACG  TTC  GGT  ACT  GGG  ACC  AGA  CTG  GAA  ATA  AAA
          CTC  CTA  GGC  GAG  TGC  AAG  CCA  TGA  CCC  TGG  TCT  GAC  CTT  TAT  TTT

Spacer         Hinge                                        Helix

+1   R    A    A    A    P    K    P    S    T    P    P    G    S    S    R
     811  CGG  GCG  GCC  GCA  CCG  AAG  CCT  TCC  ACT  CCG  CCC  GGG  TCT  TCC  CGT
          GCC  CGC  CGG  CGT  GGC  TTC  GGA  AGG  TGA  GGC  GGG  CCC  AGA  AGG  GCA

+1   M    K    Q    L    E    D    K    V    E    E    L    L    S    K    N
     856  ATG  AAA  CAG  CTG  GAA  GAC  AAA  GTA  GAG  GAG  CTC  CTT  AGC  AAG  AAC
          TAC  TTT  GTC  GAC  CTT  CTG  TTT  CAT  CTC  CTC  GAG  GAA  TCG  TTC  TTG

+1   Y    H    L    E    N    E    V    A    R    L    K    K    L    V    G
     901  TAC  CAT  CTA  GAA  AAC  GAG  GTA  GCT  CGT  CTG  AAA  AAG  CTT  GTT  GGT
          ATG  GTA  GAT  CTT  TTG  CTC  CAT  CGA  GCA  GAC  TTT  TTC  GAA  CAA  CCA

Spacer       His-tag
     +1   E    R    G    G    H    H    H    H    H    H    *
     946  GAA  CGT  GGT  GGT  CAC  CAT  CAC  CAT  CAC  CAT  TAA
          CTT  GCA  CCA  CCA  GTG  GTA  GTG  GTA  GTG  GTA  ATT
```

FIG. 28-2

PelB-Leader

```
       M   K   Y   L   L   P   T   A   A   A   G   L   L   L
+1
  1    ATG AAA TAC CTA TTG CCT ACG GCA GCC GCT GGA TTG TTA TTA
       TAC TTT ATG GAT AAC GGA TGC CGT CGG CGA CCT AAC AAT AAT
```

```
                                             VH
       L   A   A   Q   P   A   M   A │ E   V   Q   L   Q   Q
+1
 43    CTC GCG GCC CAG CCG GCC ATG GCC GAG GTT CAG CTT CAG CAG
       GAG CGC CGG GTC GGC CGG TAC CGG CTC CAA GTC GAA GTC GTC
```

```
       S   G   P   E   L   V   K   P   G   A   S   V   K   I
+1
 85    TCT GGA CCT GAG CTG GTG AAG CCC GGG GCC TCA GTG AAG ATT
       AGA CCT GGA CTC GAC CAC TTC GGG CCC CGG AGT CAC TTC TAA
```

```
       S   C   K   A   S   G   Y   A   F   S   S   S   W   M
+1
127    TCC TGC AAA GCT TCT GGC TAC GCA TTC AGT AGC TCT TGG ATG
       AGG ACG TTT CGA AGA CCG ATG CGT AAG TCA TCG AGA ACC TAC
```

```
       N   W   V   K   Q   R   P   G   Q   G   L   E   W   I
+1
169    AAC TGG GTG AAG CAG AGG CCT GGA CAG GGT CTT GAG TGG ATT
       TTG ACC CAC TTC GTC TCC GGA CCT GTC CCA GAA CTC ACC TAA
```

```
       G   R   I   Y   P   G   N   G   D   T   N   Y   N   G
+1
211    GGA CGG ATT TAT CCT GGA AAT GGA GAT ACT AAC TAC AAT GGG
       CCT GCC TAA ATA GGA CCT TTA CCT CTA TGA TTG ATG TTA CCC
```

```
       K   F   K   G   K   A   T   L   T   A   D   K   S   S
+1
253    AAG TTC AAG GGC AAG GCC ACA CTG ACT GCA GAC AAA TCC TCC
       TTC AAG TTC CCG TTC CGG TGT GAC TGA CGT CTG TTT AGG AGG
```

```
       S   T   A   Y   M   Q   L   S   S   L   T   S   V   D
+1
295    AGC ACA GCC TAC ATG CAG CTC AGC AGC CTG ACC TCT GTG GAC
       TCG TGT CGG ATG TAC GTC GAG TCG TCG GAC TGG AGA CAC CTG
```

```
       S   A   V   Y   F   C   A   D   G   N   V   Y   Y   Y
+1
337    TCT GCG GTC TAT TTC TGT GCA GAT GGT AAC GTA TAT TAC TAT
       AGA CGC CAG ATA AAG ACA CGT CTA CCA TTG CAT ATA ATG ATA
```

```
       A   M   D   Y   W   G   Q   G   T   S   V   T   V   S
+1
379    GCT ATG GAC TAC TGG GGT CAA GGA ACC TCA GTC ACC GTC TCC
       CGA TAC CTG ATG ACC CCA GTT CCT TGG AGT CAG TGG CAG AGG
```

```
                  Linker
       S │ G   G   G   G   S   G   G   R   A   S   G   G   G
+1
421    TCA GGT GGA GGC GGT TCA GGT GGG CGC GCC TCT GGC GGT GGC
       AGT CCA CCT CCG CCA AGT CCA CCC GCG CGG AGA CCG CCA CCG
```

```
                     VL
       G   S │ Q   I   V   L   T   Q   S   P   A   S   L   A
+1
463    GGA TCG CAA ATT GTT CTC ACC CAG TCT CCT GCT TCC TTA GCT
       CCT AGC GTT TAA CAA GAG TGG GTC AGA GGA CGA AGG AAT CGA
```

FIG. 29-1

```
     +1   V    S    L    G    Q    R    A    T    I    S    C    R    A    S
    505  GTA  TCT  CTG  GGG  CAG  AGG  GCC  ACC  ATC  TCA  TGC  AGG  GCC  AGC
         CAT  AGA  GAC  CCC  GTC  TCC  CGG  TGG  TAG  AGT  ACG  TCC  CGG  TCG

+1   K    S    V    S    T    S    G    Y    S    Y    M    H    W    Y
    547  AAA  AGT  GTC  AGT  ACA  TCT  GGC  TAT  AGT  TAT  ATG  CAC  TGG  TAC
         TTT  TCA  CAG  TCA  TGT  AGA  CCG  ATA  TCA  ATA  TAC  GTG  ACC  ATG

+1   Q    Q    K    P    G    Q    P    P    K    L    L    I    Y    L
    589  CAA  CAG  AAA  CCA  GGA  CAG  CCA  CCC  AAA  CTC  CTC  ATC  TAT  CTT
         GTT  GTC  TTT  GGT  CCT  GTC  GGT  GGG  TTT  GAG  GAG  TAG  ATA  GAA

+1   A    S    N    L    E    S    G    V    P    A    R    F    S    G
    631  GCA  TCC  AAC  CTA  GAA  TCT  GGG  GTC  CCT  GCC  AGG  TTC  AGT  GGC
         CGT  AGG  TTG  GAT  CTT  AGA  CCC  CAG  GGA  CGG  TCC  AAG  TCA  CCG

+1   S    G    S    G    T    D    F    T    L    N    I    H    P    V
    679  AGT  GGG  TCT  GGG  ACA  GAC  TTC  ACC  CTC  AAC  ATC  CAT  CCT  GTG
         TCA  CCC  AGA  CCC  TGT  CTG  AAG  TGG  GAG  TTG  TAG  GTA  GGA  CAC

+1   E    E    E    D    A    A    T    Y    Y    C    Q    H    S    R
    715  GAG  GAG  GAG  GAT  GCT  GCA  ACC  TAT  TAC  TGT  CAG  CAC  AGT  AGG
         CTC  CTC  CTC  CTA  CGA  CGT  TGG  ATA  ATG  ACA  GTC  GTG  TCA  TCC

+1   E    L    P    R    T    F    G    G    G    T    K    L    E    I
    757  GAG  CTT  CCT  CGG  ACG  TTC  GGT  GGA  GGC  ACC  AAG  CTG  GAA  ATC
         CTC  GAA  GGA  GCC  TGC  AAG  CCA  CCT  CCG  TGG  TTC  GAC  CTT  TAG

|   Spacer        |  Alkaline  phosphatase
     +1   K    R   | A    A    A    A  |  R    A    P    E    M    P    V    L
    799  AAA  CGG | GCG  GCC  GCA  GCC | CGG  GCA  CCA  GAA  ATG  CCT  GTT  CTG
         TTT  GCC | CGC  CGG  CGT  CGG | GCC  CGT  GGT  CTT  TAC  GGA  CAA  GAC +1   E    N    R    A    A    Q    G    D    I    T    A    P    G    G
    841  GAA  AAC  CGG  GCT  GCT  CAG  GGC  GAT  ATT  ACT  GCA  CCC  GGC  GGT
         CTT  TTG  GCC  CGA  CGA  GTC  CCG  CTA  TAA  TGA  CGT  GGG  CCG  CCA +1   A    R    R    L    T    G    D    Q    T    A    A    L    R    D
    883  GCT  CGC  CGT  TTA  ACG  GGT  GAT  CAG  ACT  GCC  GCT  CTG  CGT  GAT
         CGA  GCG  GCA  AAT  TGC  CCA  CTA  GTC  TGA  CGG  CGA  GAC  GCA  CTA +1   S    L    S    D    K    P    A    K    N    I    I    L    L    I
    925  TCT  CTT  AGC  GAT  AAA  CCT  GCA  AAA  AAT  ATT  ATT  TTG  CTG  ATT
         AGA  GAA  TCG  CTA  TTT  GGA  CGT  TTT  TTA  TAA  TAA  AAC  GAC  TAA +1   G    D    G    M    G    D    S    E    I    T    A    A    R    N
    967  GGC  GAT  GGG  ATG  GGG  GAC  TCG  GAA  ATT  ACT  GCC  GCA  CGT  AAT
         CCG  CTA  CCC  TAC  CCC  CTG  AGC  CTT  TAA  TGA  CGG  CGT  GCA  TTA
```

FIG. 29-2

```
      +1   Y    A    E    G    A    G    G    F    F    K    G    I    D    A
     1009  TAT  GCC  GAA  GGT  GCG  GGC  GGC  TTT  TTT  AAA  GGT  ATA  GAT  GCC
           ATA  CGG  CTT  CCA  CGC  CCG  CCG  AAA  AAA  TTT  CCA  TAT  CTA  CGG

+1   L    P    L    T    G    Q    Y    T    H    Y    A    L    N    K
     1051  TTA  CCG  CTT  ACC  GGG  CAA  TAC  ACT  CAC  TAT  GCG  CTG  AAT  AAA
           AAT  GGC  GAA  TGG  CCC  GTT  ATG  TGA  GTG  ATA  CGC  GAC  TTA  TTT

+1   K    T    G    K    P    D    Y    V    T    D    S    A    A    S
     1093  AAA  ACC  GGC  AAA  CCG  GAC  TAC  GTC  ACC  GAC  TCG  GCT  GCA  TCA
           TTT  TGG  CCG  TTT  GGC  CTG  ATG  CAG  TGG  CTG  AGC  CGA  CGT  AGT

+1   A    T    A    W    S    T    G    V    K    T    Y    N    G    A
     1135  GCA  ACC  GCC  TGG  TCA  ACC  GGT  GTC  AAA  ACC  TAT  AAC  GGC  GCG
           CGT  TGG  CGG  ACC  AGT  TGG  CCA  CAG  TTT  TGG  ATA  TTG  CCG  CGC

+1   L    G    V    D    I    H    E    K    D    H    P    T    I    L
     1177  CTG  GGC  GTC  GAT  ATT  CAC  GAA  AAA  GAT  CAC  CCA  ACG  ATT  CTG
           GAC  CCG  CAG  CTA  TAA  GTG  CTT  TTT  CTA  GTG  GGT  TGC  TAA  GAC

+1   E    M    A    K    A    G    L    A    T    G    N    V    S
     1219  GAA  ATG  GCA  AAA  GCC  GCA  GGT  CTG  GCG  ACC  GGT  AAC  GTT  TCT
           CTT  TAC  CGT  TTT  CGG  CGT  CCA  GAC  CGC  TGG  CCA  TTG  CAA  AGA

+1   T    A    E    L    Q    D    A    T    P    A    A    L    V    A
     1261  ACC  GCA  GAG  TTG  CAG  GAT  GCC  ACG  CCC  GCT  GCG  CTG  GTG  GCA
           TGG  CGT  CTC  AAC  GTC  CTA  CGG  TGC  GGG  CGA  CGC  GAC  CAC  CGT

+1   H    V    T    S    R    K    C    Y    G    P    S    A    T    S
     1303  CAT  GTG  ACC  TCG  CGC  AAA  TGC  TAC  GGT  CCG  AGC  GCG  ACC  AGT
           GTA  CAC  TGG  AGC  GCG  TTT  ACG  ATG  CCA  GGC  TCG  CGC  TGG  TCA

+1   E    K    C    P    G    N    A    L    E    K    G    G    K    G
     1345  GAA  AAA  TGT  CCG  GGT  AAC  GCT  CTG  GAA  AAA  GGC  GGA  AAA  GGA
           CTT  TTT  ACA  GGC  CCA  TTG  CGA  GAC  CTT  TTT  CCG  CCT  TTT  CCT

+1   S    I    T    E    Q    L    L    N    A    R    A    D    V    T
     1387  TCG  ATT  ACC  GAA  CAG  CTG  CTT  AAC  GCT  CGT  GCC  GAC  GTT  ACG
           AGC  TAA  TGG  CTT  GTC  GAC  GAA  TTG  CGA  GCA  CGG  CTG  CAA  TGC

+1   L    G    G    G    A    K    T    F    A    E    T    A    T    A
     1429  CTT  GGC  GGC  GGC  GCA  AAA  ACC  TTT  GCT  GAA  ACG  GCA  ACC  GCT
           GAA  CCG  CCG  CCG  CGT  TTT  TGG  AAA  CGA  CTT  TGC  CGT  TGG  CGA

+1   G    E    W    Q    G    K    T    L    R    E    Q    A    Q    A
     1471  GGT  GAA  TGG  CAG  GGA  AAA  ACG  CTG  CGT  GAA  CAG  GCA  CAG  GCG
           CCA  CTT  ACC  GTC  CCT  TTT  TGC  GAC  GCA  CTT  GTC  CGT  GTC  CGC
```

FIG. 29-3

```
     +1   R    G    Y    Q    L    V    S    D    A    A    S    L    N    S
     1513 CGT  GGT  TAT  CAG  TTG  GTG  AGC  GAT  GCT  GCC  TCA  CTG  AAT  TCG
          GCA  CCA  ATA  GTC  AAC  CAC  TCG  CTA  CGA  CGG  AGT  GAC  TTA  AGC

+1   V    T    E    A    N    Q    Q    K    P    L    L    G    L    F
     1555 GTG  ACG  GAA  GCG  AAT  CAG  CAA  AAA  CCC  CTG  CTT  GGC  CTG  TTT
          CAC  TGC  CTT  CGC  TTA  GTC  GTT  TTT  GGG  GAC  GAA  CCG  GAC  AAA

+1   A    D    G    N    M    P    V    R    W    L    G    P    K    A
     1597 GCT  GAC  GGC  AAT  ATG  CCA  GTG  CGC  TGG  CTA  GGA  CCG  AAA  GCA
          CGA  CTG  CCG  TTA  TAC  GGT  CAC  GCG  ACC  GAT  CCT  GGC  TTT  CGT

+1   T    Y    H    G    N    I    D    K    P    A    V    T    C    T
     1639 ACG  TAC  CAT  GGC  AAT  ATC  GAT  AAG  CCC  GCA  GTC  ACC  TGT  ACG
          TGC  ATG  GTA  CCG  TTA  TAG  CTA  TTC  GGG  CGT  CAG  TGG  ACA  TGC

+1   P    N    P    Q    R    N    D    S    V    P    T    L    A    Q
     1681 CCA  AAT  CCG  CAA  CGT  AAT  GAC  AGT  GTA  CCA  ACC  CTG  GCG  CAG
          GGT  TTA  GGC  GTT  GCA  TTA  CTG  TCA  CAT  GGT  TGG  GAC  CGC  GTC

+1   M    T    D    K    A    I    E    L    L    S    K    N    E    K
     1723 ATG  ACC  GAC  AAA  GCC  ATT  GAA  TTG  TTG  AGT  AAA  AAT  GAG  AAA
          TAC  TGG  CTG  TTT  CGG  TAA  CTT  AAC  AAC  TCA  TTT  TTA  CTC  TTT

+1   G    F    F    L    Q    V    E    G    A    S    I    D    K    Q
     1765 GGC  TTT  TTC  CTG  CAA  GTT  GAA  GGT  GCG  TCA  ATC  GAT  AAA  CAG
          CCG  AAA  AAG  GAC  GTT  CAA  CTT  CCA  CGC  AGT  TAG  CTA  TTT  GTC

+1   D    H    A    A    N    P    C    G    Q    I    G    E    T    V
     1807 GAT  CAT  GCT  GCG  AAT  CCT  TGT  GGG  CAA  ATT  GGC  GAG  ACG  GTC
          CTA  GTA  CGA  CGC  TTA  GGA  ACA  CCC  GTT  TAA  CCG  CTC  TGC  CAG

+1   D    L    D    E    A    V    Q    R    A    L    E    F    A    K
     1849 GAT  CTC  GAT  GAA  GCC  GTA  CAA  CGG  GCG  CTG  GAA  TTC  GCT  AAA
          CTA  GAG  CTA  CTT  CGG  CAT  GTT  GCC  CGC  GAC  CTT  AAG  CGA  TTT

+1   K    E    G    N    T    L    V    I    V    T    A    D    H    A
     1891 AAG  GAG  GGT  AAC  ACG  CTG  GTC  ATA  GTC  ACC  GCT  GAT  CAC  GCC
          TTC  CTC  CCA  TTG  TGC  GAC  CAG  TAT  CAG  TGG  CGA  CTA  GTG  CGG

+1   H    A    S    Q    I    V    A    P    D    T    K    A    P    G
     1933 CAC  GCC  AGC  CAG  ATT  GTT  GCG  CCG  GAT  ACC  AAA  GCT  CCG  GGC
          GTG  CGG  TCG  GTC  TAA  CAA  CGC  GGC  CTA  TGG  TTT  CGA  GGC  CCG

+1   L    T    Q    A    L    N    T    K    D    G    A    V    M    V
     1975 CTC  ACC  CAG  GCG  CTA  AAT  ACC  AAA  GAT  GGC  GCA  GTG  ATG  GTG
          GAG  TGG  GTC  CGC  GAT  TTA  TGG  TTT  CTA  CCG  CGT  CAC  TAC  CAC
```

FIG. 29-4

```
      +1   M    S    Y    G    N    S    E    E    D    S    Q    E    H    T
    2017   ATG  AGT  TAC  GGG  AAC  TCC  GAA  GAG  GAT  TCA  CAA  GAA  CAT  ACC
           TAC  TCA  ATG  CCC  TTG  AGG  CTT  CTC  CTA  AGT  GTT  CTT  GTA  TGG

+1   G    S    Q    L    R    I    A    A    Y    G    P    H    A    A
    2059   GGC  AGT  CAG  TTG  CGT  ATT  GCG  GCG  TAT  GGC  CCG  CAT  GCC  GCC
           CCG  TCA  GTC  AAC  GCA  TAA  CGC  CGC  ATA  CCG  GGC  GTA  CGG  CGG

+1   N    V    V    G    L    T    D    Q    T    D    L    F    Y    T
    2101   AAT  GTT  GTT  GGA  CTG  ACC  GAC  CAG  ACC  GAT  CTC  TTC  TAC  ACC
           TTA  CAA  CAA  CCT  GAC  TGG  CTG  GTC  TGG  CTA  GAG  AAG  ATG  TGG

His tag
      +1   M    K    A    A    L    G    D    I    A    H    H    H    H    H
    2143   ATG  AAA  GCC  GCT  CTG  GGG  GAT  ATC  GCA  CAC  CAT  CAC  CAT  CAC
           TAC  TTT  CGG  CGA  GAC  CCC  CTA  TAG  CGT  GTG  GTA  GTG  GTA  GTG

+1   H    *
    2185   CAT  TAA
           GTA  ATT
```

FIG. 29-5

```
       PelB-Leader
 +1    M    K    Y    L    L    P    T    A    A    A    G    L    L    L    L
  1   ATG  AAA  TAC  CTA  TTG  CCT  ACG  GCA  GCC  GCT  GGA  TTG  TTA  TTA  CTC
      TAC  TTT  ATG  GAT  AAC  GGA  TGC  CGT  CGG  CGA  CCT  AAC  AAT  AAT  GAG

| VH
 +1    A    A    Q    P    A    M    A  | E    V    Q    L    Q    Q    S    G
 46   GCG  GCC  CAG  CCG  GCC  ATG  GCG |GAG  GTT  CAG  CTT  CAG  CAG  TCT  GGA
      CGC  CGG  GTC  GGC  CGG  TAC  CGC |CTC  CAA  GTC  GAA  GTC  GTC  AGA  CCT

+1    P    E    L    V    K    P    G    A    S    V    K    I    S    C    K
 91   CCT  GAG  CTG  GTG  AAG  CCC  GGG  GCC  TCA  GTG  AAG  ATT  TCC  TGC  AAA
      GGA  CTC  GAC  CAC  TTC  GGG  CCC  CGG  AGT  CAC  TTC  TAA  AGG  ACG  TTT

+1    A    S    G    Y    A    F    S    S    S    W    M    N    W    V    K
136   GCT  TCT  GGC  TAC  GCA  TTC  AGT  AGC  TCT  TGG  ATG  AAC  TGG  GTG  AAG
      CGA  AGA  CCG  ATG  CGT  AAG  TCA  TCG  AGA  ACC  TAC  TTG  ACC  CAC  TTC

+1    Q    R    P    G    Q    G    L    E    W    I    G    R    I    Y    P
181   CAG  AGG  CCT  GGA  CAG  GGT  CTT  GAG  TGG  ATT  GGA  CGG  ATT  TAT  CCT
      GTC  TCC  GGA  CCT  GTC  CCA  GAA  CTC  ACC  TAA  CCT  GCC  TAA  ATA  GGA

+1    G    N    G    D    T    N    Y    N    G    K    F    K    G    K    A
226   GGA  AAT  GGA  GAT  ACT  AAC  TAC  AAT  GGG  AAG  TTC  AAG  GGC  AAG  GCC
      CCT  TTA  CCT  CTA  TGA  TTG  ATG  TTA  CCC  TTC  AAG  TTC  CCG  TTC  CGG

+1    T    L    T    A    D    K    S    S    S    T    A    Y    M    Q    L
271   ACA  CTG  ACT  GCA  GAC  AAA  TCC  TCC  AGC  ACA  GCC  TAC  ATG  CAG  CTC
      TGT  GAC  TGA  CGT  CTG  TTT  AGG  AGG  TCG  TGT  CGG  ATG  TAC  GTC  GAG

+1    S    S    L    T    S    V    D    S    A    V    Y    F    C    A    D
316   AGC  AGC  CTG  ACC  TCT  GTG  GAC  TCT  GCG  GTC  TAT  TTC  TGT  GCA  GAT
      TCG  TCG  GAC  TGG  AGA  CAC  CTG  AGA  CGC  CAG  ATA  AAG  ACA  CGT  CTA

+1    G    N    V    Y    Y    Y    A    M    D    Y    W    G    Q    G    T
361   GGT  AAC  GTA  TAT  TAC  TAT  GCT  ATG  GAC  TAC  TGG  GGT  CAA  GGA  ACC
      CCA  TTG  CAT  ATA  ATG  ATA  CGA  TAC  CTG  ATG  ACC  CCA  GTT  CCT  TGG

| Linker
 +1    S    V    T    V    S    S  | G    G    G    G    S    G    G    R    A
406   TCA  GTC  ACC  GTC  TCC  TCA |GGT  GGA  GGC  GGT  TCA  GGT  GGG  CGC  GCC
      AGT  CAG  TGG  CAG  AGG  AGT |CCA  CCT  CCG  CCA  AGT  CCA  CCC  GCG  CGG
```

FIG. 30-1

```
                                                   | VL
    +1   S   G   G   G   G   S   | Q   I   V   L   T   Q   S   P   A
   451   TCT GGC GGT GGC GGA TCG | CAA ATT GTT CTC ACC CAG TCT CCT GCT
         AGA CCG CCA CCG CCT AGC | GTT TAA CAA GAG TGG GTC AGA GGA CGA

+1   S   L   A   V   S   L   G   Q   R   A   T   I   S   C   R
   496   TCC TTA GCT GTA TCT CTG GGG CAG AGG GCC ACC ATC TCA TGC AGG
         AGG AAT CGA CAT AGA GAC CCC GTC TCC CGG TGG TAG AGT ACG TCC

+1   A   S   K   S   V   S   T   S   G   Y   S   Y   M   H   W
   541   GCC AGC AAA AGT GTC AGT ACA TCT GGC TAT AGT TAT ATG CAC TGG
         CGG TCG TTT TCA CAG TCA TGT AGA CCG ATA TCA ATA TAC GTG ACC

+1   Y   Q   Q   K   P   G   Q   P   P   K   L   L   I   Y   L
   586   TAC CAA CAG AAA CCA GGA CAG CCA CCC AAA CTC CTC ATC TAT CTT
         ATG GTT GTC TTT GGT CCT GTC GGT GGG TTT GAG GAG TAG ATA GAA

+1   A   S   N   L   E   S   G   V   P   A   R   F   S   G   S
   631   GCA TCC AAC CTA GAA TCT GGG GTC CCT GCC AGG TTC AGT GGC AGT
         CGT AGG TTG GAT CTT AGA CCC CAG GGA CGG TCC AAG TCA CCG TCA

+1   G   S   G   T   D   F   T   L   N   I   H   P   V   E   E
   676   GGG TCT GGG ACA GAC TTC ACC CTC AAC ATC CAT CCT GTG GAG GAG
         CCC AGA CCC TGT CTG AAG TGG GAG TTG TAG GTA GGA CAC CTC CTC

+1   E   D   A   A   T   Y   Y   C   Q   H   S   R   E   L   P
   721   GAG GAT GCT GCA ACC TAT TAC TGT CAG CAC AGT AGG GAG CTT CCT
         CTC CTA CGA CGT TGG ATA ATG ACA GTC GTG TCA TCC CTC GAA GGA

| Spacer
    +1   R   T   F   G   G   G   T   K   L   E   I   K   R | A   A
   766   CGG ACG TTC GGT GGA GGC ACC AAG CTG GAA ATC AAA CGG| GCG GCC
         GCC TGC AAG CCA CCT CCG TGG TTC GAC CTT TAG TTT GCC| CGC CGG

| Hinge                                  | Helix
    +1   A    | P   K   P   S   T   P   P   G   S   S  | R   M   K   Q
   811   GCA  | CCG AAG CCT TCC ACT CCG CCC GGG TCT TCC| CGT ATG AAA CAG
         CGT  | GGC TTC GGA AGG TGA GGC GGG CCC AGA AGG| GCA TAC TTT GTC +1   L   E   D   K   V   E   E   L   L   S   K   N   Y   H   L
   856   CTG GAA GAC AAA GTA GAG GAG CTC CTT AGC AAG AAC TAC CAT CTA
         GAC CTT CTG TTT CAT CTC CTC GAG GAA TCG TTC TTG ATG GTA GAT +1   E   N   E   V   A   R   L   K   K   L   V   G   E   R   | G
   901   GAA AAC GAG GTA GCT CGT CTG AAA AAG CTT GTT GGT GAA CGT  | GGT
         CTT TTG CTC CAT CGA GCA GAC TTT TTC GAA CAA CCA CTT GCA  | CCA
```

FIG. 30-2

```
Spacer  | His-tag
   +1 G | H   H   H   H   H   H   *
  946 GGT|CAC CAT CAC CAT CAC CAT TAA
      CCA|GTG GTA GTG GTA GTG GTA ATT
```

FIG. 30-3

```
                                              HindIII
2206   CAG GAA ACA GCT ATG ACC ATG ATT ACG CCA AGC TTC CAT GAA AAT
       GTC CTT TGT CGA TAC TGG TAC TAA TGC GGT TCG AAG GTA CTT TTA PelB-Leader
                              M   K   Y   L   L   P   T
2251   TCT ATT TCA AGG AGA CAG TCA TAA TGA AAT ACC TAT TGC CTA CGG
       AGA TAA AGT TCC TCT GTC AGT ATT ACT TTA TGG ATA ACG GAT GCC A   A   A   G   L   L   L   L   A   A   Q   P   A   M   A
                                                SfiI
2296   CAG CCG CTG GAT TGT TAT TAC TCG CGG CCC AGC CGG CCA TGG CCC
       GTC GGC GAC CTA ACA ATA ATG AGC GCC GGG TCG GCC GGT ACC GGG Polylinker
        Q   V   Q   L   Q   A   R   L   Q   V   D   L   E   I   K
                                AscI
2341   AGG TGC AGC TGC AGG CGC GCC TGC AGG TCG ACC TCG AGA TCA AAC
       TCC ACG TCG ACG TCC GCG CGG ACG TCC AGC TGG AGC TCT AGT TTG

| Spacer  |   Myc-tag
        R | A  A  A | E   Q   K   L   I   S   E   E   D   L   N
          | NotI
2386   GGG CGG CCG CAG AAC AAA AAC TCA TCT CAG AAG AGG ATC TGA ATG
       CCC GCC GGC GTC TTG TTT TTG AGT AGA GTC TTC TCC TAG ACT TAC

|Spacer| His tag
        G | A  A | H   H   H   H   H   H   *   *
          |      |                               EcoRI
2431   GGG CGG CAC ATC ACC ATC ACC ATC ACT AAT AAG AAT TCA CTG GCC
       CCC GCC GTG TAG TGG TAG TGG TAG TGA TTA TTC TTA AGT GAC CGG
```

FIG. 33

```
      PelB-leader
+1   M   K   Y   L   L   P   T   A   A   A   G   L   L   L   L
 1   ATG AAA TAC CTA TTG CCT ACG GCA GCC GCT GGA TTG TTA TTA CTC
     TAC TTT ATG GAT AAC GGA TGC CGT CGG CGA CCT AAC AAT AAT GAG VH
+1   A   A   Q   P   A   M   A | E   V   K   L   V   E   S   G
46   GCG GCC CAG CCG GCC ATG GCC|GAG GTG AAG CTG GTG GAG TCT GGG
     CGC CGG GTC GGC CGG TAC CGG|CTC CAC TTC GAC CAC CTC AGA CCC +1   G   G   L   V   K   P   G   G   S   L   K   L   S   C   A
91   GGA GGC TTA GTG AAG CCT GGA GGG TCC CTG AAA CTC TCC TGT GCA
     CCT CCG AAT CAC TTC GGA CCT CCC AGG GAC TTT GAG AGG ACA CGT +1   A   S   G   F   T   F   S   S   Y   T   M   S   W   V   R
136  GCC TCT GGA TTC ACT TTC AGT AGC TAT ACC ATG TCT TGG GTT CGC
     CGG AGA CCT AAG TGA AAG TCA TCG ATA TGG TAC AGA ACC CAA GCG +1   Q   T   P   E   K   R   L   E   W   V   A   T   I   S   S
181  CAG ACT CCG GAG AAG AGG CTG GAG TGG GTC GCA ACC ATT AGT AGT
     GTC TGA GGC CTC TTC TCC GAC CTC ACC CAG CGT TGG TAA TCA TCA +1   G   G   S   S   T   Y   Y   P   D   S   V   K   G   R   F
226  GGN GGT AGT TCC ACC TAC TAT CCA GAC AGT GTG AAG GGC CGA TTC
     CCN CCA TCA AGG TGG ATG ATA GGT CTG TCA CAC TTC CCG GCT AAG +1   T   I   S   R   D   N   A   K   N   T   L   Y   L   Q   M
271  ACC ATC TCC AGA GAC AAT GCC AAG AAC ACC CTG TAC CTG CAA ATG
     TGG|TAG AGG TCT|CTG TTA CGG TTC TTG TGG GAC ATG GAC GTT TAC +1   S | S   L   R | S   E   D   T   A   M   Y   Y   C   T   R
316  AGC|AGT CTG AGG|TCT GAG GAC ACA GCC ATG TAT TAC TGT ACA AGA
     TCG TCA GAC TCC AGA CTC CTG TGT CGG TAC ATA ATG ACA TGT TCT +1   E   G   G   F   T   V   N   W   Y   F   D   V   W   G
361  GAG GGG GGT GGT TTC ACC GTC AAC TGG TAC TTC GAT GTC TGG GGC
     CTC CCC CCA CCA AAG TGG CAG TTG ACC ATG AAG CTA CAG ACC CCG Leader
+1   A   G   T   S   V   T   V   S   S | G   G   G   G   S   G
406  GCA GGA ACC TCA GTC ACC GTC TCC TCA|GGT GGA GGC GGT TCA GGT
     CGT CCT TGG AGT CAG TGG CAG AGG AGT|CCA CCT CCG CCA AGT CCA
```

FIG. 34-1

```
                                                              VK
     +1   G    R    A    S    G    G    G    G    S  | D    I    V    L    T    Q
    451  GGG  CGC  GCC  TCT  GGC  GGT  GGC  GGA  TCG   GAC  ATT  GTG  CTG  ACA  CAG
         CCC  GCG  CGG  AGA  CCG  CCA  CCG  CCT  AGC   CTG  TAA  CAC  GAC  TGT  GTC

+1   S    P    A    S    L    A    V    S    L    G    Q    R    A    T    I
    496  TCT  CCA  GCT  TCT  TTG  GCT  GTG  TCT  CTA  GGG  CAG  AGG  GCC  ACC  ATA
         AGA  GGT  CGA  AGA  AAC  CGA  CAC  AGA  GAT  CCC  GTC  TCC  CGG  TGG  TAT

+1   S    C    R    A    S    E    S    V    D    S    Y    G    Y    N    F
    541  TCC  TGC  AGA  GCC  AGT  GAA  AGT  GTT  GAT  AGT  TAT  GGC  TAT  AAT  TTT
         AGG  ACG  TCT  CGG  TCA  CTT  TCA  CAA  CTA  TCA  ATA  CCG  ATA  TTA  AAA

+1   M    H    W    Y    Q    Q    I    P    G    Q    P    P    K    L    L
    586  ATG  CAC  TGG  TAT  CAG  CAG  ATA  CCA  GGA  CAG  CCA  CCC  AAA  CTC  CTC
         TAC  GTG  ACC  ATA  GTC  GTC  TAT  GGT  CCT  GTC  GGT  GGG  TTT  GAG  GAG

+1   I    Y    R    A    S    N    L    E    S    G    I    P    A    R    F
    631  ATC  TAT  CGT  GCA  TCC  AAC  CTA  GAG  TCT  GGG  ATC  CCT  GCC  AGG  TTC
         TAG  ATA  GCA  CGT  AGG  TTG  GAT  CTC  AGA  CCC  TAG  GGA  CGG  TCC  AAG

+1   S    G    S    G    S    R    T    D    F    T    L    T    I    N    P
    676  AGT  GGC  AGT  GGG  TCT  AGG  ACA  GAC  TTC  ACC  CTC  ACC  ATT  AAT  CCT
         TCA  CCG  TCA  CCC  AGA  TCC  TGT  CTG  AAG  TGG  GAG  TGG  TAA  TTA  GGA

+1   V    E    A    D    D    V    A    T    Y    Y    C    Q    Q    S    N
    721  GTG  GAG  GCT  GAT  GAT  GTT  GCA  ACC  TAT  TAC  TGT  CAG  CAA  AGT  AAT
         CAC  CTC  CGA  CTA  CTA  CAA  CGT  TGG  ATA  ATG  ACA  GTC  GTT  TCA  TTA

+1   E    D    P    L    T    F    G    T    G    T    R    L    E    I    K
    766  GAG  GAT  CCG  CTC  ACG  TTC  GGT  ACT  GGG  ACC  AGA  CTG  GAA  ATA  AAA
         CTC  CTA  GGC  GAG  TGC  AAG  CCA  TGA  CCC  TGG  TCT  GAC  CTT  TAT  TTT

Spacer         Myc-tag
     +1   R  | A    A    A  | E    Q    K    L    I    S    E    E    D    L    N
    811  CGG  GCG  GCC  GCA  GAA  CAA  AAA  CTC  ATC  TCA  GAA  GAG  GAT  CTG  AAT
         GCC  CGC  CGG  CGT  CTT  GTT  TTT  GAG  TAG  AGT  CTT  CTC  CTA  GAC  TTA Spacer   His tag
     +1   G  | A    A | H    H    H    H    H    H    *    *
    856  GGG  GCG  GCA  CAT  CAC  CAT  CAC  CAT  CAC  TAA  TAA
         CCC  CGC  CGT  GTA  GTG  GTA  GTG  GTA  GTG  ATT  ATT
```

FIG. 34-2

```
         Pel-leader
     +1  M   K   Y   L   L   P   T   A   A   A   G   L   L   L   L
      1  ATG AAA TAC CTA TTG CCT ACG GCA GCC GCT GGA TTG TTA TTA CTC
         TAC TTT ATG GAT AAC GGA TGC CGT CGG CGA CCT AAC AAT AAT GAG

|VH
     +1  A   A   Q   P   A   M   A  |E   V   Q   L   Q   Q   S   G
     46  GCG GCC CAG CCG GCC ATG GCC GAG GTT CAG CTT CAG CAG TCT GGA
         CGC CGG GTC GGC CGG TAC CGG CTC CAA GTC GAA GTC GTC AGA CCT

+1  P   E   L   V   K   P   G   A   S   V   K   I   S   C   K
     91  CCT GAG CTG GTG AAG CCC GGG GCC TCA GTG AAG ATT TCC TGC AAA
         GGA CTC GAC CAC TTC GGG CCC CGG AGT CAC TTC TAA AGG ACG TTT

+1  A   S   G   Y   A   F   S   S   S   W   M   N   W   V   K
    136  GCT TCT GGC TAC GCA TTC AGT AGC TCT TGG ATG AAC TGG GTG AAG
         CGA AGA CCG ATG CGT AAG TCA TCG AGA ACC TAC TTG ACC CAC TTC

+1  Q   R   P   G   Q   G   L   E   W   I   G   R   I   Y   P
    181  CAG AGG CCT GGA CAG GGT CTT GAG TGG ATT GGA CGG ATT TAT CCT
         GTC TCC GGA CCT GTC CCA GAA CTC ACC TAA CCT GCC TAA ATA GGA

+1  G   N   G   D   T   N   Y   N   G   K   F   K   G   K   A
    226  GGA AAT GGA GAT ACT AAC TAC AAT GGG AAG TTC AAG GGC AAG GCC
         CCT TTA CCT CTA TGA TTG ATG TTA CCC TTC AAG TTC CCG TTC CGG

+1  T   L   T   A   D   K   S   S   S   T   A   Y   M   Q   L
    271  ACA CTG ACT GCA GAC AAA TCC TCC AGC ACA GCC TAC ATG CAG CTC
         TGT GAC TGA CGT CTG TTT AGG AGG TCG TGT CGG ATG TAC GTC GAG

+1  S   S   L   T   S   V   D   S   A   V   Y   F   C   A   D
    316  AGC AGC CTG ACC TCT GTG GAC TCT GCG GTC TAT TTC TGT GCA GAT
         TCG TCG GAC TGG AGA CAC CTG AGA CGC CAG ATA AAG ACA CGT CTA

+1  G   N   V   Y   Y   Y   A   M   D   Y   W   G   Q   G   T
    361  GGT AAC GTA TAT TAC TAT GCT ATG GAC TAC TGG GGT CAA GGA ACC
         CCA TTG CAT ATA ATG ATA CGA TAC CTG ATG ACC CCA GTT CCT TGG

|Leader
     +1  S   V   T   V   S   S  |G   G   G   G   S   G   G   R   A
    406  TCA GTC ACC GTC TCC TCA GGT GGA GGC GGT TCA GGT GGG CGC GCC
         AGT CAG TGG CAG AGG AGT CCA CCT CCG CCA AGT CCA CCC GCG CGG

|VL
     +1  S   G   G   G   G   S  |Q   I   V   L   T   Q   S   P   A
    451  TCT GGC GGT GGC GGA TCG CAA ATT GTT CTC ACC CAG TCT CCT GCT
         AGA CCG CCA CCG CCT AGC GTT TAA CAA GAG TGG GTC AGA GGA CGA
```

FIG. 35-1

```
    +1   S    L    A    V    S    L    G    Q    R    A    T    I    S    C    R
   496  TCC  TTA  GCT  GTA  TCT  CTG  GGG  CAG  AGG  GCC  ACC  ATC  TCA  TGC  AGG
        AGG  AAT  CGA  CAT  AGA  GAC  CCC  GTC  TCC  CGG  TGG  TAG  AGT  ACG  TCC

+1   A    S    K    S    V    S    T    S    G    Y    S    Y    M    H    W
   541  GCC  AGC  AAA  AGT  GTC  AGT  ACA  TCT  GGC  TAT  AGT  TAT  ATG  CAC  TGG
        CGG  TCG  TTT  TCA  CAG  TCA  TGT  AGA  CCG  ATA  TCA  ATA  TAC  GTG  ACC

+1   Y    Q    Q    K    P    G    Q    P    P    K    L    L    I    Y    L
   586  TAC  CAA  CAG  AAA  CCA  GGA  CAG  CCA  CCC  AAA  CTC  CTC  ATC  TAT  CTT
        ATG  GTT  GTC  TTT  GGT  CCT  GTC  GGT  GGG  TTT  GAG  GAG  TAG  ATA  GAA

+1   A    S    N    L    E    S    G    V    P    A    R    F    S    G    S
   631  GCA  TCC  AAC  CTA  GAA  TCT  GGG  GTC  CCT  GCC  AGG  TTC  AGT  GGC  AGT
        CGT  AGG  TTG  GAT  CTT  AGA  CCC  CAG  GGA  CGG  TCC  AAG  TCA  CCG  TCA

+1   G    S    G    T    D    F    T    L    N    I    H    P    V    E    E
   676  GGG  TCT  GGG  ACA  GAC  TTC  ACC  CTC  AAC  ATC  CAT  CCT  GTG  GAG  GAG
        CCC  AGA  CCC  TGT  CTG  AAG  TGG  GAG  TTG  TAG  GTA  GGA  CAC  CTC  CTC

+1   E    D    A    A    T    Y    Y    C    Q    H    S    R    E    L    P
   721  GAG  GAT  GCT  GCA  ACC  TAT  TAC  TGT  CAG  CAC  AGT  AGG  GAG  CTT  CCT
        CTC  CTA  CGA  CGT  TGG  ATA  ATG  ACA  GTC  GTG  TCA  TCC  CTC  GAA  GGA

Spacer
    +1   R    T    F    G    G    G    T    K    L    E    I    K    R |  A    A
   766  CGG  ACG  TTC  GGT  GGA  GGC  ACC  AAG  CTG  GAA  ATC  AAA  CGG| GGG  GCC
        GCC  TGC  AAG  CCA  CCT  CCG  TGG  TTC  GAC  CTT  TAG  TTT  GCC| CGC  CGG Myc-tag                                              Spacer
    +1   A |  E    Q    K    L    I    S    E    E    D    L    N    G | A    A
   811  GCA| GAA  CAA  AAA  CTC  ATC  TCA  GAA  GAG  GAT  CTG  AAT  GGG| GCG  GCA
        CGT| CTT  GTT  TTT  GAG  TAG  AGT  CTT  CTC  CTA  GAC  TTA  CCC| CGC  CGT His tag
    +1   H    H    H    H    H    H    *
   856  CAT  CAC  CAT  CAC  CAT  CAC  TAA
        GTA  GTG  GTA  GTG  GTA  GTG  ATT
```

FIG. 35-2

FACTOR IX/FACTOR IXA ACTIVATING ANTIBODIES AND ANTIBODY DERIVATIVES

The present invention relates to actor IX/factor IXa-antibodies and antibody derivatives.

Blood clots (thrombi) are formed by a series of zymogen activations referred to as the coagulation cascade. In the course of this enzymatic cascade, the activated form of each of such zymogens (referred to as factors) catalyzes the activation of the next one. Thrombi are deposits of blood components on the surface of a blood vessel wall and mainly consist of aggregated blood platelets and insoluble, cross-linked fibrin. Fibrin formation is effected by means of thrombin by limited proteolysis of fibrinogen. Thrombin is the final product of the coagulation cascade, (K. G. Mann, Blood, 1990, Vol. 76, pp. 1–16).

Activation of factor x by the complex of activated factor IX (FIXa) and activated factor VIII (FVIIIa) is a key step in coagulation. The absence of the components of this complex or a disturbance of their function is associated with the blood coagulation disorder called hemophilia (J. E. Sadler & E. W. Davie: Hemophilia A, Hemophilia B and von Willebrand's disease, in G. Stamatoyannopoulos et al. (Eds.): The molecular basis of blood diseases. W. B. Saunders Co., Philadelphia, 1987, pp. 576–602). Hemophilia A denotes a (functional) absence of factor VIII activity, while Hemophilia B is characterized by the absence of factor IX activity. At present, treatment of Hemophilia A is effected via a substitution therapy by administering factor VIII concentrates. However, approximately 20–30% of Hemophilia A patients develop factor VIII inhibitors (i.e. antibodies against factor VIII), whereby the effect of administered factor VIII preparations is inhibited. Treatment of factor VIII inhibitor patients is very difficult and involves risks, and so far there exist only a limited number of treatments for these patients.

In the case of patients having a low FVIII inhibitor level, it is possible, though expensive, to administer high doses of factor VIII to such patients and thus to neutralize the antibodies against factor VIII. The amount of factor VIII beyond that needed to neutralize the inhibitor antibodies then has hemostatic action. In many cases, desensitization can be effected, whereupon it is then possible again to apply standard factor VIII treatments. Such high dose factor VIII treatments require, however, large amounts of factor VIII, are time-consuming and may involve severe anaphylactic side reactions. Alternatively, the treatment may be carried out with porcine factor VIII molecules.

A further high-cost method involves removing factor VIII inhibitors through extra corporeal immunoadsorption on lectins which bind to immunoglobulins (protein A, protein G) or to immobilized factor VIII. Since the patient must be connected to an apheresis machine during this treatment, the treatment also constitutes a great burden on the patient. It is also not possible to treat an acute hemorrhage in this way.

At present, the therapy of choice is to administer activated prothrombin complex concentrates (APCC), such as FEIBA® and AUTOPLEX®, which are suitable for the treatment of acute hemorrhages even in patients having a high inhibitor titer (DE 31 27 318).

In the intravascular system of blood coagulation, the last step is the activation of factor X. This reaction is stimulated by the binding of factor VIIIa to factor IXa and the formation of a "tenase"-complex consisting of the factors IXa, VIIIa, X and phospholipid. Without the binding of FVIIIa, FIXa exhibits no or only a very slight enzymatic activity relative to FX.

Over the last several years, a number of possible binding sites for factor VIIIa to factor IXa have been characterized, and it has been shown that antibodies or peptides which bind to these regions inhibit the activity of FIXa (Fay et al., J. Biol. Chem., 1994, Vol. 269, pp. 20522–20527, Lenting et al., J. Biol. Chem., 1996, Vol. 271, pp. 1935–1940, Jorquera et al., Circulation, 1992, Vol. 86, Abstract 2725). The inhibition of coagulation factors, such as factor IX, has also been achieved through the use of monoclonal antibodies with the aim of preventing thrombosis formation (WO 97/26010).

The opposite effect, i.e. an increase in the factor IXa mediated activation of factor X, has been described by Liles D. K. et al., (Blood, 1997, Vol. 90, suppl. 1, 2054) through the binding of a factor VIII peptide (amino acids 698–712) to factor IX. Yet, this effect only occurs in the absence of factor VIIIa, while in the presence of factor VIIIa the factor IXa/factor VIIIa-mediated cleavage of factor X is inhibited by this peptide.

SUMMARY OF THE INVENTION

With a view to the possible risks and side effects which may occur in the treatment of hemophilia patients, there is a need for a therapy which allows for the effective treatment of FVIII inhibitor patients. Therefore, it is an object of the present invention to provide a preparation for the treatment of blood coagulation disorders which has particular advantages for factor VIII inhibitor patients.

According to the present invention, this object is achieved through the use of antibodies or antibody derivatives against factor IX/factor IXa which have factor VIIIa-cofactor activity or factor IXa-activating activity and lead to an increase in the procoagulant activity of factor IXa. Surprisingly, the action of these inventive factor IX/factor IXa-activating antibodies and antibody derivatives is not negatively affected by the presence of inhibitors, such as inhibitors against factor VIII/factor VIIIa, but instead the procoagulant activity of factor IXa in this case also is increased.

A further advantage of this invention is that the administration of the preparation according to the invention allows for rapid blood coagulation even in the absence of factor VIII or factor VIIIa, even in the case of FVIII inhibitor patients. Surprisingly, these agents are also effective in the presence of factor VIIIa.

The antibodies and antibody derivatives according to the present invention thus have a FVIII-cofactor-like activity which, in a FVIII assay (e.g. a COATEST® assay or Immunochrom test) after 2 hours of incubation exhibits a ratio of background (basic noise) to measured value of at least 3. Calculation of this ratio may, e.g., be effected according to the following scheme:

$$\frac{\text{Antibody measurement (OD 405)} - \text{blank value from reagent}}{\text{Mouse-IgG-measurement (OD 405)} - \text{blank value from reagent}} \geq 3$$

after two hours of incubation.

The antibodies according to the invention preferably have an in vivo half life of at least 5 days, more preferably at least 10 days, though it is more preferred to have a half life of at least 20 days.

A further aspect of this invention is a preparation comprising antibodies and/or antibody derivatives against factor IX/factor IXa and a pharmaceutically acceptable carrier substance. Furthermore, the preparation according to the invention may additionally comprise factor IX and/or factor IXa.

A further aspect of the invention is the use of the antibodies or antibody derivatives to increase the amidolytic activity of factor IXa.

FIG. 12 shows the primer sequences (SEQ ID NOS:50–61) for the amplification of the genes of the variable heavy chain of mouse antibody.

FIG. 13 shows the primer sequences (SEQ ID NOS:65–78) for the amplification of the genes of the variable light (kappa) chain of the mouse antibody.

FIG. 14 shows the DNA and derived protein sequence of the scFv from hybridoma cell line 193/AD3 (SEQ.ID.NOs. 81 and 82).

FIG. 15 shows the DNA and derived protein sequence of the scFv from hybridoma cell line 193/K2 (SEQ.ID.NOs. 83 and 84).

FIG. 16 shows the DNA and derived protein sequence of the scFv from hybridoma cell line 198/AB2 (subclone of 198/B1) (SEQ.ID.NOs. 85 and 86).

FIG. 17 shows the DNA and deduced protein sequence of scFv derived from the cell line 198/A1 (SEQ.ID.NOs. 87 and 88).

Figure 18:
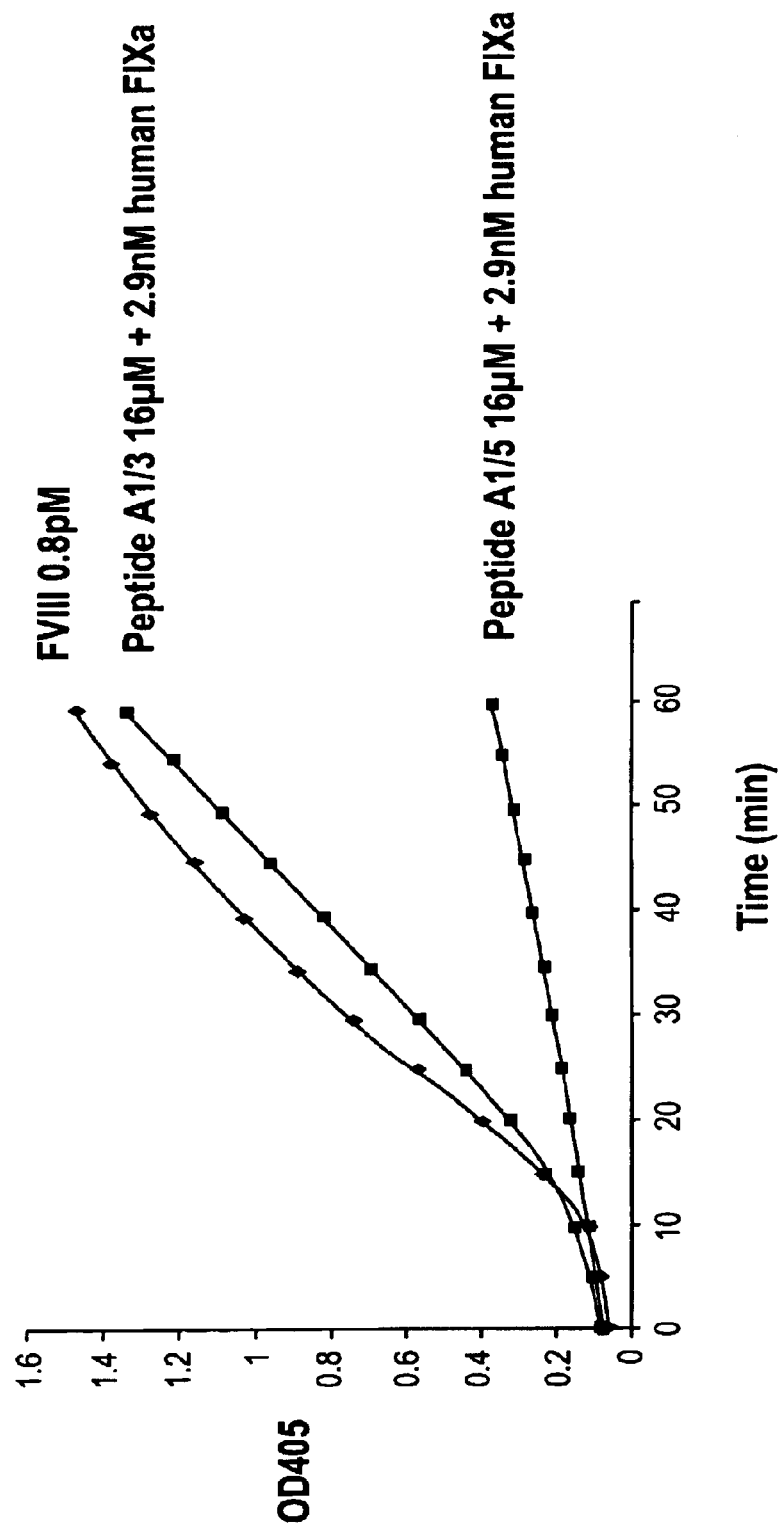

FIG. 18 demonstrates the chromogenic FVIII-like activity of peptide A1/3 in the presence of 2.9 nM human FIXa. The scrambled version of peptide A1/3, peptide A1/5 does not give rise to any FXa generation.

Figure 19:
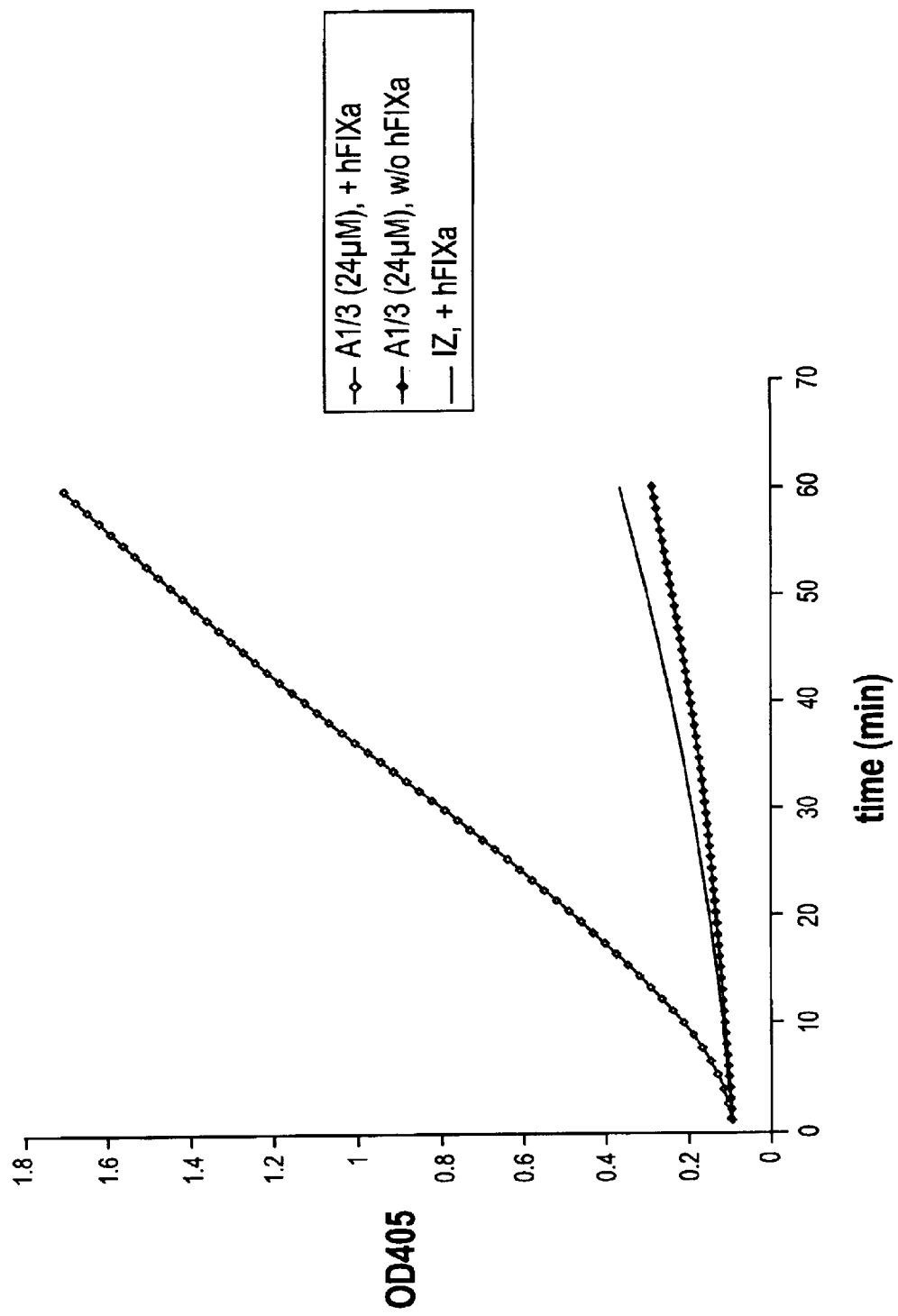

FIG. 19 demonstrates the dependence of the chromogenic FVIII-like activity of peptide A1/3 on the presence of human FIXa. In the absence of human FIXa, peptide A1/3 does not give rise to any FXa generation. The buffer control, plain imidazole buffer is designated IZ.

Figure 20:
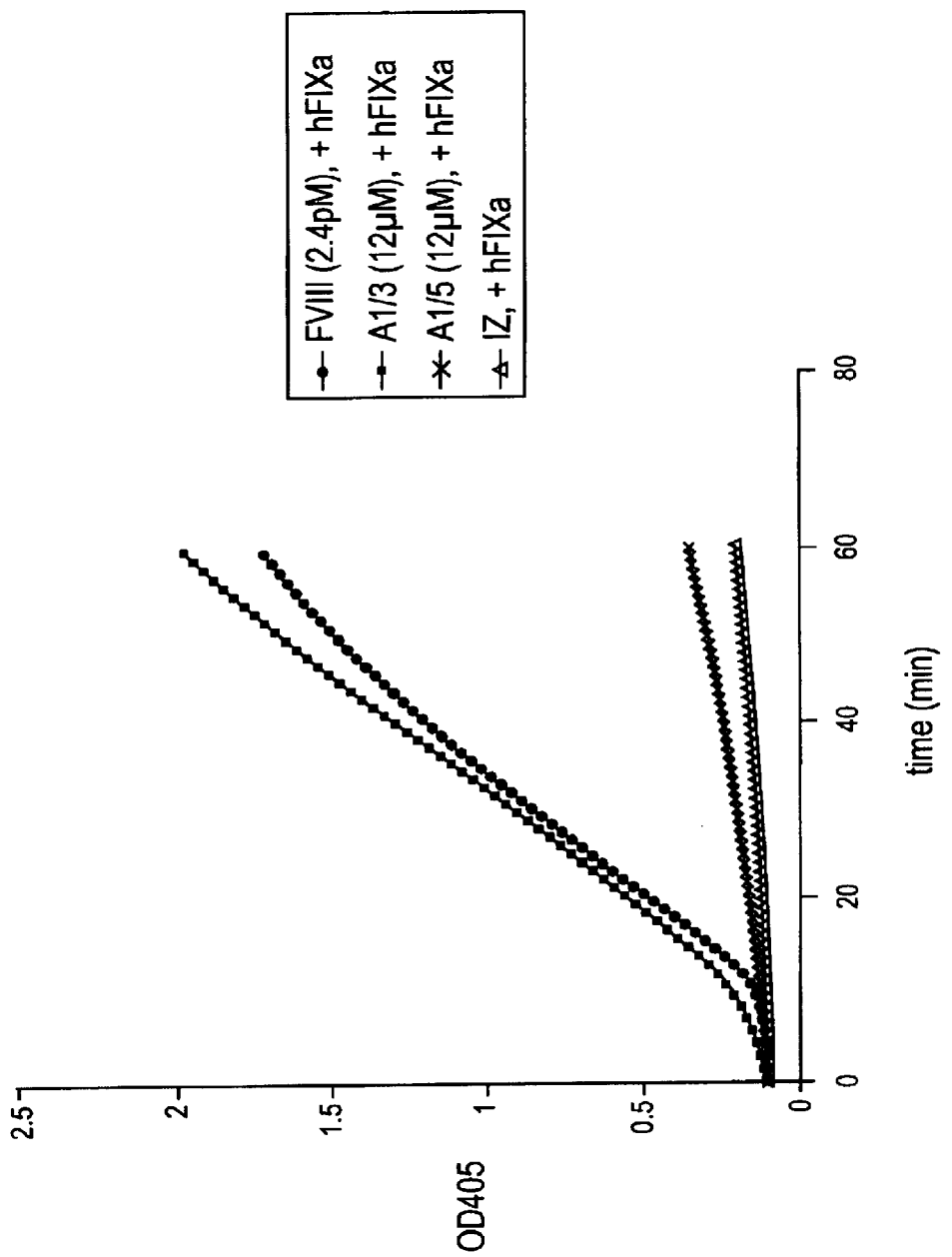

FIG. 20 shows that the chirality of Arg-residues does not play a significant role for the chromogenic activity of peptides A1/3-rd and A1/3-Rd-srmb.

Figure 21:
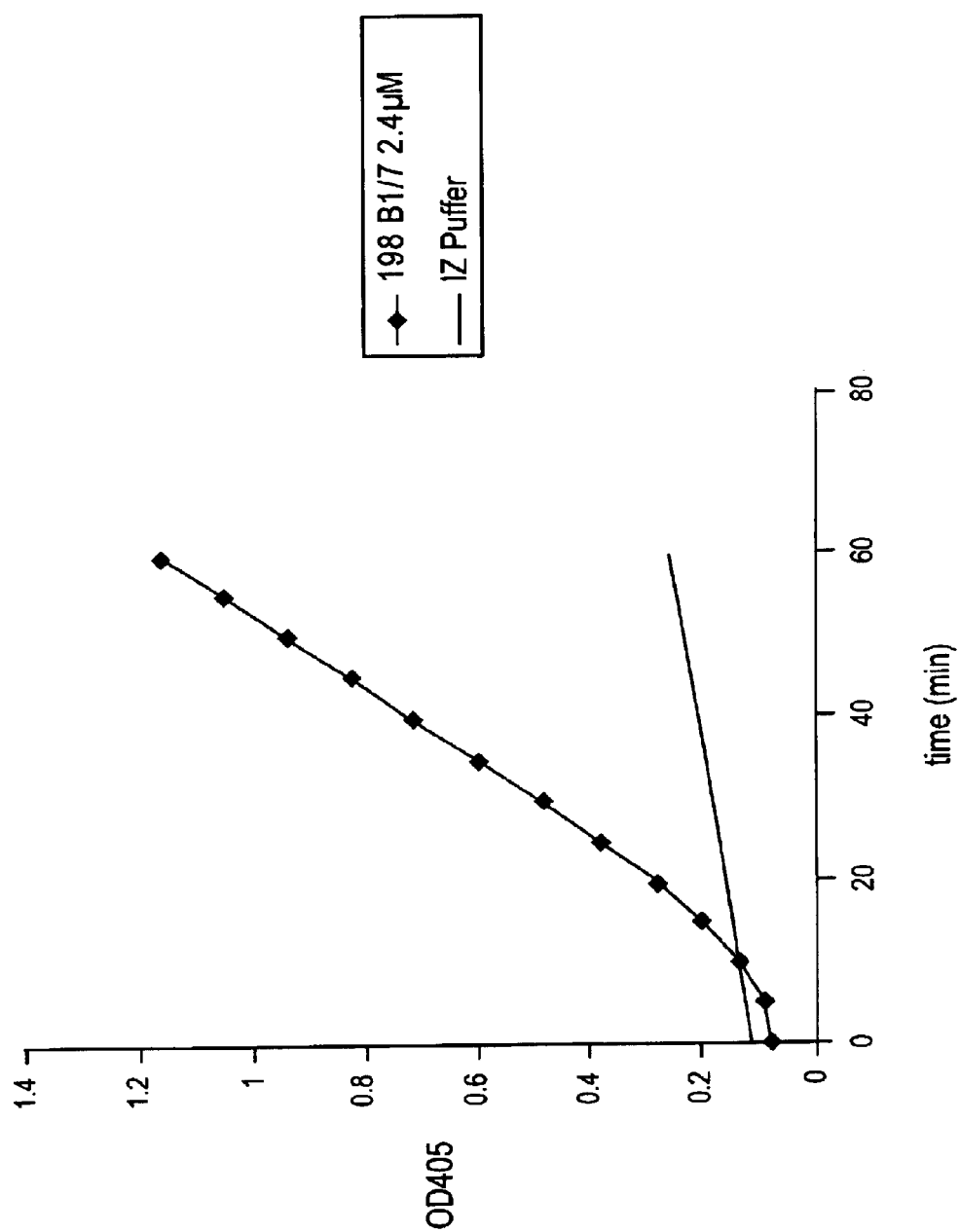

FIG. 21 shows that the addition of 2.4 µM peptide B1/7 to the reaction mixture led to a measureable generation of FXa.

Figure 22:
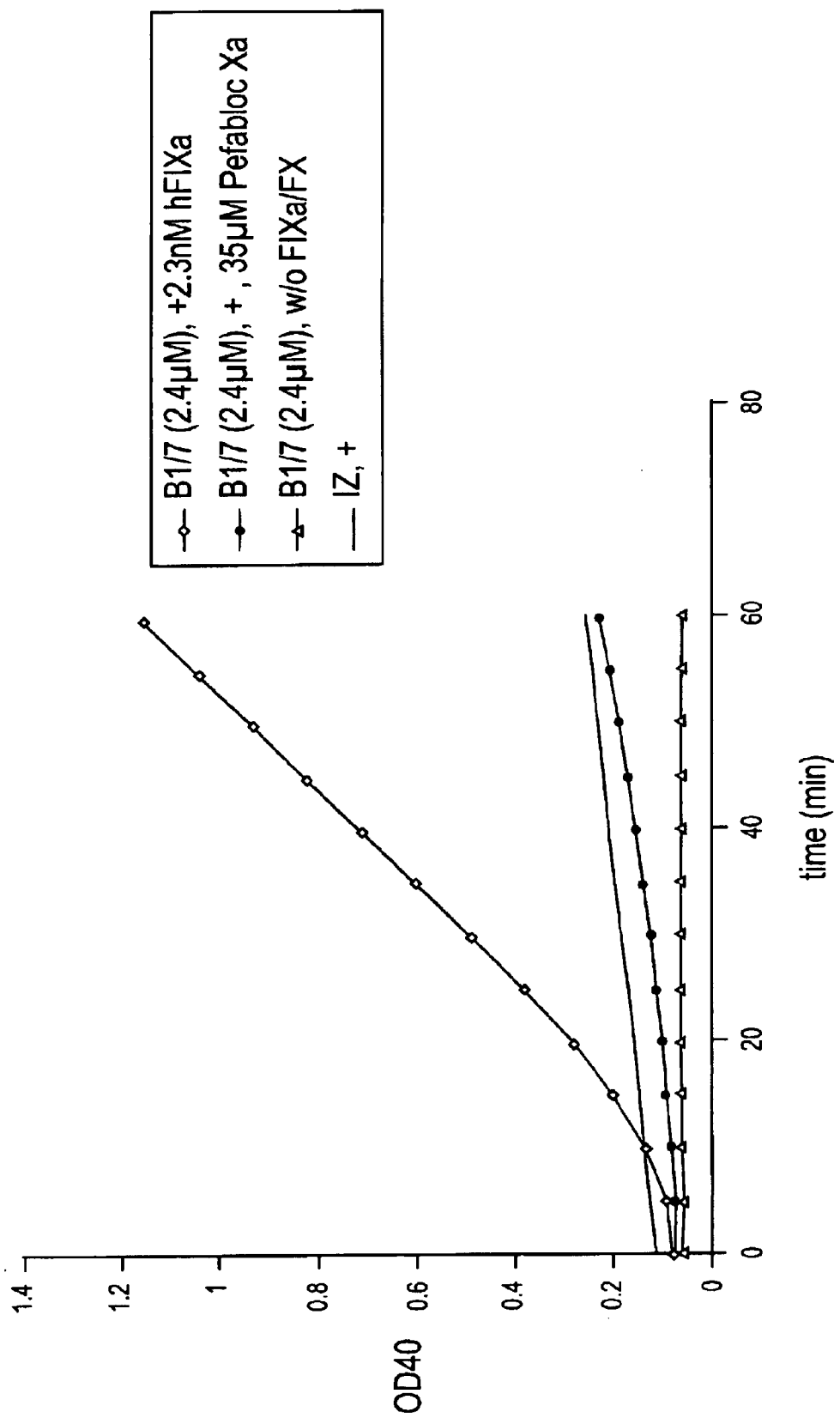

FIG. 22 shows that the addition of a FX-specific inhibitor results in a significant reduction in the reaction. If there was no FIXa and FX is added to the reaction mixture, no FXa was synthesized.

Figure 23:
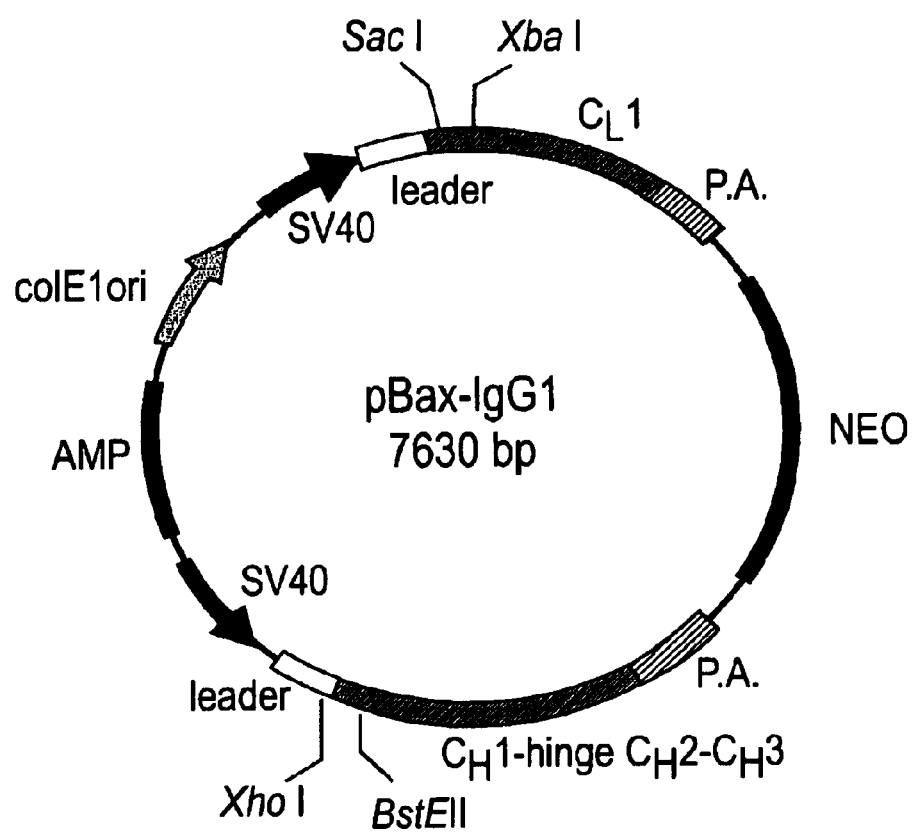

FIG. 23 shows vector pBax-IgG1.

Figure 24A:
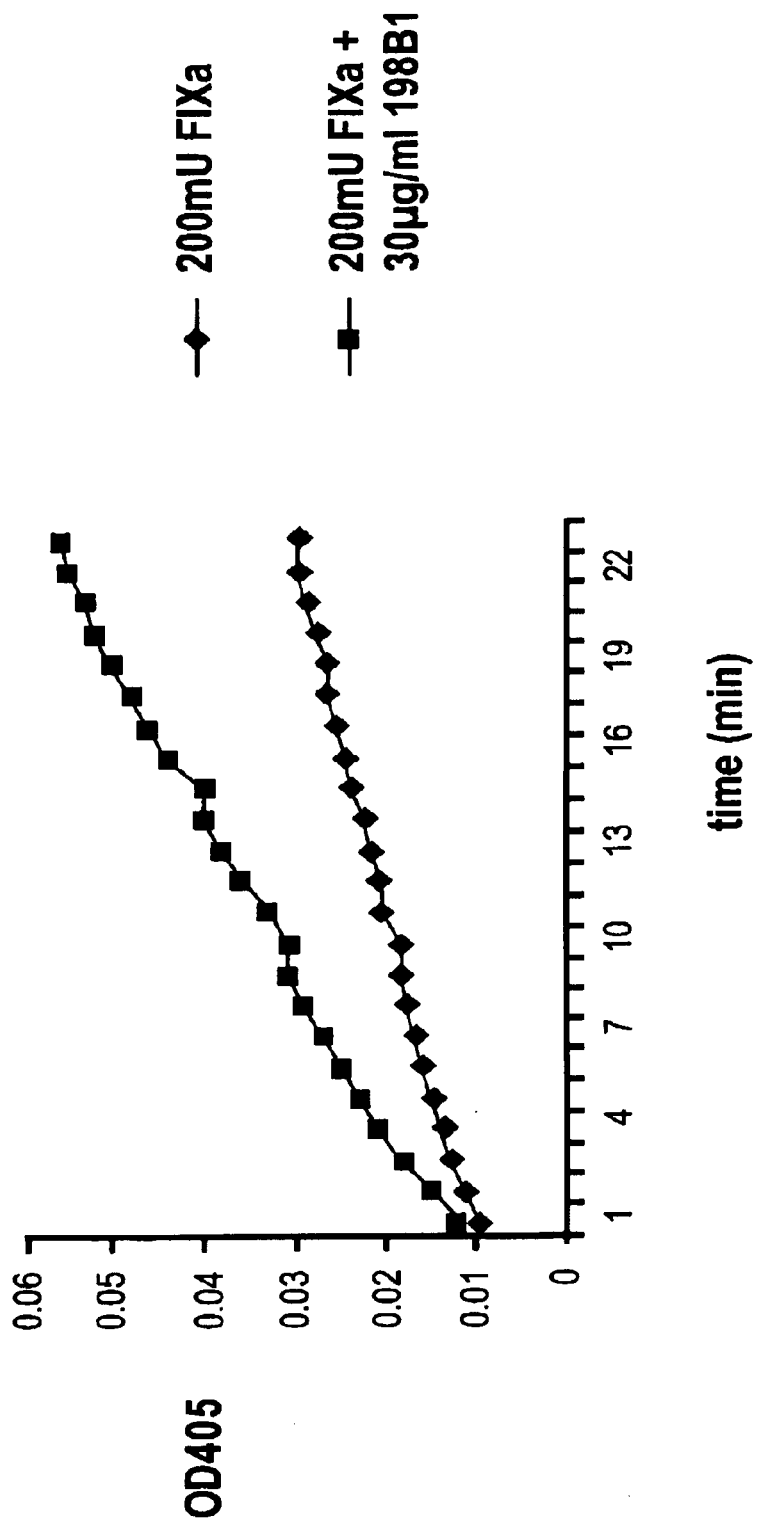
Figure 24B:
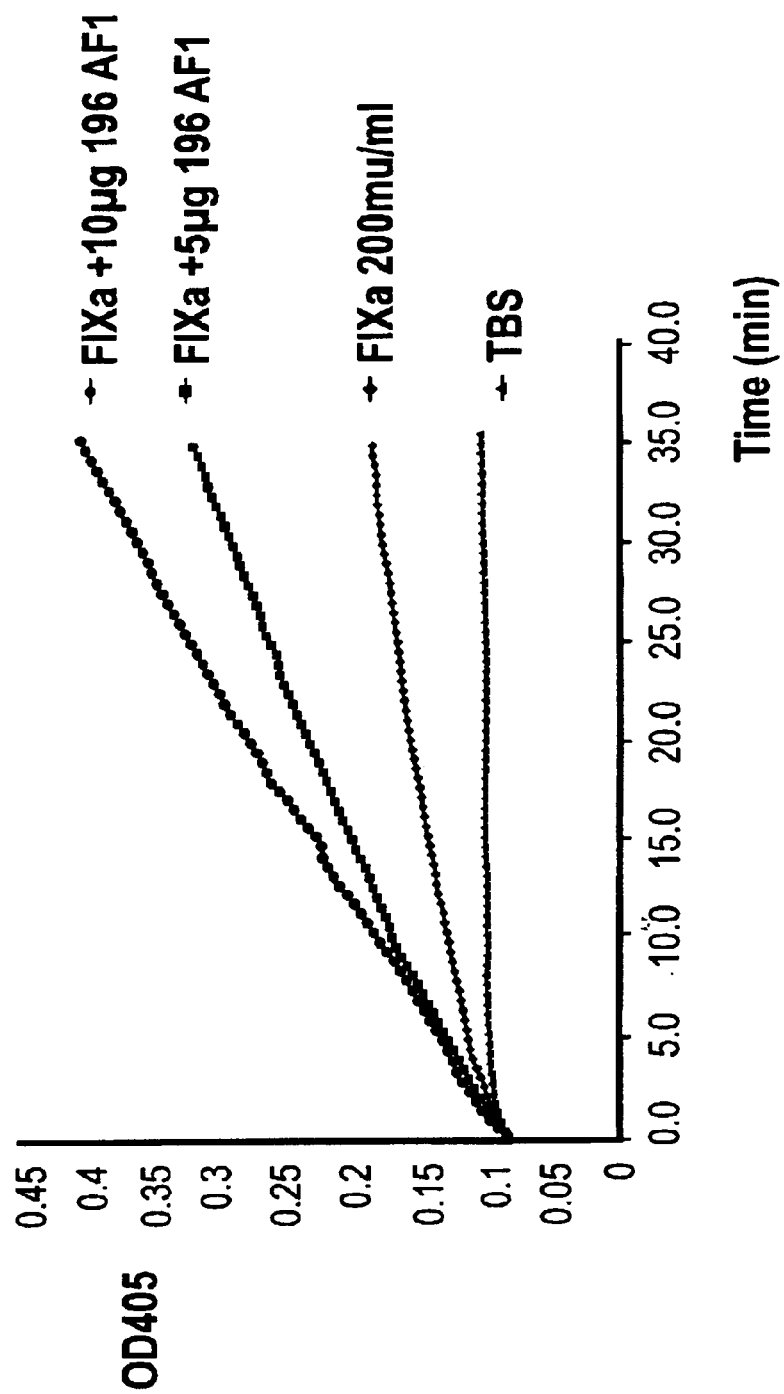

FIG. 24 shows the increase of the amidolytic activity of FIXa in the presence of antibody 198/B1 (FIG. 24A) and IgM antibody 198/AF1 (FIG. 24B).

Figure 25:
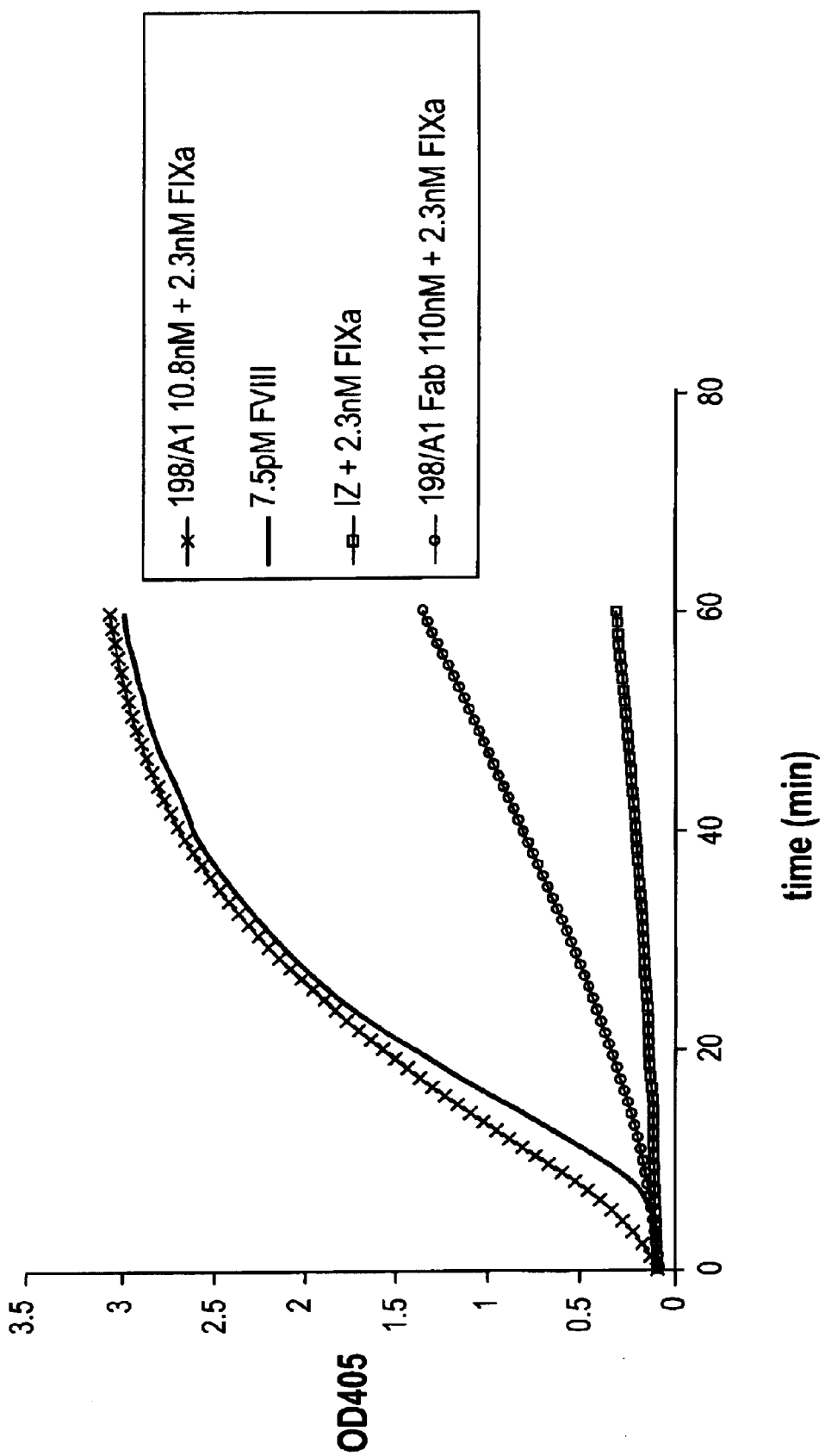

FIG. 25 demonstrates the chromogenic FVIII-like activity of the antibody 198/A1 Fab fragment in the presence of 2.3 nM human FIXa. As a positive control the intact antibody 198/A1 was used as well as 7.5 pM FVIII. The buffer control (IZ) was used as a negative control.

FIG. 26 shows the nucleotide and amino acid sequence of the 198AB2 scFv-alkaline phosphatase fusion protein (ORF of the expression vector pDAP2-198AB2#100, (SEQ.ID.NOs. 89 and 90).

The genes for the VL and the VH domains of antibody 198/AB2 (198/AB2 is an identical subclone of 198/B1) were derived from the corresponding hybridoma cells as described in example 10. The PCR product of the VH-gene was digested SfiI-AscI and the PCR-product of the VL-gene was digested AscI and NotI. VH and VL genes were linked via the AscI site and inserted into SfiI-NotI digested vector pDAP2 (Kerschbaumer R. J. et al, Immuno-technology 2, 145–150, 1996; GeneBank accession No.:U35316). PelB leader: leader sequence of *Erwinia carotovora* Pectate Lyase B, His tag, Histidinee tag for metal ion chromatography.

Figure 27:
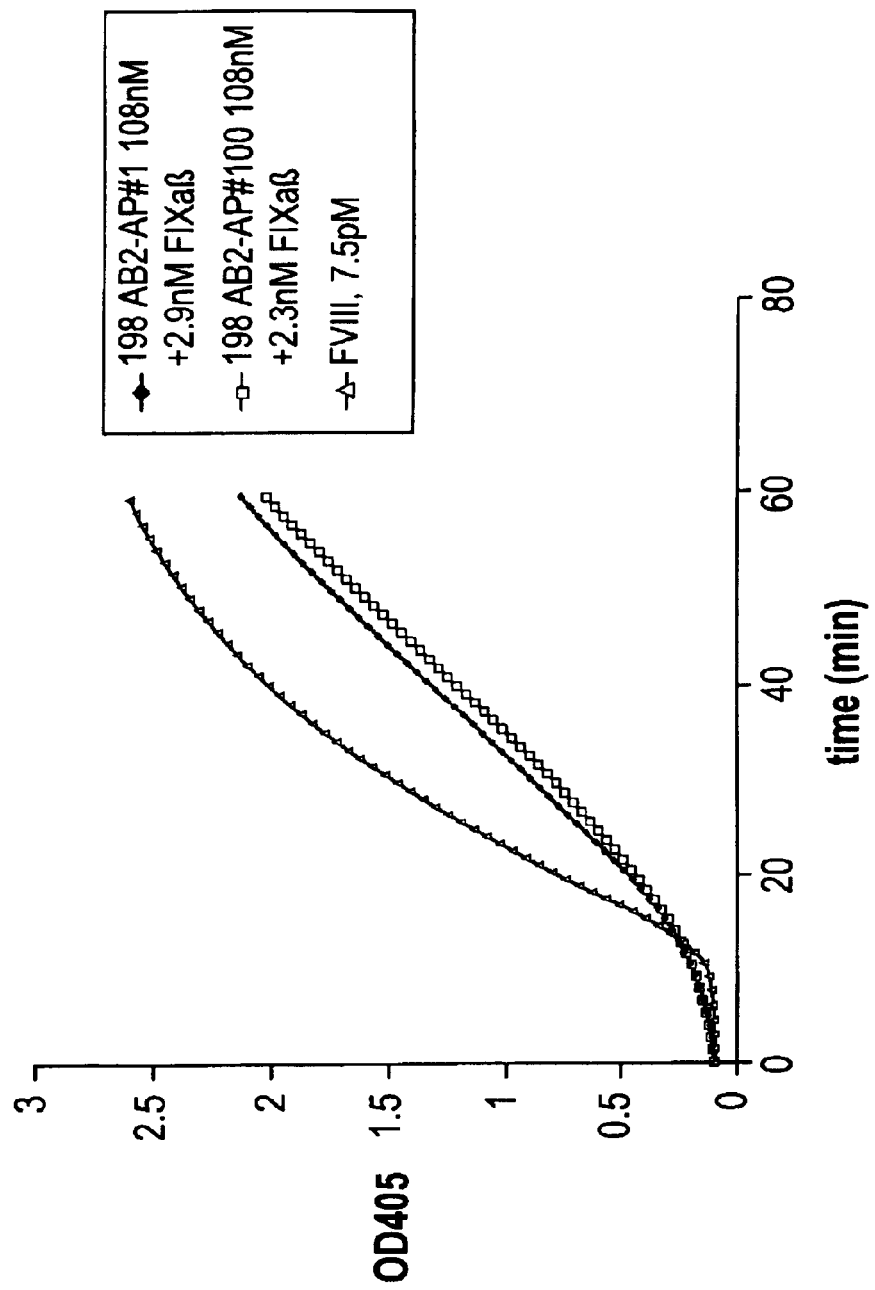

FIG. 27 demonstrates the chromogenic FVIII-like activity of two antibody 198/B1 (subclone AB2) scFv fragment-alkaline phosphatase fusion proteins (198AB2#1 and 198AB2#100) in the presence of 2.3 nM human FIXa. As a positive control 7.5 pM FVIII was used.

FIG. 28 shows the amino acid and nucleotide sequence of pZip198AB2#102 (SEQ.ID.NOs. 91 and 92).

FIG. 29 shows the nucleotide and amino acid sequence of the mAB#8860 scFv-alkaline phosphatase fusion protein (vector pDAP2-8860scFv#11, (SEQ.ID.NOs. 93 and 94). The genes for the VT and the VH domains of antibody #8860 were derived from the corresponding hybridoma cells as described in example 10. The PCR product of the VH-gene was digested SfiI-AscI and the PCR-product of the VL-gene was digested AscI and NotI. VH and VL genes were linked via the AscI site and inserted into SfiI-NotI digested vector pDAP2 (Kerschbaumer R. J. et al, Immunotechnology 2, 145–150, 1996; GeneBank accession No.:U35316).

FIG. 30 shows the nucleotide and amino acid sequence of the mAB #8860 scFv-leucine zipper fusion protein (miniantibody; vector p8860-Zip#1.2, (SEQ.ID.NOs. 95 and 96). The gene of the scFv fragment was derived from mAB #8860 and was swapped from vector pDAP2-8860scFv#11 into SfiI-NotI digested plasmid pZip1 (Kerschbaumer R. J. et al., Analytical Biochemistry 249, 219–227, 1997; GeneBank accession No.: U94951)

Figure 31:
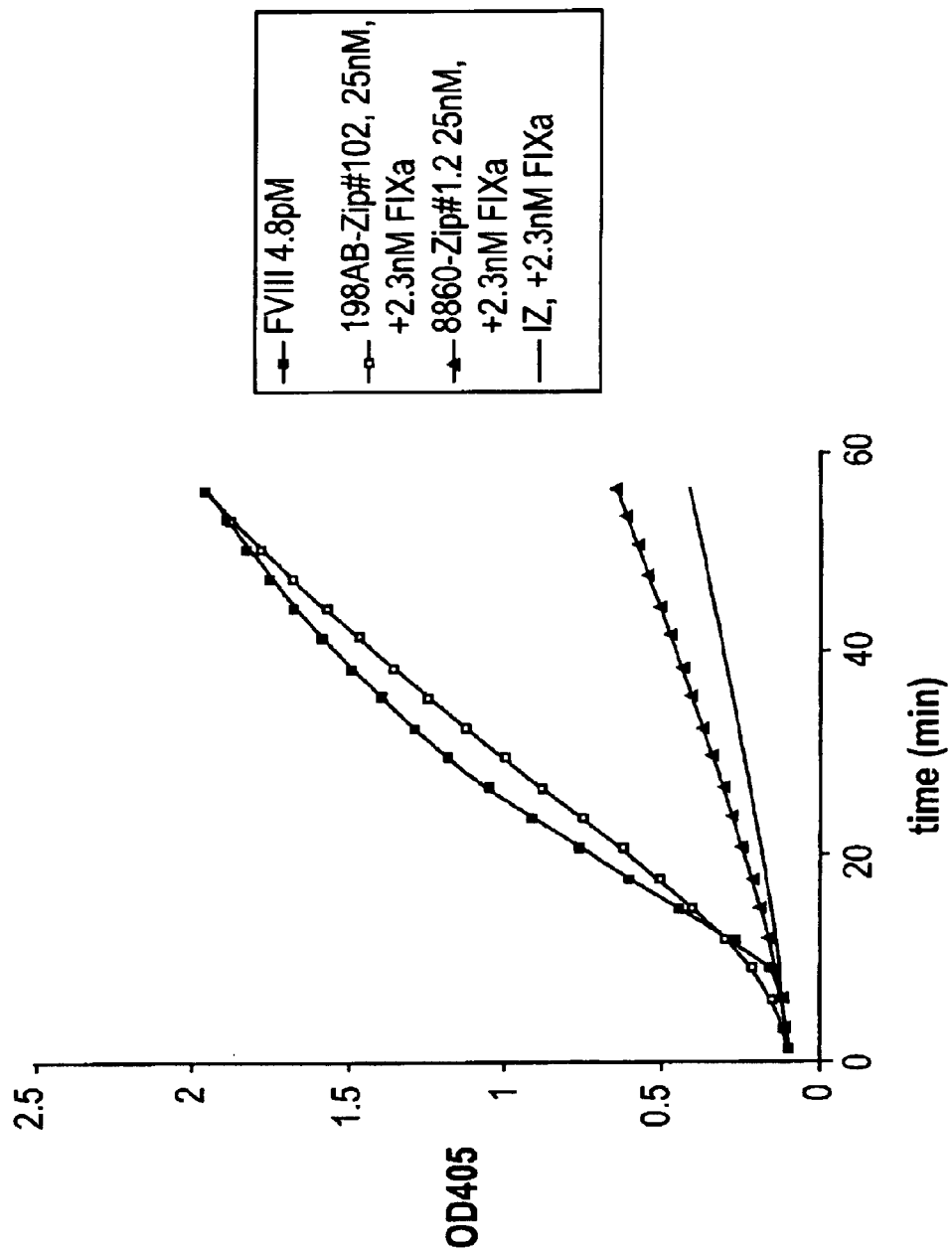

FIG. 31 demonstrates the chromogenic FVIII-like activity of the 198/B1 (subclone AB2) miniantibody 198AB-Zip#102 in the presence of 2.3 nM human FIXa. As a positive control 4.5 pM FVIII was used whereas a unrelated miniantibody (8860-Zip#1.2) and plain reaction buffer (IZ) served as negative controls.

Figure 32:
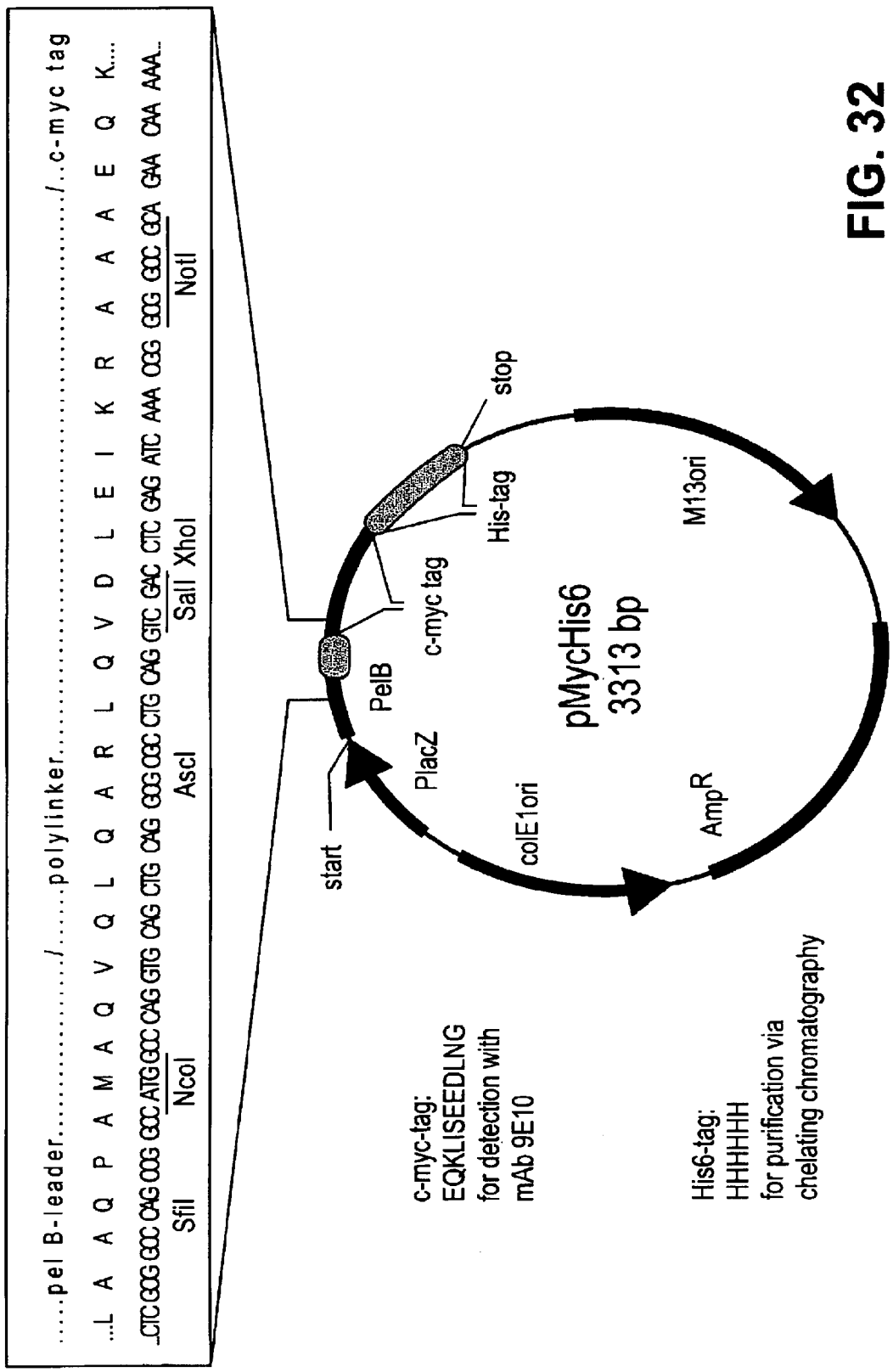

FIG. 32 shows a schematic representation of the plasmid pMycHis6 (SEQ ID NOS:107–110).

FIG. 33 shows the nucleotide and amino acid sequence of the part of the plasmid pMycHis6 differing from vector pCOCK (SEQ.ID.Nos. 97 and 98). Vector pMycHis6 was constructed by cleaving vector pCOCK (Engelhardt et al., 1994, Biotechniques, 17: 44–46) with NotI and EcoRI and insertion of the oligonucleotides: mychis6-co: 5'ggccgca-gaacaaaaactcatctcagaagaggatct gaatggggcggcacatcaccatcac-catcactaataag 3' (SEQ ID.No. 79) and mycchis-ic: 5' aattct-tattagtgatggtgatggtgatgtgccgccccattcagatcctcttct gagatgagttttgttctgc (SEQ.ID.No. 80).

FIG. 34 shows the nucleotide and amino acid sequence of 198AB2 scFv (linked to the c-myc-tag and the His6tag): ORF of the expression vector pMycHis6-198AB2#102. Vector pMycHis6 was constructed by cleaving vector pCOCK (Engelhardt O. et al, BioTechniques 17, 44–46, 1994) NotI-EcoRI and inserting the following annealed oligonucle-otides: (5'-GGCCGCAGAACAAAAACTCATCTCAGAA GAGGATCTGAATGGGGCGGCACATCA CCATCACCATCACTAATAAG-3' (SEQ.ID.No. 103) and 5'-TTATTAGTGATGGTGATGGT GATGTGCC GCCCCATTCAGATCCTCTTCTGAGATGAGTTTTTG TTCTGC-3'(SEQ.ID.NO. 104)). The resultant vector, named pMycHis6, was cleaved SfiI-NotI and the gene of scFv 198AB2 was swapped into this vector from vector pDAP2-198AB2#100.

FIG. 35 shows the nucleotide and amino acid sequence of the mAB #8860 scFv linked to the c-myc-tag and the His6-tag (vector p8860-M/H#4c, SEQ.ID.NOs. 101 and 102). Plasmid pMycHis6 was cleaved with SfiI and NotI and the DNA sequence coding for the scFv 8860#11 protein was inserted from pDAP2-8860scFv#µl (see FIG. 29) yielding plasmid p8860-M/H#4c.

Figure 36:
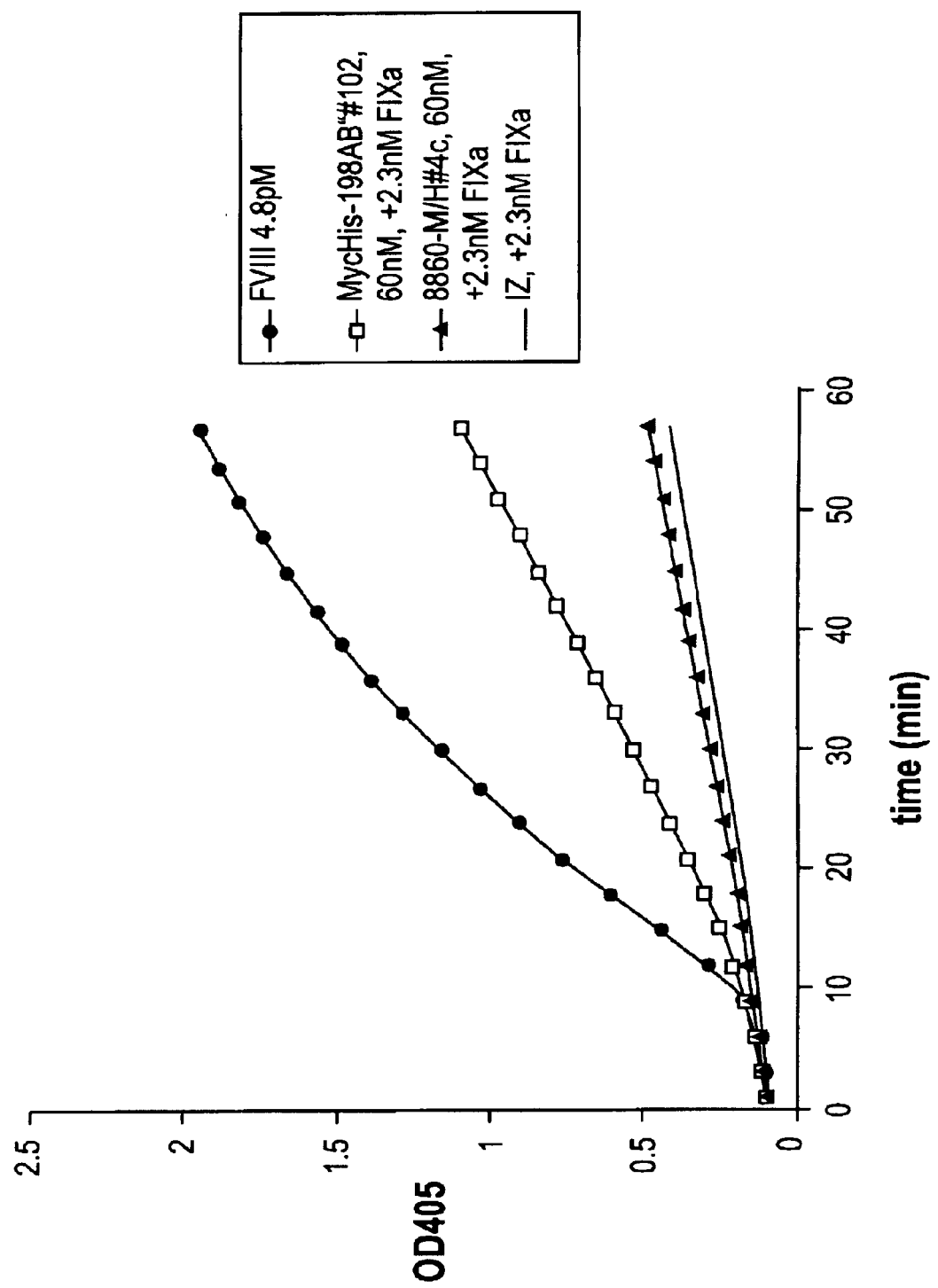

FIG. 36 demonstrates the chromogenic FVIII-like activity of the 198/B1 (subclone AB2) scFv fragment (MycHis-198AB2#102) in the presence of 2.3 nM human FIXa. As a positive control 4.8 pM FVIII was used whereas a unrelated scFv (8860-M/H#4c) and plain reaction buffer (IZ) served as negative controls.

Antibodies and Antibody Derivatives

The present invention also comprises the nucleic acids encoding the inventive antibodies and antibody derivatives, expression vectors, hybridoma cell lines, and methods for producing the same.

Antibodies are immunoglobulin molecules having a specific amino acid sequence which only bind to antigens that induce their synthesis (or its immunogen, respectively) or to antigens (or immunogens) which are very similar to the former. Each immunoglobulin molecule consists of two types of polypeptide chains. Each molecule consists of large, identical heavy chains (H chains) and two light, also identical chains (L chains). The polypeptides are connected by disulfide bridges and non-covalent bonds. In vivo, the heavy and light chains are formed on different ribosomes, assembled in the cell, and secreted as intact immunoglobu-lins (Roitt I. et al., in: Immunology, second ed., 1989).

The inventive antibodies and antibody derivatives and organic compounds derived there from comprise human and animal monoclonal antibodies or fragments thereof, single chain antibodies and fragments thereof and miniantibodies, bispecific antibodies, diabodies, triabodies, or di-, oligo- or multimers thereof. Also included are peptidomimetics or peptides derived from the antibodies according to the invention, e.g. they comprise one or several CDR regions, preferably the CDR3 region.

Further included are human monoclonal antibodies and peptide sequences which, based on a structure activity connection, are produced through an artificial modeling process (Greer J. et al., J. Med. Chem., 1994, Vol. 37, pp. 1035–1054).

The term factor IX/IXa activating antibodies and antibody derivatives may also include proteins produced by expression of an altered, immunoglobulin-encoding region in a host cell, e.g. "technically modified antibodies" such as synthetic antibodies, chimeric or humanized antibodies, or mixtures thereof, or antibody fragments which partially or completely lack the constant region, e.g. Fv, Fab, Fab' or F(ab)'$_2$ etc. In these technically modified antibodies, e.g., a part or parts of the light and/or heavy chain may be substituted. Such molecules may, e.g., comprise antibodies consisting of a humanized heavy chain and an unmodified light chain (or chimeric light chain), or vice versa. The terms Fv, Fc, Fd, Fab, Fab' or F(ab)$_2$ are used as described in the prior art (Harlow E. and Lane D., in "Antibodies, A Laboratory Manual", Cold Spring Harbor Laboratory, 1988).

The present invention also comprises the use of Fab fragments or F(ab)$_2$ fragments which are derived from monoclonal antibodies (mAb), which are directed against factor IX/factor IXa and cause an increase of the procoagu-lant activity of factor IXa.

Preferably, the heterologous framework regions and constant regions are selected from the human immunoglobulin classes and isotypes, such as IgG (subtypes 1 to 4), IgM, IgA and IgE. In the course of the immune response, a class switch of the immuno-globulins may occur, e.g. a switch from IgM to IgG; therein, the constant regions are exchanged, e.g. from µ to γ. A class switch may also be caused in a directed manner by means of genetic engineering methods ("directed class switch recombination"), as is known from the prior art (Esser C. and Radbruch A., Annu. Rev. Immunol., 1990, Vol. 8, pp. 717–735). However, the antibodies and antibody derivatives according to the present invention need not comprise exclusively human sequences of the immunoglobulin proteins.

In one particular embodiment, a humanized antibody comprises complement determining regions (CDRs) from murine monoclonal antibodies which are inserted in the framework regions of selected human antibody sequences. However, human CDR regions can also be used. Preferably, the variable regions in the human light and heavy chains are technically altered by one or more CDR exchanges. It is also possible to use all six CDRs or varying combinations of less than six CDRs.

The humanized antibody according to the present invention preferably has the structure of a human antibody or of a fragment thereof and comprises the combination of characteristics necessary for a therapeutic application, e.g., the treatment of coagulation disorders in patients, preferably factor VIII inhibitor patients.

A chimeric antibody differs from a humanized antibody in that it comprises the entire variable regions including the framework regions of the heavy and light chains of non-human origin in combination with the constant regions of both chains from human immuno-globulin. A chimeric antibody consisting of murine and human sequences may, for example, be produced. According to the present invention, the antibodies and antibody derivatives may also be single chain antibodies or miniantibodies (scFv fragments, which, e.g., are linked to proline-rich sequences and oligomerisation domains, e.g. Pluckthun A. and Pack P., Immunotechnology, 1997, Vol. 3, pp. 83–105) or single chain Fv (sFv) which incorporate the entire antibody binding region in one single polypeptide chain. For instance, single chain antibodies may be formed by linking the V-genes to an oligonucleotide which has been constructed as a linker sequence and connects the C terminus of the first V region with the N terminus of the second V region, e.g. in the arrangement VH-Linker-VL or VL-Linker-$V_H$; both, $V_H$ and $V_L$ thus may represent the N-terminal domain (Huston JS et al., Int. Rev. Immunol., 1993, Vol. 10, pp. 195–217; Raag R. and Whitlow M., FASEB J., 1995, Vol. 9, pp. 73–80). The protein which can be used as linker sequence may, e.g., have a length of up to 150 Å, preferably up to 80 Å, and more preferably up to 40 Å. Linker sequences containing glycine and serine are particularly preferred for their flexibility, or glutamine and lysine, respectively, for their solubility. The choice of the amino acid is effected according to the criteria of immunogenicity and stability, also depending on whether or not these single chain antibodies are to be suitable for physiological or industrial applications (e.g. immunoaffinity chromatography). The single chain antibodies may also be present as aggregates, e.g. as trimers, oligomers or multimers. The linker sequence may, however, also be missing, and the connection of the $V_H$ and $V_L$ chains may occur directly.

Bispecific antibodies are macromolecular, heterobifunctional cross-linkers having two different binding specificities within one single molecule. In this group belong, e.g., bispecific (bs) IgGs, bs IgM-IgAs, bs IgA-dimers, bs $(Fab')_2$, $bs(scFv)_2$, diabodies, and bs bis Fab Fc (Cao Y. and Suresh M. R., Bioconjugate Chem., 1998, Vol. 9, pp. 635–644).

By peptidomimetics, protein components of low molecular weight are understood which imitate the structure of a natural peptide component, or of templates which induce a specific structure formation in an adjacent peptide sequence (Kemp DS, Trends Biotechnol., 1990, pp. 249–255). The peptidomimetics may, e.g., be derived from the CDR3 domains. Methodical mutational analysis of a given peptide sequence, i.e. by alanine or glutamic acid scanning mutational analysis, allows for the identification of peptide residues critical for procoagulant activity. Another possibility to improve the activity of a certain peptide sequence is the use of peptide libraries combined with high throughput screening.

The term antibodies and antibody derivatives may also comprise agents which have been obtained by analysis of data relating to structure-activity relationships. These compounds may also be used as peptidomimetics (Grassy G. et al., Nature Biotechnol., 1998, Vol. 16, pp. 748–752; Greer J. et al., J. Med. Chem., 1994, Vol. 37, pp. 1035–1054).

Examples of hybridoma cells expressing the antibodies or antibody derivatives according to the invention were deposited on 9 Sep. 1999 under the numbers 99090924 (#198/A1), 99090925 (#198/B1) and 99090926 (#198/BB1) and on Dec. 16, 1999 under the numbers 99121614 (#193/A0), 99121615 (#196/c4), 99121616 (#198/D1), 99121617 (198/T2), 99121618 (#198/G2), 99121619 (#198/AC1) and 99121620 (#198/U2) according to the Budapest Treaty.

Methods of Production:

The antibodies of the present invention can be prepared by methods known from the prior art, e.g. by conventional hybridoma techniques, or by means of phage display gene libraries, immunoglobulin chain shuffling or humanizing techniques (Harlow E. and Lane D., in: Antibodies, A Laboratory Manual, Cold Spring Harbor Laboratory, 1988). The production of the inventive antibodies and antibody derivatives may, for instance, be made by conventional hybridoma techniques (Antibodies, A Laboratory Manual, Cold Spring Harbor Laboratory, 1988, Eds. Harlow and Lane, pp. 148–242). According to the present invention, human and also non-human species may be employed therefor, such as cattle, pigs, monkeys, chickens and rodents (mice, rats). Normal, immunocompetent Balb/c mice or FIX-deficient mice may, e.g., be used (factor IX-deficient mice may be obtained from Dr. Darrel Stafford from the University of North Carolina, Chapel Hill). Immunization may, e.g., be effected with factor IX, factor IXaα or completely activated factor IXaβ, or with fragments thereof.

The hybridomas are selected with a view to the fact that the antibodies and antibody derivatives in the supernatants of the hybridoma cells bind to factor IX/factor IXa and cause an increase of the procoagulant activity of factor IXa. The increase in the procoagulant activity may, e.g., be proven by assaying methods as known from the prior art for the measurement of factor VIII-like activity, e.g. chromogenic assays.

Alternatively, the antibodies and antibody derivatives of the invention may also be produced by recombinant production methods. In doing so, the DNA sequence of the antibodies according to the invention can be determined by known techniques, and the entire antibody DNA or parts thereof can be expressed in suitable systems. Recombinant production methods can be used, such as those involving phage display, synthetic and natural libraries, expression of the antibody proteins in known expression systems, or expression in transgenic animals (Jones et al., Nature, 19B6, Vol. 321, pp. 522–525; Phage Display of Peptides and Proteins, A Laboratory Manual, 1996, Eds. Kay et al., pp. 127–139; U.S. Pat. No. 4,873,316; Vaughan T. J. et al., Nature Biotechnology, 1998, pp. 535–539; Persic L. et al., Gene, 1997, pp. 9–18; Ames R. S. et al., J.Immunol.Methods, 1995, pp. 177–186).

The expression of recombinantly produced antibodies may be effected by means of conventional expression vectors, such as bacterial vectors, such as pBr322 and its derivatives, pSKF or eukaryotic vectors, such as pMSG and SV40 vectors. Those sequences which encode the antibody may be provided with regulatory sequences which regulate the replication, expression and secretion from the host cell. These regulatory sequences comprise promoters, e.g. CMV or SV40, and signal sequences.

The expression vectors may also comprise selection and amplification markers, such as the dihydrofolate reductase gene (DHFR), hygromycin-B phosphotransferase, thymidine-kinase etc.

The components of the vectors used, such as selection markers, replicons, enhancers etc., may either be commercially obtained or prepared by means of conventional methods. The vectors may be constructed for the expression in various cell cultures, e.g. for mammalian cells such as CHO, COS, fibroblasts, insect cells, yeast or bacteria, such as *E. coli*. Preferably, those cells are used which allow for an optimal glycosylation of the expressed protein. Particularly preferred is the vector pBax (cf. FIG. 17) which is expressed in CHO cells or in SK-Hep.

The production of Fab fragments or $F(ab)_2$ fragments may be effected according to methods known from the prior art, e.g. by cleaving a mAb with proteolytic enzymes, such as papain and/or pepsin, or by recombinant methods. These Fab and F(ab)$_2$ fragments may also be prepared by means of a phage display gene library (Winter et al., 1994, Ann. Rev. Immunol., 12: 433–455).

The antibody derivatives may also be prepared by means of methods known from the prior art, e.g. by molecular modeling, e.g. from Grassy G. et al., Nature Biotechnol., 1998, Vol. 16, pp. 748–752, or Greer J. et al., J. Med. Chem., Vol. 37, pp. 1035–1054, or Rees A. et al., in: "Protein Structure Prediction: A practical approach", ed. Sternberg M. J. E., IRL press, 1996, chapt. 7–10, pp. 141–261.

The purification of the inventive antibodies and antibody derivatives may also be carried out by methods described in the prior art, e.g., by ammonium sulfate precipitation, affinity purification (protein G-Sepharose), ion exchange chromatography, or gel chromatography. The following methods may be used as the test methods to show that the antibodies and antibody derivatives of the present invention bind to factor IX/factor IXa, increase the procoagulant activity of factor IXa or have factor VIII-like activity.: the one step coagulation test (Mikaelsson and Oswaldson, Scand. J. Haematol., Suppl., 33, pp. 79–86, 1984) or the chromogenic tests, such as COATEST VIII:C® (Chromogenix) or Immunochrom (IMMUNO). In principle, all the methods used for determining factor VIII activity may be used. As the control blank value for the measurements, e.g., unspecific mouse-IgG antibody may be used.

The present antibodies and antibody derivatives are suitable for therapeutic use in the treatment of coagulation disorders, e.g. in the case of hemophilia A, for factor VIII inhibitor patients etc. Administration may be effected by any method suitable to effectively administer the therapeutic agent to the patient, e.g. by oral, subcutaneous, intramuscular, intravenous or intranasal administration.

Therapeutic agents according to the invention may be produced as preparations which comprise a sufficient amount of antibodies or of antibody derivatives as the active agent in a pharmaceutically acceptable carrier substance. These agents may be present either in liquid or in powderized form. Moreover, the preparations according to the invention may also comprise mixtures of different antibodies, the derivatives thereof and/or organic compounds derived therefrom, as well as mixtures consisting of antibodies and factor 1× and/or factor IXa. Factor IXa may be present as factor IXaα and/or factor IXaβ. An example of an aqueous carrier substance is, e.g., saline. The solutions are sterile, sterilisation being effected by conventional methods.

The antibodies or antibody derivatives according to the invention may be present in lyophilized form for storage and be suspended in a suitable solvent before administration. This method has proven generally advantageous for conventional immunoglobulins, and known lyophilisation and reconstitution methods may be applied in this case.

Moreover, the antibodies and antibody derivatives according to the invention may also be used for industrial applications, e.g. for the purification of factor IX/factor IXa by means of affinity chromatography, or as a component of detection methods (e.g. ELISA assays), or as an agent for identification of and interaction with functional domains of a target protein.

The present invention will be described in more detail by way of the following examples and drawing figures, to which, however, it shall not be restricted.

EXAMPLES

Example 1

Immunization of Immunocompetent Mice and Generation of Anti-FIX/IXa Antibody Secreting Hybridoma Cells Groups of 1–3 normal immunocompetent 5–8 week old Balb/c mice were immunized with 100 µg antigen (100 µl doses) via the intraperitoneal (i.p.) route. In a typical experiment, mice were inoculated with either recombinant human coagulation factor (F) IX (Benefix™), human activated FIXaα (Enzyme Research Laboratories, Lot: FIXaα 1190L) or human FIXaβ (Enzyme Research Laboratories, Lot: HFIXAaβ 1332 AL,) adjuvanted with Al(OH)$_3$ or KFA.

Individual mice were boosted at various times with 100 µg antigen (10011 doses, i.p) and sacrificed two days later. Spleen cells were removed and fused to P3×63-Ag8 6.5.3 myeloma cells essentially as described by Lane et al., 1985 (J. Immunol. Methods, Vol. 81, pp. 223–228). Each fusion experiment was individually numbered, i.e. #193, 195, 196 or 198.

Hybridoma cells were grown in 96 well plates on a macrophage feeder layer (app. $10^5$ cells/ml) and selected in HAT-medium (RPMI-1640 medium supplemented with antibiotics, 10% FCS, Na-pyruvate, L-glutamine, 2-mercaptoethanol and HAT (HAT 100x: $1.0 \times 10^{-2}$M hypoxanthine in H$_2$O (136.1 mg/100 ml H$_2$O), $4.0 \times 10^{-5}$M aminopterin in H$_2$O (1.76 mg/100 ml H$_2$O) and $1.6 \times 10^{-3}$M thymidine in H$_2$O (38.7 mg/100 ml H$_2$O). Medium was first changed after 6 days and thereafter twice a week. After 2–3 weeks HAT-medium was changed to HT-medium (RpMI-1640 supplemented with antibiotics, 10% FCS, Na-pyruvate, L-glutamine, 2-mercaptoethanol and HT) and later on (after additional 1–2 weeks) to normal growth medium (RPMI-1640 medium supplemented with 10% FCS, Na-pyruvate, L-glutamine and 2-mercaptoethanol) (see: HYBRIDOMA TECHNIQUES, EMBO, SKMB Course 1980, Basel).

In another set of experiments FIX deficient C57B16 mice (Lin et al., 1997, Blood, 90: 3962) were used for immunization and subsequent hybridoma production. Since FIX knockout (k.o.) mice do not express endogenous FIX, the anti (a)-FIX antibody spectrum achievable is supposed to be different compared to normal Balb/c mice (due to lack of tolerance).

Example 2

Assaying for FVIII-like Activity in Supernatants of Anti-Fix/FIXa Antibody Secreting Hybridoma Cells In order to assay the FVIII-like activity of anti-FIXa antibodies secreted by hybridoma cells, the commercially available test-kit COATEST VIII:C/4® (Chromogenix) was employed. The assay was done essentially as described by the manufacturer with the following modifications:

To allow high throughput screening, the assay was downscaled to microtiter plate format. Briefly, 25 µl aliquots of hybridoma supernatants were transferred to microtiter plate (Costar, #3598) wells and warmed to 37° C. Chromogenic substrate (S-2222), synthetic thrombin inhibitor (1–2581), factor (F) IXa and FX were reconstituted in sterile water and FIXa/FX was mixed with phospholipids according to the supplier's protocol. Per reaction, 50 µl of the phospholipid/FIXa/FX solution were combined with 25 µl CaCl$_2$ (25 mM) and 50 µl of the substrate/inhibitor cocktail. To start the reaction, 125 µl of the premix were added to the hybridoma supernatant in the microtiter plates and incubated at 37° C. Absorbency at 405 nm and 490 nm of the samples was read at various times (30 min to 12 h) against a reagent blank (MLW, cell culture medium instead of hybridoma supernatant) in a Labsystems iEMS Reader MF™ microtiter plate reader. FVIII-like activity of the samples was calculated by comparing the absorbency of the samples against the absorbency of a diluted FVIII reference standard (IMMUNO AG # 5T4AR00) using GENESIS™ software.

Figure 1:
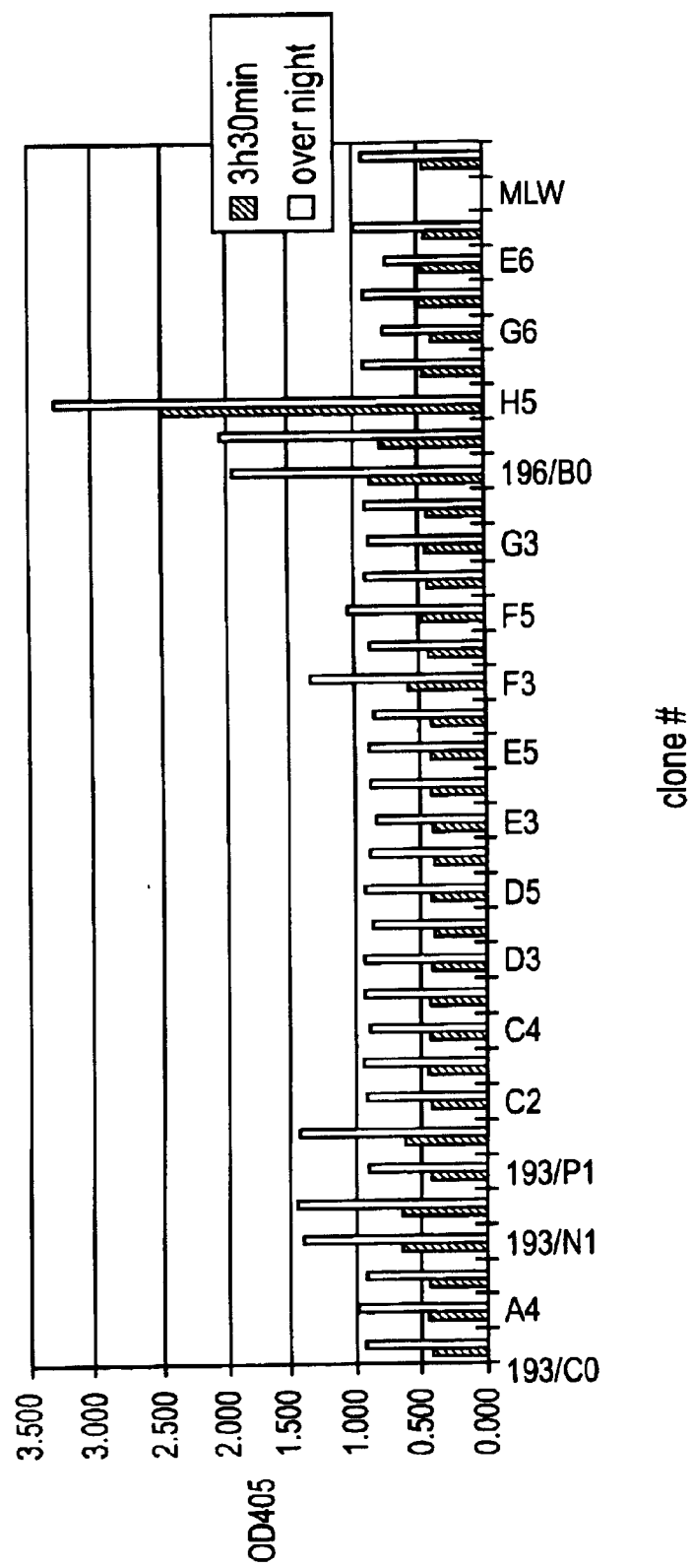
FIG. 1 shows the results of a screening of supernatants from hybridoma cell cultures for FVIII-like activity. Preselected clones from fusion experiments, #193, #195 and #196, were tested in a chromogenic assay.

The results of a screening for FVIII-like activity in hybridoma cell culture supernatants are shown in FIG. 1. Pre-selected clones derived from fusion experiments #193, #195 and #196 (see above) were examined in a chromogenic FVIII assay as described. Clones 193/M1, 193/N1 and 193/P1 are subclones derived from the master clone 193/C0 (see below). Master clone 195/10 was derived from fusion experiment #195 and clones 196/A0, 196/B0 and 196/C0 were derived from fusion experiment #196. In a typical screening experiment, approximately 1000 clones (in 96 wells) from a single fusion experiment were pre-screened for FVIII-like activity. Subsequently, selected clones were grown on a larger scale (3–5 ml supernatant) and re-analyzed in a chromogenic assay. As a negative control cell culture medium was assayed on each plate (MLW).

Wells either exhibiting high FVIII-like activity or substantial FVIII-like activity were subjected to subcloning procedures. The selection and subcloning process is exemplified for the screening and subcloning of an IgG producing cell line (i.e. 193/C0) but has been done exactly the same way for an IgM (i.e. 196/C0, see below, FIG. 5) producing clone.

The selection process was done by initially plating all hybridoma cell clones derived from a single fusion experiment on ten 96 well plates thereby creating the so called "master plates". Singular positions (wells) on a master plate usually contained more than one hybridoma cell clone (usually 3 to 15 different clones). Subsequently, the antibody secreted by only several thousand cells was tested. These cells grew under conditions suboptimal for antibody production, which is known to be best in dying cells. So the expected specific anti-FIX antibody concentration in the supernatant may be in the range of 10–12 to 10–14 M. This explains why incubation periods had to be extended compared to standard FVIII assays.

Figure 2:
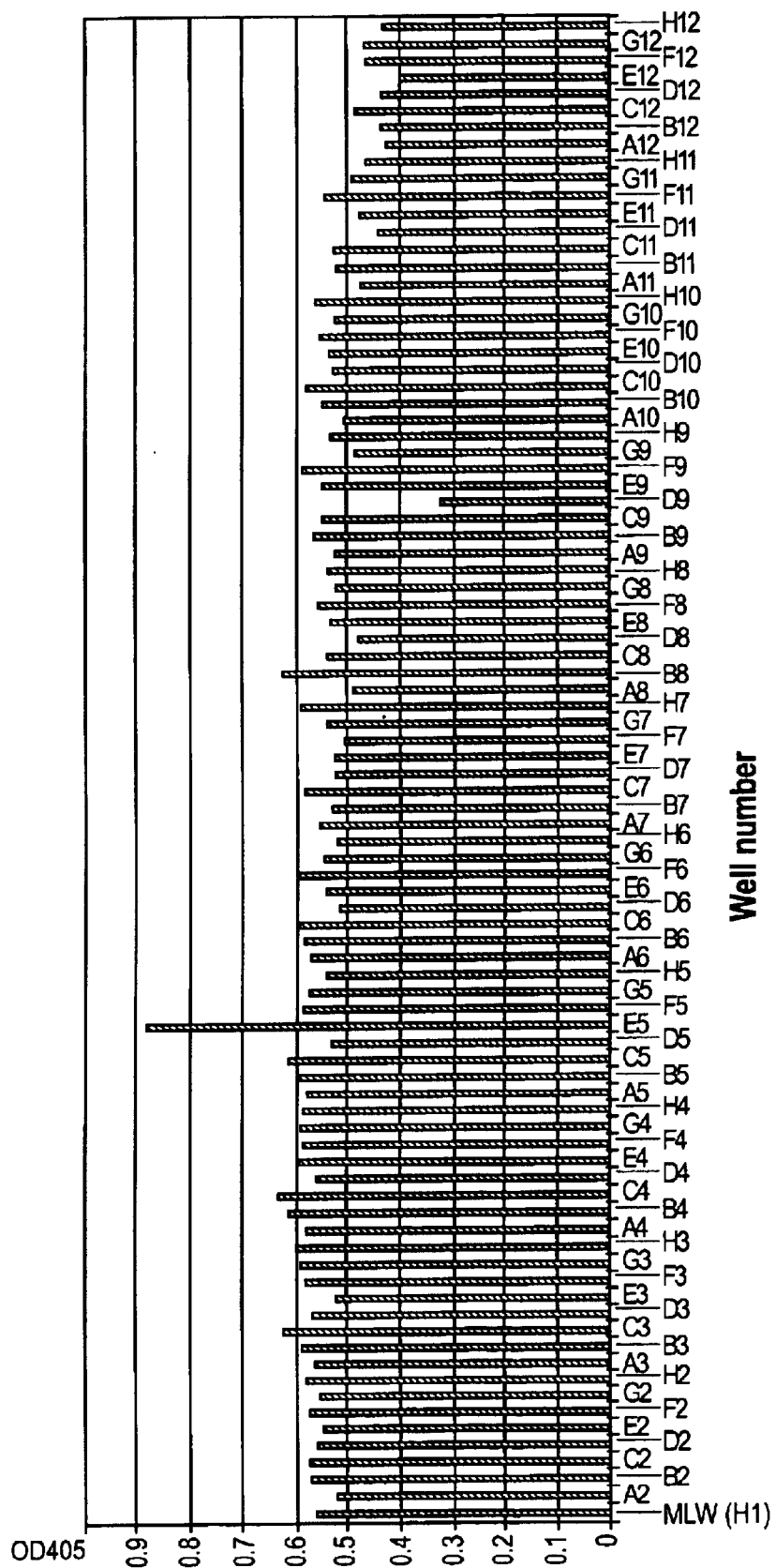
FIG. 2 shows the results of screening for IgG-mediated factor VIII-like activity in supernatants of a hybridoma cell culture of a master plate.
Figure 3:
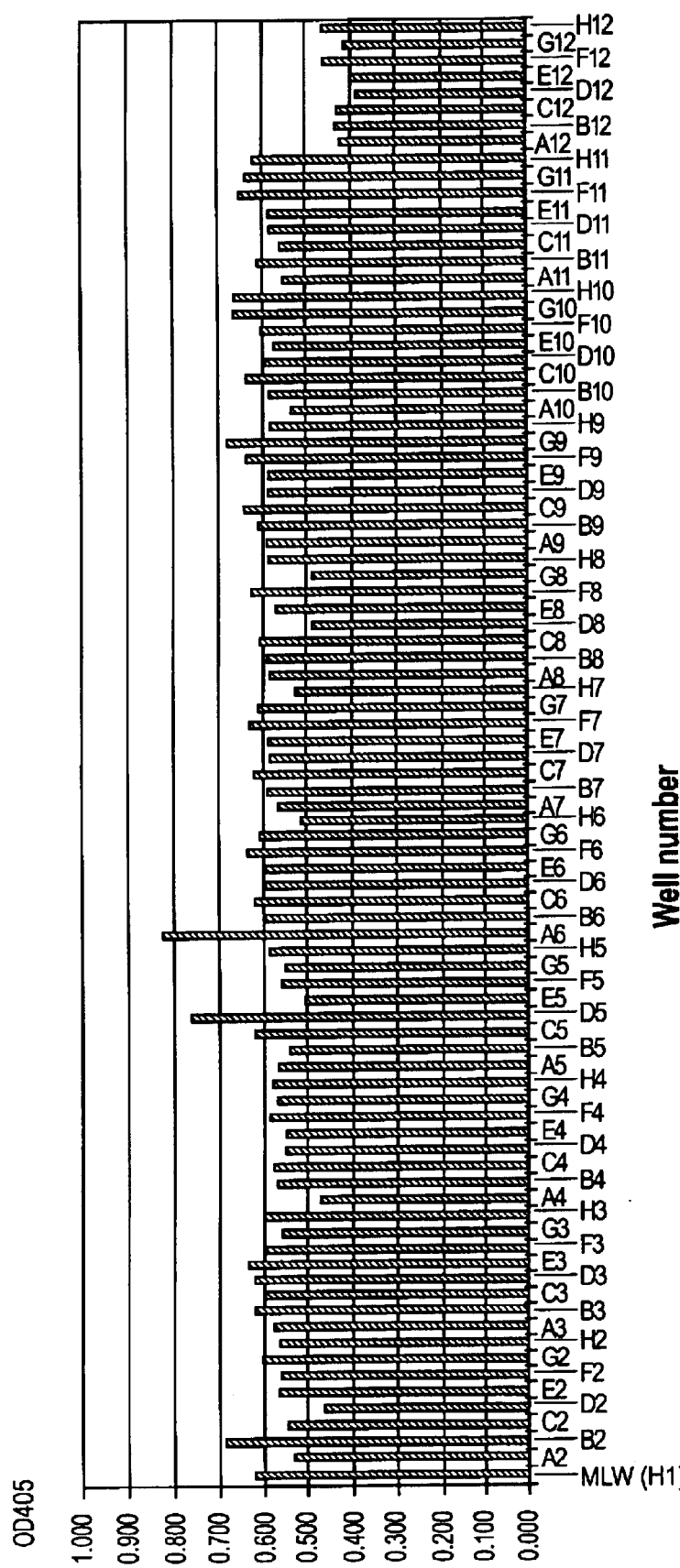
FIG. 3 shows the subcloning of clone 193/C0, namely the results of the first cloning round.

Results of a screening for an IgG mediated FVIII-like activity in hybridoma cell culture supernatants of a master plate are shown in FIG. 2. Supernatants were examined in a chromogenic FVIII assay. Shown are the results derived from the fifth master plate of fusion experiment number #193 (Balb/c mice immunized with FIXaα). Absorbance was read after 4 hours of incubation at 37° C. Position E5 was identified as exhibiting FVIII like activity significantly higher than the blank (MLW). This cell pool was designated 193/C0 and was further subcloned (FIG. 3). As each well of the master plate contains more than one hybridoma cell clone, cells of a single positive well were expanded and plated at a calculated cell density of 2–0.2 cells/well on a 96 well plate. Again, the supernatants were tested for FVIII-like activity and positive positions were subjected to another round of subcloning. Typically three to four rounds of subcloning were performed with each clone displaying FVIII-like activity to obtain homogenous cell populations. Here the results of the chromogenic assay of the 193/C0 subclones are shown. Absorbance was read after a 4 hour incubation period at 37° C. Positions A6 and D5 exhibited substantial FVIII-like activity and were named 193/M1 and 193/P1, respectively. These two clones were subjected to another round of subcloning. As a negative control plain cell culture medium was assayed on each plate (MLW(H1)).

Figure 4:
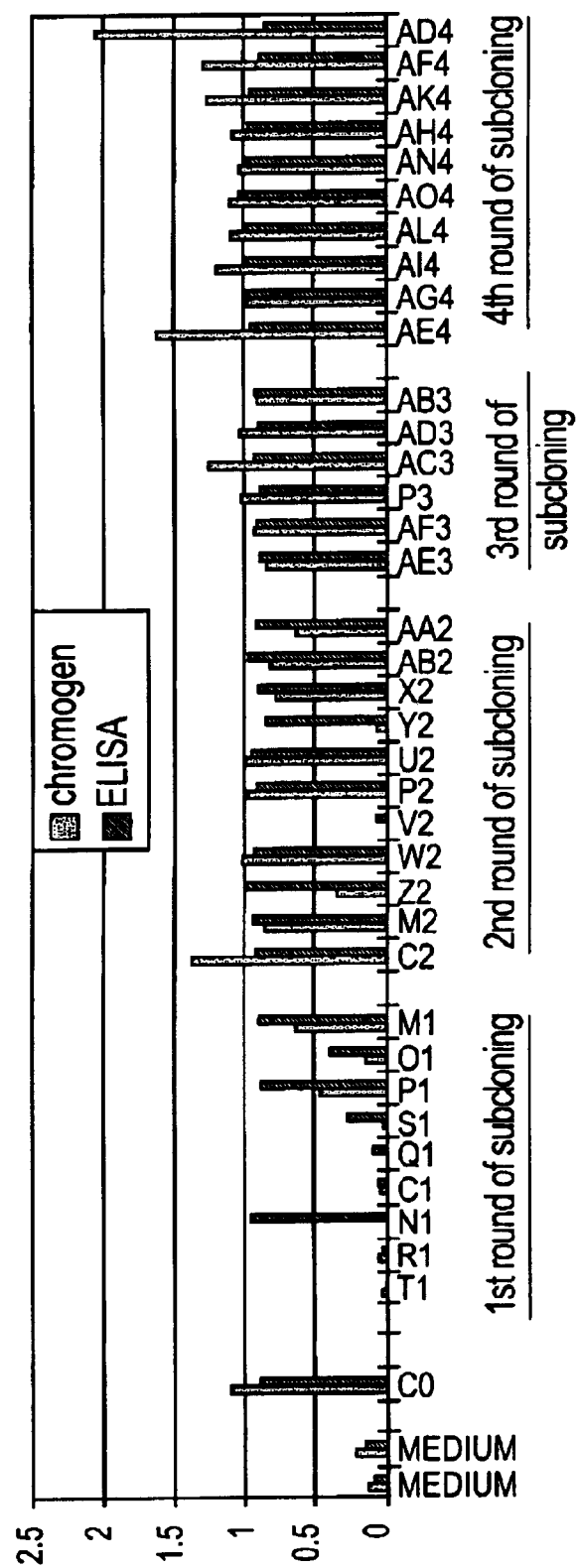
FIG. 4 shows a comparison of the chromogenic FVIII-like activity and factor IX-ELISA-reactivity of hybridoma cultures derived from the starting clone 193/C0.

A comparison of chromogenic FVIII-like activity and FIX-ELISA reactivity of small scale (3 ml) hybridoma cultures is shown in FIG. 4. Before a decision was made whether a master clone (or subclone) was to be further subcloned, clones were grown at a 3–5 ml scale and the supernatants were checked again. This graph shows the FIX specific ELISA results and the FVIII-like chromogenic activity of the master clone 193/C0 and all its subclones which were identified as positives and re-checked. Blanks (absorbency of the chromogenic reagent itself) were subtracted in the case of the ELISA as well as the chromogenic assay readings depicted here. Clone 193/M1 was subcloned and yielded clones 193/V2, 193/M2 and 193/U2. The other clones of the $2^{nd}$ round came from 193/P1, 193/AB2 and 193/P2 were subcloned. 193/AF3, 193/AB3 and 193/AE3 are subclones of 193/AB2. The other clones of the $3^{rd}$ round came from 193/P2. Finally 193/AF3 (→>193/AF4), AE3 (→193/AE4, 193/AL4, 193/AN4 and 193/AO4) and 193/AD3 (→193/AG4, 193/AH4, 193/AD4, 193/AI4, 193/AK4) were subcloned.

From each fusion experiment, several (5–15) master clones (selected from the master plate) were identified and subjected to subcloning. After 3 rounds of sub-cloning, most of the cell lines were homogenous as demonstrated by ELISA and chromogenic activity analysis (see FIG. 4) as well as by cDNA sequence analysis. A specific master clone and all its subclones produce the same FIX/FIXa binding antibody. However, there are huge differences in the antibody protein sequences of clones derived from different master clones (see Example 11). Most hybridoma cell lines express antibodies from the IgG subclass (i.e. clones #193, #198, like 198/A1, 198/B1, 198/BB1). However, we were also able to select some clones expressing IgM antibodies.

Figure 5:
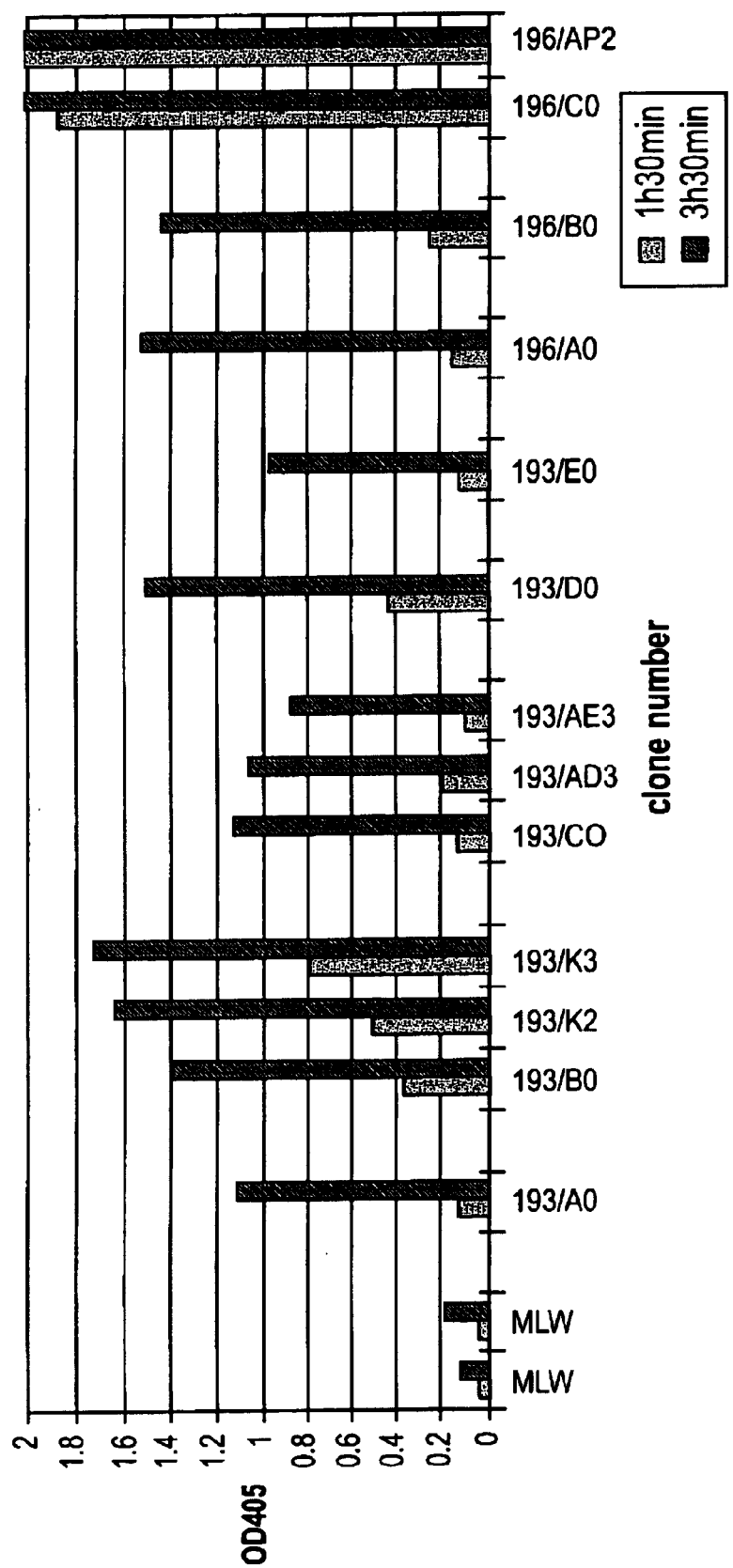
FIG. 5 shows the results of the measurement of the chromogenic activity of some master clones and sub-clones.

The chromogenic activity of hybridoma supernatant of some important master clones and subclones was determined. Absorbance was measured after a 1 h 30 min and 3 h 30 min incubation period at 37° C. (FIG. 5). In contrast to all the clones from the $193^{rd}$ fusion, clone 196/C0 and its subclone 196/AP2 produced a FIX/FIXa-specific IgM antibody that gave a strong chromogenic activity even after a short period of incubation.

The following cell lines have been deposited with the European Collection of Cell Cultures (ECACC) in accordance with the Budapest Treaty: 198/B1 (ECACC No. 99090925, deposited Sep. 9, 1999); 198/A1 (ECACC No. 99090924, deposited Sep. 9, 1999); 198/BB1 (ECACC No. 99090926, deposited Dec. 16, 1999); 193/AO (ECACC No. 99121614, deposited Dec. 16, 1999); 196/C4 (ECACC No. 99121615, deposited Dec. 16, 1999); 198/DI (ECACC No. 99121616, deposited Dec. 16, 1999); 198/T2 (ECACC No. 99121617, deposited Dec. 16, 1999); 198/G2 (ECACC No. 99121618, deposited Dec. 16, 1999); 198/AC1 (ECACC No, 99121619, deposited Dec. 16, 1999); and 198/U2 (ECACC No. 99121620, deposited Dec. 16, 1999). The address of the ECACC is Salisbury. Wiltshire SP4 OJG, UK.

To do a more in depth analysis of the biochemical properties of certain antibodies, homogenous hybridoma cell lines expressing different antibodies with FVIII-like activity were expanded and used to express the antibody in question on a larger scale (100–1000 ml). These antibodies were affinity purified (see Example 3) prior to being used in further experiments.

Example 3

Factor IX/FIXa$_{(\alpha,\beta)}$ Binding Properties of Antibodies Exhibiting FIX/FIXa Activating Activity Factor IX and the two activated forms of FIX, FIXaα and FIXaβ (FIX/FIXa$_{(\alpha,\beta)}$) were diluted in TBS (25 mM Tris HCl, 150 mM NaCl, pH 7.5) to a final concentration of 2 μg/ml. Nunc Maxisorp ELISA plates were coated with 100 μl FIX/FIXa$_{(\alpha,\beta)}$ solution according to standard procedures (4° C., overnight) and washed several times with TBST (TBS, 0.1% (v/v) Tween 20). 50 µl hybridoma supernatant was diluted 1:1 with 50 µl TBST/2% BSA and added to the coated ELISA plate. After an incubation period of 2 h at room temperature (RT), plates were washed 4 times with TBST and incubated (2 h, RT) with 100 µl/well of a 1:25000 dilution (in TBST/1% BSA) of an anti-mouse IgG (Fc-specific) peroxidase conjugated antibody (Sigma, #A-0168). Wells were washed 5 times with TBST and finally stained with 100 µl freshly prepared staining solution (10 ml 50M sodium citrate, pH 5 supplemented with 100 µl OPD (60 mg OPD/ml) and 10 µl 30% $H_2O_2$). The reaction was stopped by the addition of 50 ml $H_2S_4$ and the optical density recorded at 492 nm and 620 nm in a Labsystems iEMS Reader MF™ microtiter plate reader employing GENESIS™ software.

In certain cases, instead of an anti-mouse IgG ELISA, an anti-mouse IgM ELISA was carried out.

Purification of Mouse-IgG from Hybridoma Cell Culture Supernatants

Hybridoma supernatant (100–500 ml) was supplemented with 200 mM Tris/HCl buffer (pH 7.0) and solid NaCl to give final concentrations of 20 mM Tris and 3M NaCl, respectively. The supernatant was then clarified by centrifugation at 5500×g for 10 minutes. A 1 ml protein G affinity chromatography column (Protein G Sepharose Fast Flow, Amersham-Pharmacia) was washed with 15 ml 20 mM Tris/Cl pH 7.0 and afterwards equilibrated with 10 ml of 20 mM Tris/Cl buffer pH 7.0 containing 3M NaCl. The hybridoma supernatant containing 3M NaCl was then loaded onto the column by gravity. The column was washed with 15 ml of 20 mM Tris/Cl buffer, pH 7.0, containing 3M NaCl. Bound IgG was further eluted with 12 ml glycine/HCl buffer pH 2.8 and 1 ml fractions were collected. 100 µl of 1M Tris pH 9.0 were added to each fraction for neutralization. Fractions containing the IgG were identified by mixing 50>1 with 150 µl of a staining solution (BioRad concentrate, 1:5 diluted with water) in wells of a microplate. Positive fractions were pooled, concentrated to 1 ml in an ultrafiltration concentrator device (Centricon Plus 20, Amicon) according to the manufacturer. The concentrate was diluted with 19 ml TBS (20 mM Tris/Cl buffer pH 7.0 containing 150 mM NaCl) and again concentrated to 1 ml. The diluting-concentrating step was repeated for two more times in order to bring IgG into TBS.

Purification of Mouse-IgM from Hybridoma Cell Supernatants

100–500 ml of hybridoma cell culture supernatant were concentrated to 5–10 ml either with an ultra-filtration concentrator device (Centricon Plus 20, Amicon) according to the manufacturer or by ammonium sulfate precipitation (40% saturation, 0° C.) and redissolving the precipitate with 5–10 ml of TBS. In either case the concentrate was dialyzed against 20 mM Tris Cl buffer pH 7.4 containing 1.25M NaCl and further concentrated to 1 ml in a Centricon Plus 20, (Amicon) ultrafiltration device. IgM was purified from this concentrate with the Immunopure IgM Purification Kit (Pierce) according to the manufacturer. Fractions collected during elution from the maltose binding protein-column were tested for IgM, pooled, concentrated and brought into TBS as described for IgG.

Determination of IgG Concentrations in Purified Preparations

Total IgG content 280 nm–extinction of appropriate dilutions were measured. E280=1.4 corresponds to 1 mg/ml protein.

Factor IXa Specific IgG (Quantitative ELISA)

Wells of a microplate (Nunc Maxisorp) were incubated with 2 µg/ml factor IXa diluted in TBS (25 mM Tris/HCl pH 7.5 containing 150 mM NaCl) overnight at 4° C. Wells were washed four times with TBST (25 mM Tris/HCl pH 7.5 containing 150 mM NaCl and 0.1% (v/v) Tween 20). As a standard monoclonal AB the HIX1 anti-FIX (accurate) was used. Standard and samples were diluted in TBST containing 2%(w/v) BSA. The standard dilution series and appropriate dilutions of the samples were incubated on the ELISA-plate for 2 hours at room temperature. Plates were washed 4 times with TBST and incubated (2 h, RT) with 100 µl/well of a 1:25000 dilution (in TBST/1% BSA) of an anti-mouse IgG (Fc-specific) peroxidase conjugated antibody (Sigma, #A-0168) FIXa. Wells were washed 5 times with TBST and finally stained with 100 µl freshly prepared staining solution (10 ml 50 mM sodium citrate, pH 5 supplemented with 100 µl OPD (60 mg OPD/ml) and 10 µl 30% $H_2O_2$). The reaction was stopped by the addition of 50 ml $H_2SO_4$ and after 30 minutes the optical density was recorded at 492 nm and 620 nm in a Labsystems iEMS Reader MF™ microtiter plate reader employing GENESIS™ software.

Example 4

Figure 6A:
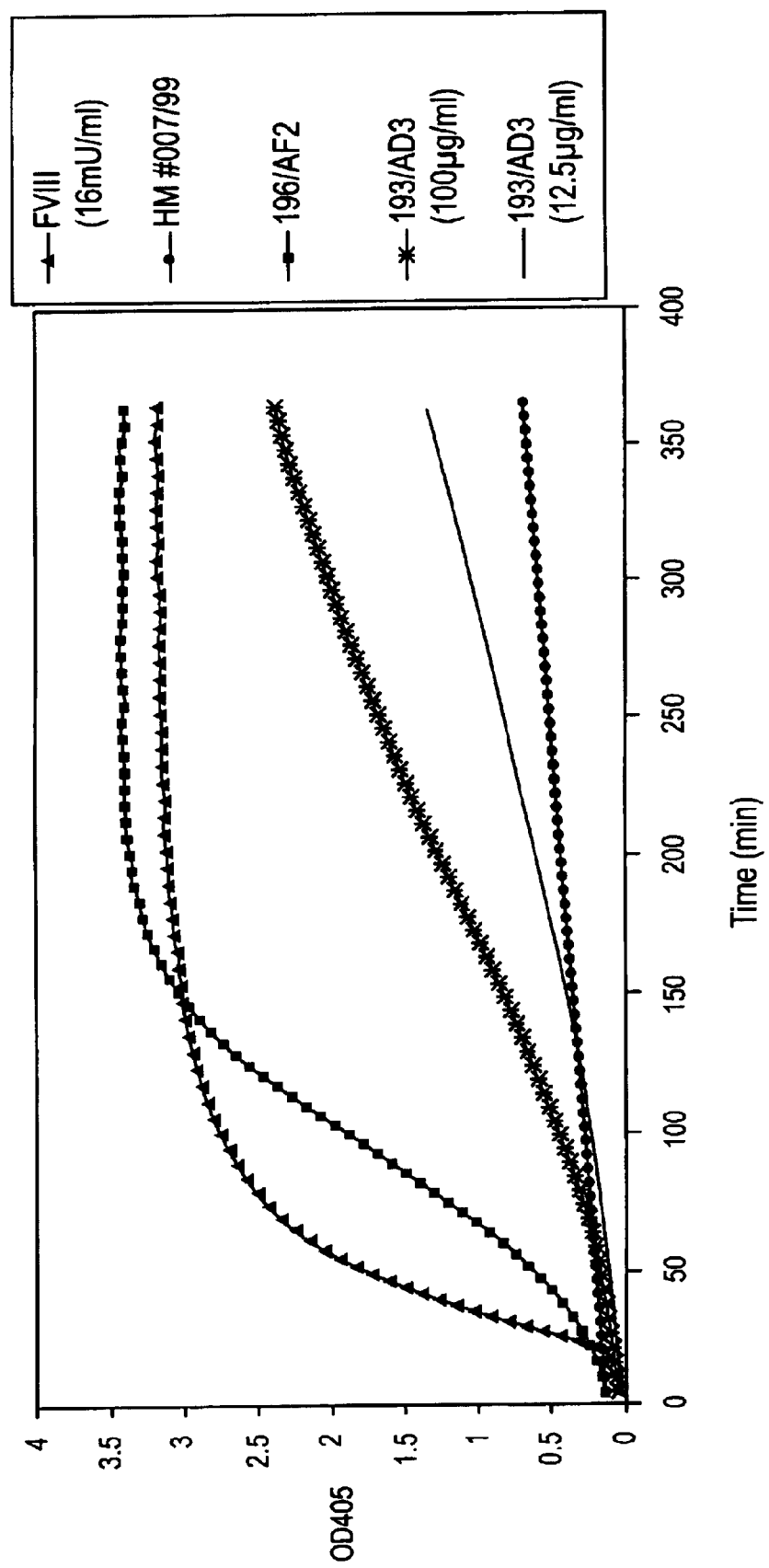
FIG. 6A shows the FVIII-like activity of the anti-FIX/FIXa-antibodies 193/AD3 and 196/AF2 compared to human FVIII, TBS buffer and cell culture medium. After a lag phase, both antibodies gave rise to chromogenic substrate cleavage, as judged by the increasing optical density.
Figure 6B:
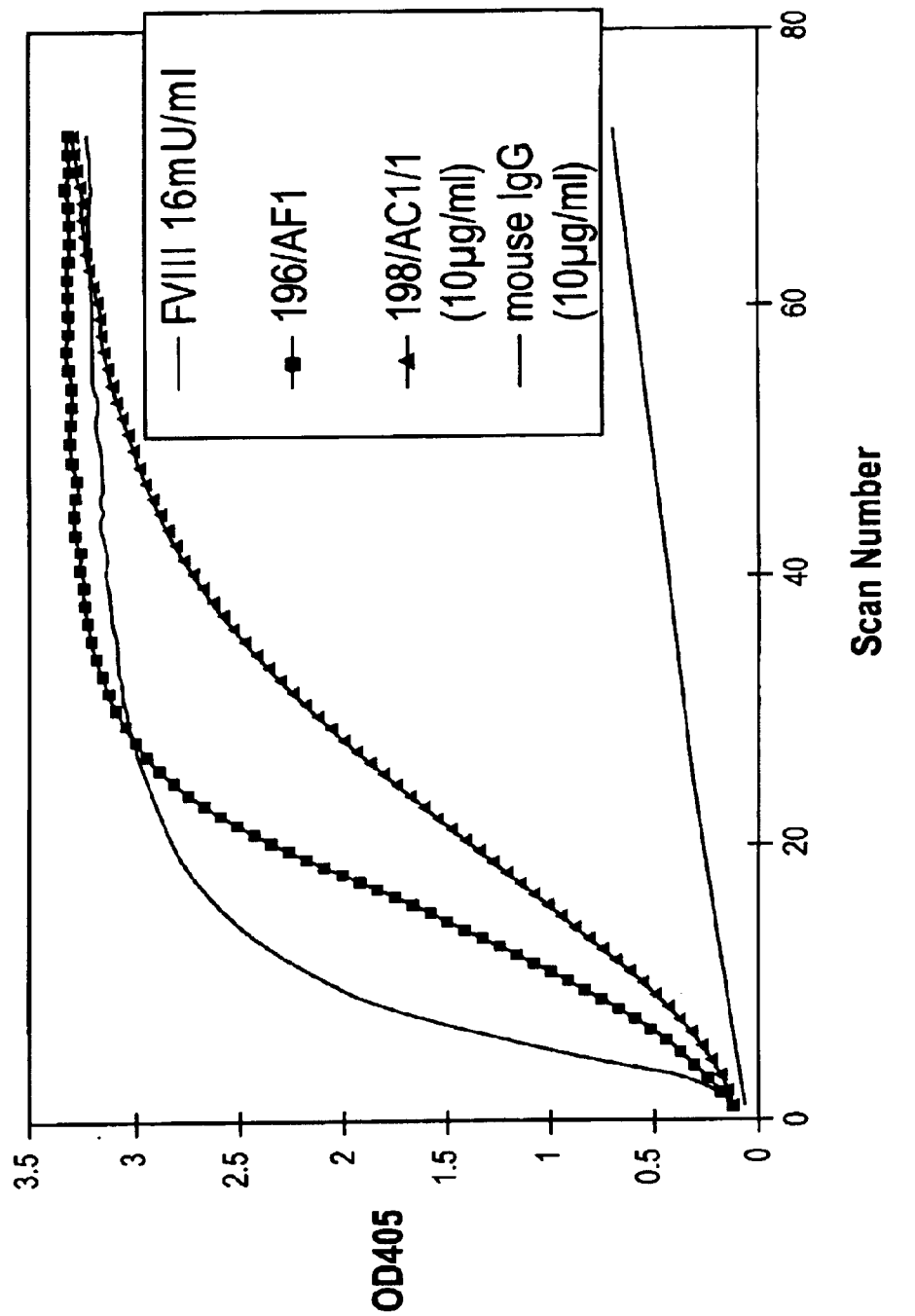
FIG. 6B shows a comparison of the chromogenic activity of factor VIII, 196/AF1, 198/AC1/1 and mouse-IgG.

Anti-FIX/FIXa Antibodies Exhibiting FVIII-like Activity in a Chromogenic FVIII Assay Several anti-FIX/FIXa antibody producing hybridoma clones were subcloned up to four times and the resulting monoclonal hybridoma cell line used to produce monoclonal antibody containing supernatant. IgG isotype antibodies derived from these supernatants were purified over affinity columns and dialyzed against TBS (see above). IgM antibodies were used as unpurified supernatant fractions. The following experiments were done with two sets of representative antibodies: 193/AD3 and 198/AC1/l (IgG isotype, the antibody 198/AC1/1 is a preparation from the parent 198/AC1 hybridoma clone, i.e. that a (frozen) vial containing 198/AC1 cells is cultivated and antibodies are produced. The supernatant is then used for these experiments.) and 196/AF2 and 196/AF1 (IgM isotype) (FIG. 6A and FIG. 6B). Briefly, 25 µl aliquots of monoclonal antibody containing sample (unpurified hybridoma supernatant or, where indicated, a certain amount of FIX specific antibody) were transferred to microtiter plate wells and warmed to 37° C. Chromogenic substrate (S-2222), synthetic thrombin inhibitor (I-2581), factor (F) IXa and FX were reconstituted in sterile water and FIXa/FX was mixed with phospholipids according to the supplier's protocol. Per reaction, 50 µl of the phospholipid/FIXa/FX solution were combined with 25 µl $CaCl_2$ (25 mM) and 50 µl of the substrate/inhibitor cocktail. To start the reaction, 125 µl of the premix were added to the monoclonal antibody solution in the microtiter plates and incubated at 37° C. Absorbance at 405 nm and 490 nm of the samples was read at various times (5 min to 6 h) against a reagent blank (cell culture medium instead of hybridoma supernatant) in a Labsystems iEMS Reader MF™ microtiter plate reader using GENESIS™ software.

The time course of FVIII-like activity exhibited by monoclonal antibodies 193/AD3 (IgG isotype) and 196/AF2 (IgM isotype) compared to human FVIII (12 and 16 mU/ml), TBS and to cell culture medium is shown in FIG. 6A. After a lag phase, both antibodies give rise to chromogenic substrate cleavage, as judged by the increasing optical density measurable at 405 nm wavelength.

The time course of FVIII-like activity exhibited by monoclonal antibodies 198/AC1/1 (IgG isotype, 10 µg/ml) and 196/AF1 (IgM isotype, unpurified supernatant) compared to human FVIII (16 mU/ml) and 10 µg/ml of mouse IgG is shown in FIG. 6B. After a lag phase, both antibodies give rise to chromogenic substrate cleavage, as judged by the increasing optical density measurable at 405 nm wavelength.

Example 5

FVIII-like Activity Exhibited by Anti-FIX/FIXa-antibodies Generates Factor Xa and is Phospholipid, FIXa/FX and $Ca^{2+}$ Dependent Factor VIII activity is usually determined with a chromogenic assay and/or an APTT-based clotting assay. Both types of assays rely on FVIIIa/FIXa-mediated factor Xa generation. In the case of a chromogenic FVIII assay, the factor Xa produced will subsequently react with a chromogenic substrate, which can be monitored spectroscopically, e.g., in an ELISA reader. In an APTT based clotting assay free factor Xa will assemble with FVa on a phospholipid surface in the so-called prothrombinase complex and activate prothrombin to thrombin. Thrombin in turn gives rise to fibrin generation and finally to clot formation. Central to the two assay systems is generation of factor Xa by the FVIIIa/FIXa complex.

To demonstrate that the FVIII-like activity exhibited by anti-FIX/FIXa-antibodies indeed generates factor Xa, the following experiment was carried out. Several 25 µl aliquots of unpurified hybridoma supernatant 196/AF2 (IgM isotype) were transferred to microtiter plate wells and warmed to 37° C. As a positive control, 16mU of Recombinate™ were diluted into hybridoma medium (196 HM 007/99) and treated exactly the same way as the hybridoma supernatant. As a negative control, plain hybridoma medium was used. Chromogenic substrate (S-2222), synthetic thrombin inhibitor (I-2581), factor IXa and FX were reconstituted in sterile water and FIXa/FX was mixed with phospholipids according to the supplier's protocol. Pefabloc Xa®, a factor Xa specific proteinase inhibitor (Pentapharm, LTD), was reconstituted with water to a final concentration of 1 mM/l. Per reaction, 5011 of the phospholipid/FIXa/FX solution were combined with 25 µl $CaCl_2$ (25 mM) and 50 µl of the substrate/thrombin-inhibitor cocktail. To start the reaction, 125 µl of the premix were added to the samples in the microtiter plates and incubated at 37° C. Where indicated, 35 µM Pefabloc Xa® were added. Absorbance at 405 nm and 490 nm was read at various times (every 5 minutes to 6 h) against a reagent blank (cell culture medium) in a Labsystems iEMS Reader MF™ microtiter plate reader employing the GENESIS™ software.

Figure 7A:
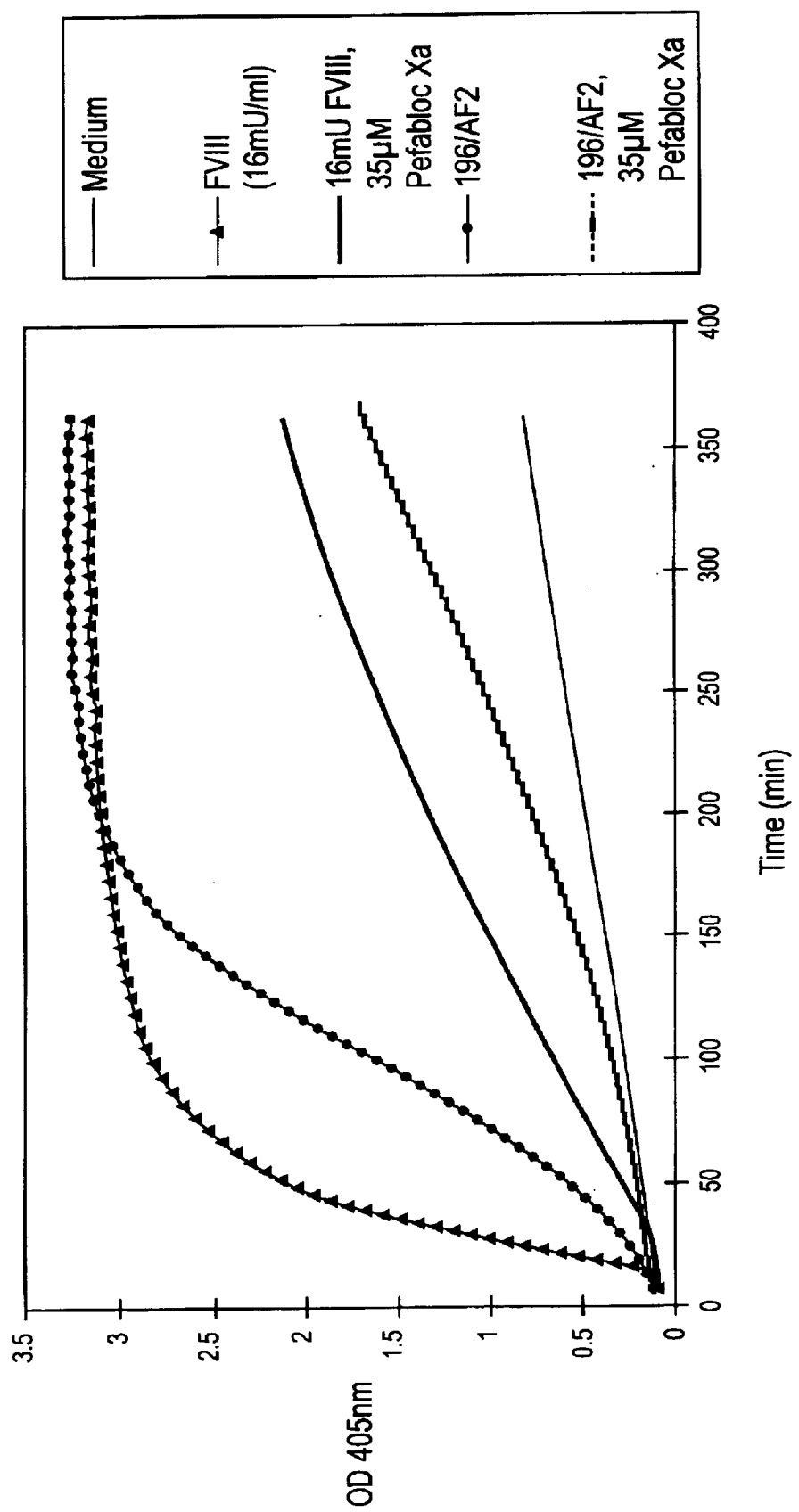
FIG. 7A shows a comparison of the kinetics of Factor Xa generation by Factor VIII and 196/AF2 with and without the addition of a Factor Xa specific inhibitor.

The results of the factor IXa stimulation by the FVIII-like activity exhibited by the IgM anti FIX/FIXa-antibody 196/AF2 in generating actor Xa as judged by the readily measurable cleavage of the chromogenic substrate S-2222 (compare "16 mU FVIII" and "196/AF2") is shown in FIG. 7A. Factor Xa activity is effectively blocked by the FXa specific inhibitor "Pefabloc Xa®" (compare "196/AF2" versus "196/AF2 351M Pefabloc Xa®") indicating that indeed FXa was generated.

Figure 7B:
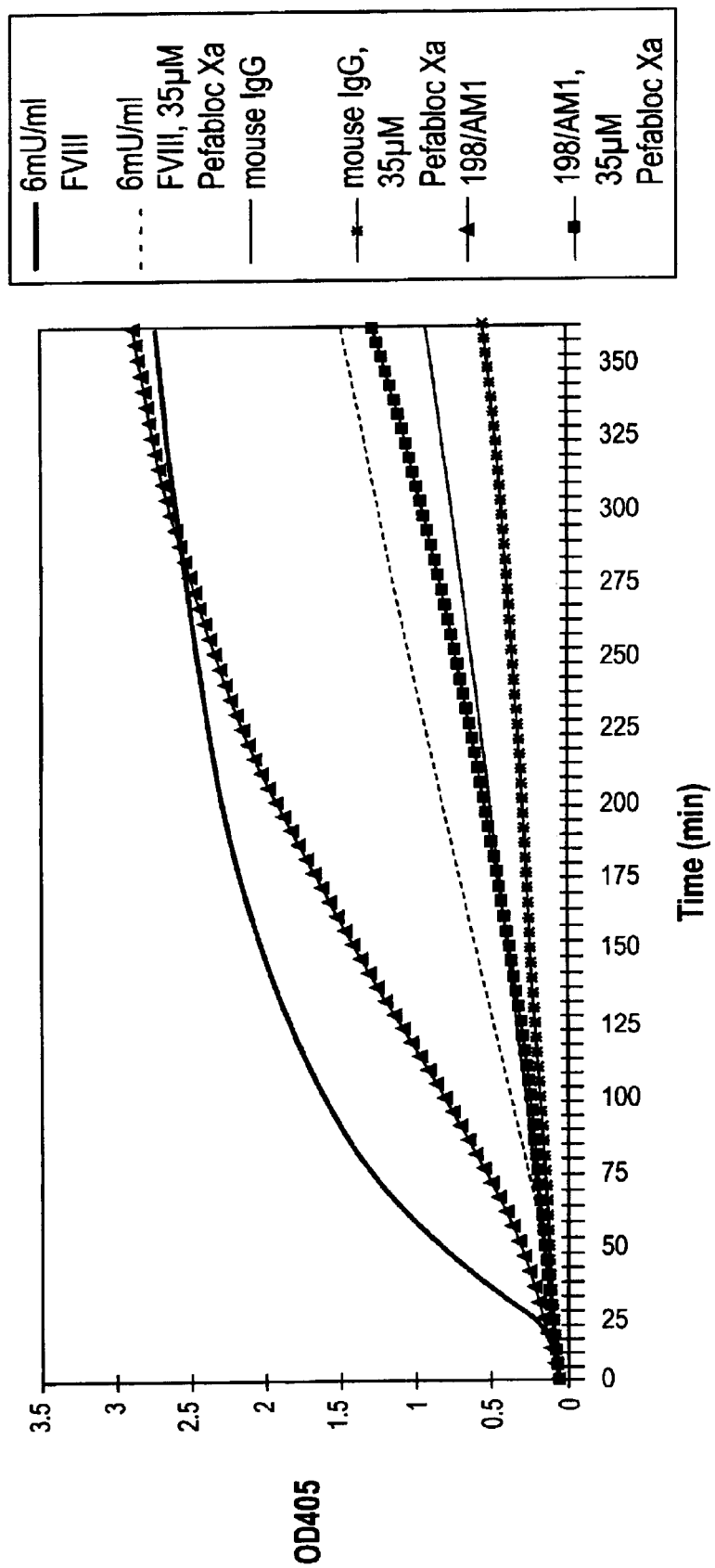
FIG. 7B shows a comparison of the kinetics of the Factor Xa generation by Factor VIII, mouse-IgG and anti-factor IX/IXa-antibody 198/AM1 with and without the addition of a factor Xa-specific inhibitor, Pefabloc Xa®.

The same experiment was performed using purified IgG preparations of clone 198/AM1 (FIG. 7B). Purified IgG was diluted in TBS to a final concentration of 0,4 mg/ml and 25 µl (i.e. a total of 10 µg), transferred to microtiter plate wells and warmed to 37° C. As a positive control, 6 mU plasma derived FVIII was used. 10 µg unspecific mouse IgG (Sigma, I-5381) served as a negative control. The assay was performed as described above.

Further experiments show the factor IXa stimulation by the FVIII-like activity exhibited by the IgG anti-FIX/FIXa-antibody 198/AM1 generates factor Xa as judged by the readily measurable cleavage of the chromogenic substrate S-2222 (FIG. 7B). Again factor VIII and antibody 198/AM1 generate FXa which is effectively blocked by the FXa specific inhibitor "Pefabloc Xa®". As a negative control, unspecific mouse IgG (Sigma, 15381) was assayed.

In another set of experiments, the dependence of the FVIII-like activity of either purified anti-FIX/FIXa-antibodies (IgM, FIG. 8A) or of unpurified antibodies derived from cell culture supernatants (IgG, FIG. 8B) on the presence of phospholipids (PL), FIXa/FX and $Ca^{2+}$ was demonstrated. Mouse IgG was used as a control (FIG. 8C). Factor VIII-like activity was assayed essentially as described above. When indicated, either the FIXa/FX mixture, the PL or $Ca^{2+}$ was omitted from the reaction. Absorbency at 405 nm and 490 nm of the samples was read at various times against a reagent blank (buffer instead of purified antibody) in a Labsystems iEMS Reader MF™ microtiter plate reader. The results are shown in FIG. 8A, FIG. 8B and FIG. 8C.

Figure 8A:
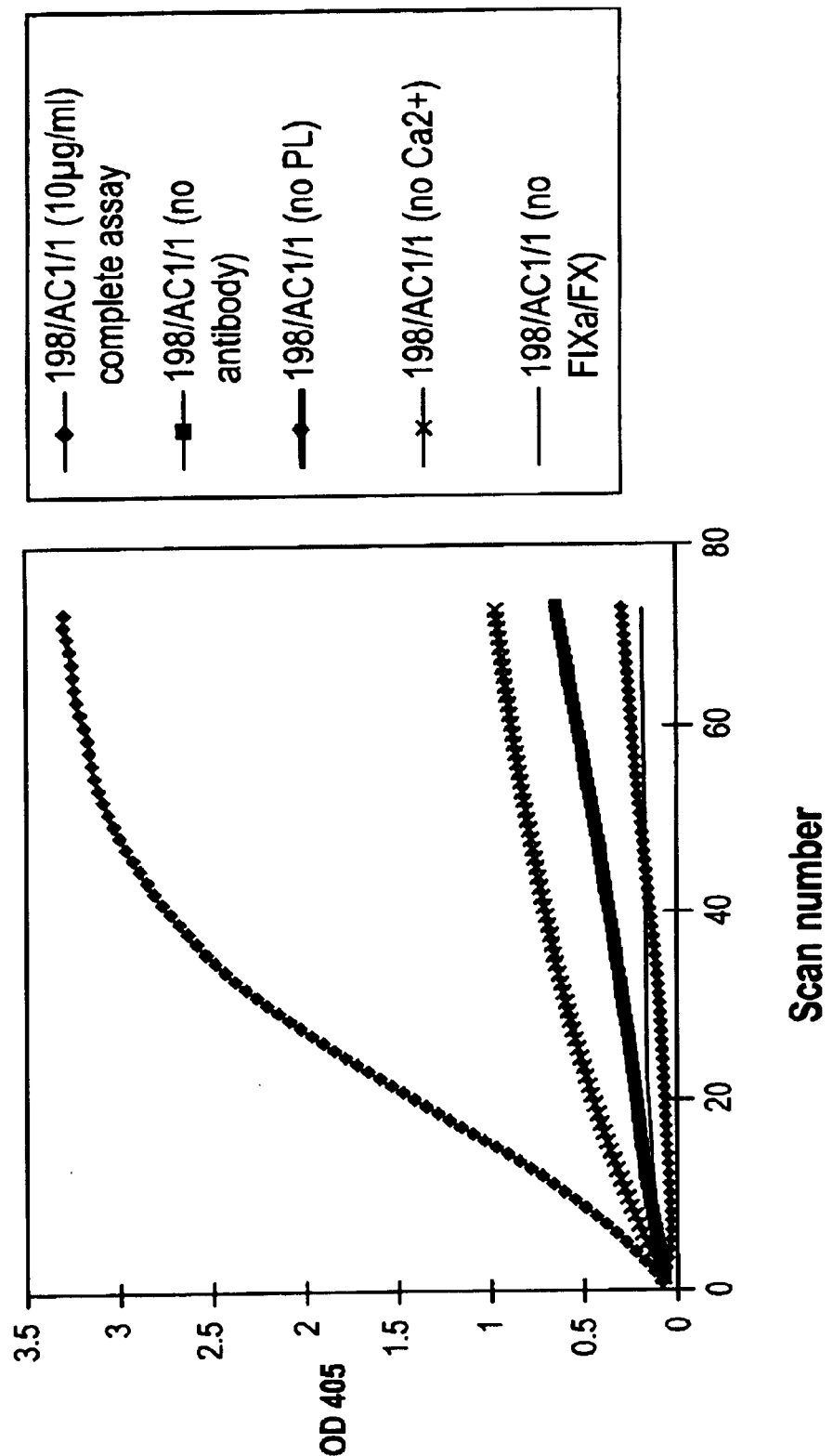
FIG. 8A shows a measurement of the dependence of the factor VIII-like activity of purified anti-factor IX/IXa-antibody 198/AC1/1 in the presence and absence of phospholipids, FIXa/FX and calcium ions.
Figure 8B:
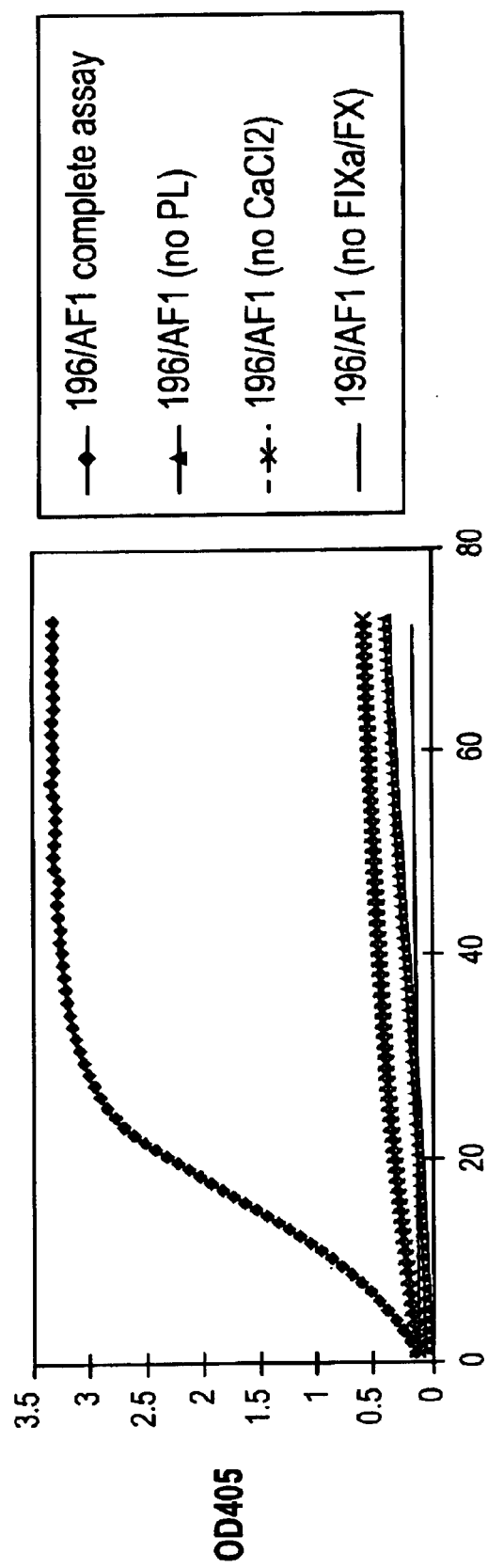
FIG. 8B shows a measurement of the dependence of FXa generation by anti-FIXa-antibody 196/AF1 in the presence of phospholipids, $Ca^{2+}$ in FIXa/FX.
Figure 8C:
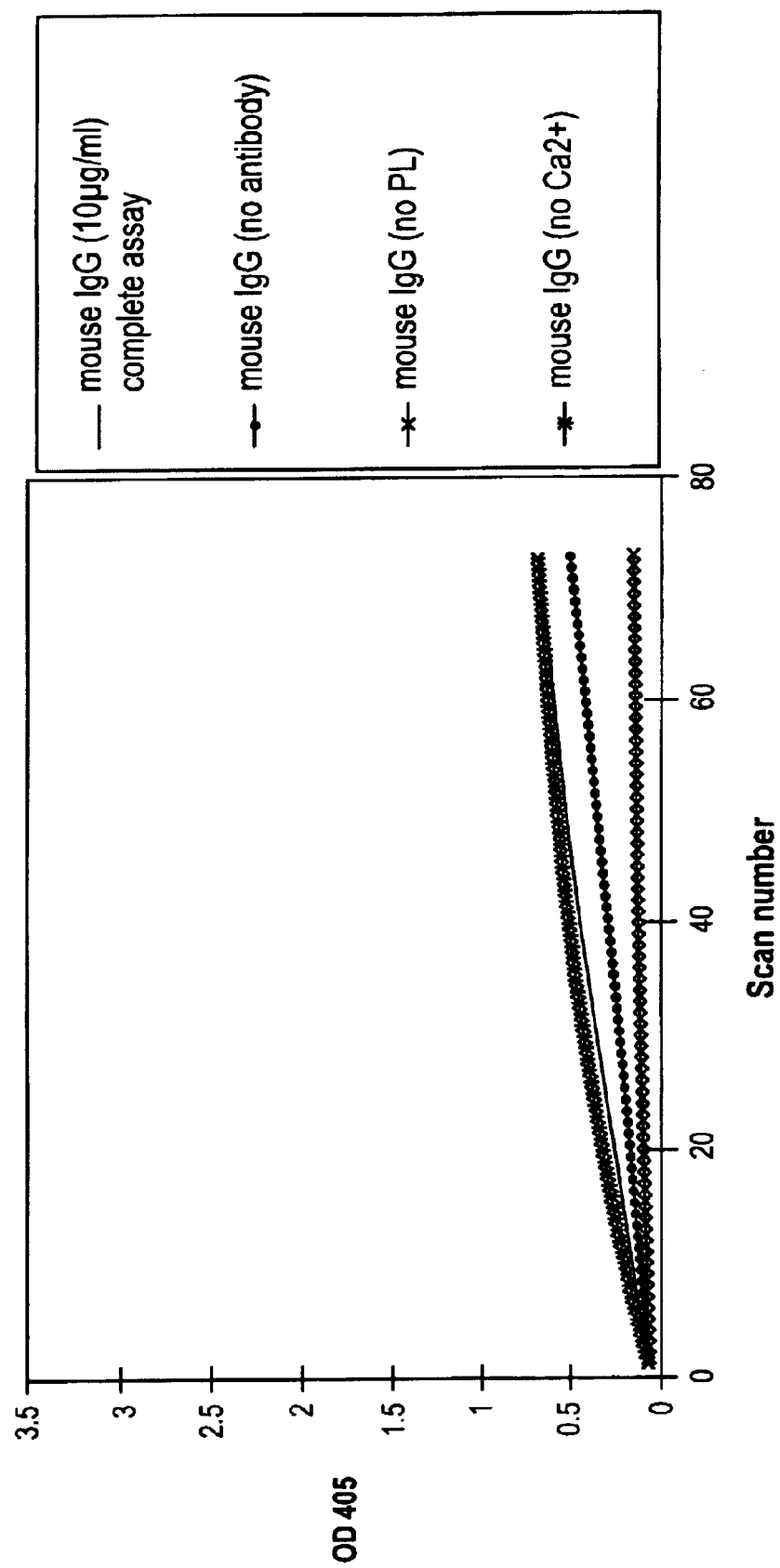
FIG. 8C shows the generation of FXa by unspecific mouse IgG antibody.

The dependence of the FVIII-like activity of purified anti-FIXa-antibody 198/AC1/1 (IgG isotype, concentration used throughout the assay was 10 µg/ml) on the presence of phospholipids (PL), FIXa/FX and $Ca^{2+}$ is further shown in FIG. 8A. As is easily recognizable, only the complete assay, including antibody, PL, $Ca^{2+}$, and FIXa/FX gives rise to a reasonable FXa generation. The dependence of the FVIII-like activity of cell culture supernatant containing unpurified IgM isotype anti-FIX/FIXa-antibody (196/AF1) on the presence of phospholipids, FIXa/FX and $Ca^{2+}$ is shown in FIG. 8B.

Again, as already shown for the purified IgG preparation (FIG. 8A), antibody 198/AC1/l, only the complete assay, including PL, $Ca^{2+}$, FIXa/FX, will give a reasonable amount of FXa generation. To demonstrate the specificity of the reaction, total IgG prepared from normal mouse plasma was assayed under the same conditions as above. The results are shown in FIG. 8C. No FVIII-like activity could be detected. There is, as expected, no activity detectable in the absence of phospholipids, FIXa/FX and $Ca^{2+}$. All experiments were done in a microtiter plate and the OD405 was scanned every 5 minutes for 6 h.

Example 6

Certain anti-FIX/FIXa-antibodies are procoagulant in the presence of FIXa

During normal hemostasis, FIX becomes initially activated either by the tissue factor (TF)/factor VIIa pathway or later on by activated factor XI (FXIa). Subsequent to its activation, FIXa associates on the platelet surface in a membrane bound complex with activated FVIII. Factor IXa by itself has little or no enzymatic activity towards FX, but becomes highly active in the presence of FVIIIa. To demonstrate that certain anti-FIX/FIXa antibodies have FVIII-like activity and hence are procoagulant in a FVIII deficient human plasma, the following experiment was carried out. Different amounts of antibody 193/AD3 or mouse IgG (as a control) were used in a standard aPTT based one stage clotting assay. Briefly, 100 µl of antibody-containing samples were incubated with 100 µl of FVIII deficient plasma (DP) and with 100 µl of DAPTTIN (PTT Reagent for determining activated Thromboplastin Time; IMMUNO AG) reagent, in a KC10A clotting analyzer. Where indicated, a total amount of 50 ng activated FIX was included in the reaction mixture. After a 4 minute incubation, the reaction was started by the addition of 100 µl CaCl$_2$ (25 mM). The results are shown in Table 1 and FIG. 9.

| µg AB | clotting time (sec) | |
| --- | --- | --- |
|  | 193/AD3 50 ng FIXa | mouse IgG 50 ngFIXa |
| 9 | 101.6 | 102.5 |
| 4.5 | 95.6 | 103.2 |
| 2.25 | 93.1 | 103.2 |
| 1.8 | 93.7 | 101.9 |
| 1.35 | 91.4 | 103.4 |
| 0.9 | 94.4 | 102.2 |
| 0.45 | 98.1 | 101.9 |
| 0.34 | 97.1 | 103.9 |
| 0.23 | 99.3 | 103.7 |

Table 1: Clotting times of FVIII deficient plasma in an APTT based clotting assay employing various amounts of procoagulant (193/AD3) and control antibody (mouse IgG) in the presence of 50 ng activated FIX (0.01UFIX). The molar ratio of antibody in the reaction and activated FIX is 10:1. The molar ratio between antibody and total FIX (FIX and FIXa, assuming that human FVIII deficient plasma contains 1 U (5% g) FIX) varies between 6:1 (9% g antibody in reaction) and 1:6 (0.23% g antibody in reaction). At the optimal shortening of the clotting time, the molar ratio between antibody and total FIX is 1:1. The clotting time without the addition of FIXa is in the range of 120 seconds.

Figure 9:
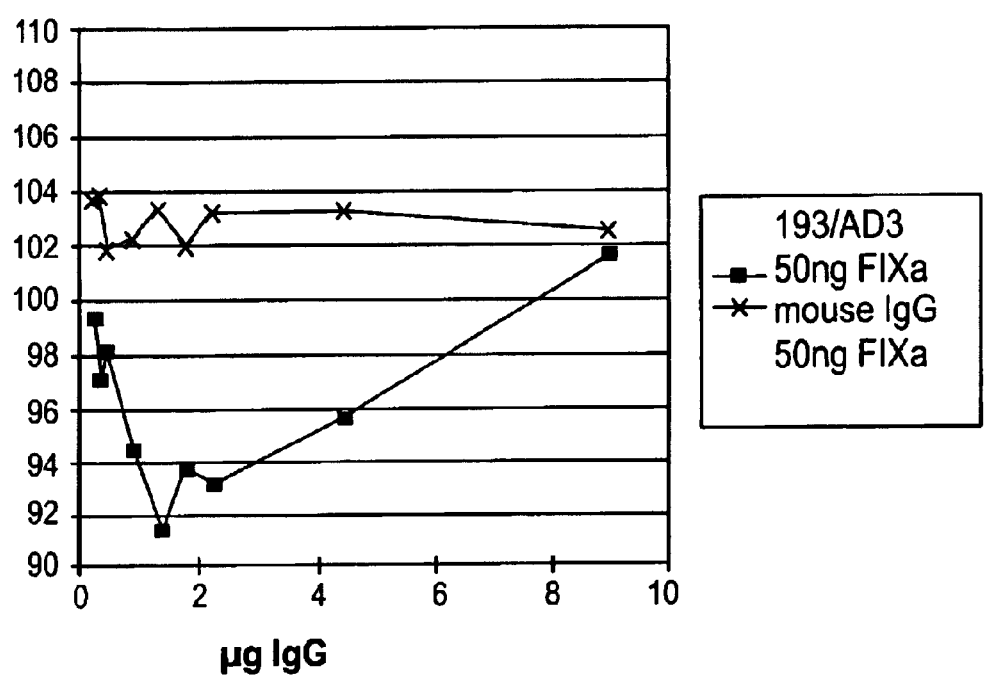
FIG. 9 is a graphical representation of the coagulation times of Factor VIII-deficient plasma in an APTT assay by using various concentrations of anti-factor IX/IXa-antibody 193/AD3.

FIG. 9 is a graphical representation of the clotting times of FVIII deficient plasma in an aPTT based clotting assay employing various amounts of procoagulant (193/AD3) and control (mouse IgG) antibody in the presence of 50 ng activated FIX. There is a clear dose-dependent reduction of the clotting time in samples supplemented with antibody 193/AD3. These results imply that antibody 193/AD3 is procoagulant in the presence of FIXa.

Example 7

Anti-FIX/FIXa-antibodies are Procoagulant in the Presence of FVIII Inhibitors and FIXa A severe complication of the standard FVIII substitution therapy is the development of alloantibodies directed against FVIII, leading to FVIII neutralization and a condition where the patient's blood will not clot.

Figure 10A:
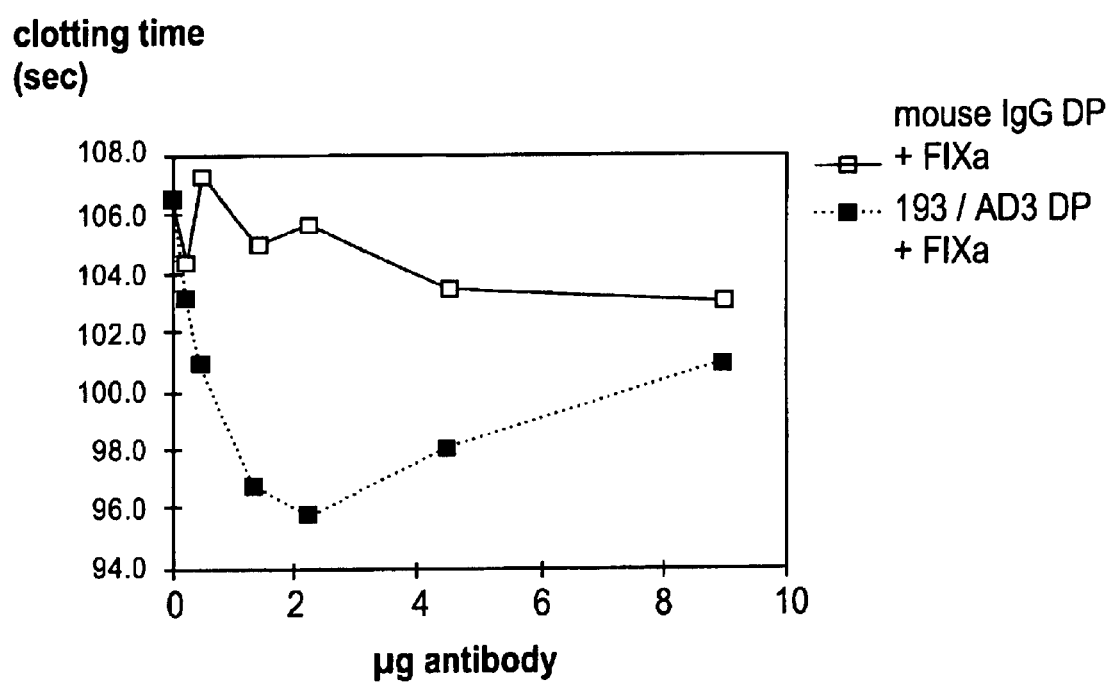
FIG. 10A shows that in the presence of Factor IXa, antibody 193/AD3 leads to a reduction in the coagulation time of factor VIII-deficient plasma.
Figure 10B:
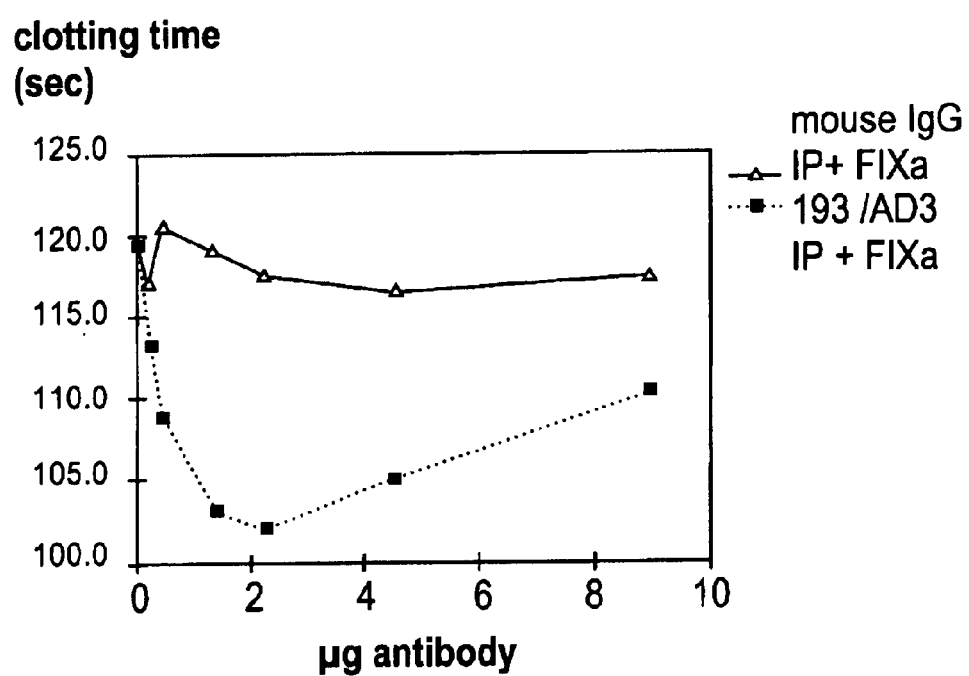
FIG. 10B shows a dose-dependent reduction of the clotting time by antibody 193/AD3 in the presence of factor IXa- and factor VIII-inhibitors.

To demonstrate that certain anti-FIXa-antibodies have FVIII-like activity even in the presence of FVIII inhibitors, the following experiment was carried out. Different amounts of antibody 193/AD3 or, as a control, mouse IgG were used in a standard APTT based one-stage clotting assay. Briefly, 100 µl antibody samples were incubated with either 100 µl of FVIII deficient plasma (FIG. 10A) or FVIII inhibitor plasma (inhibitor potency 400 BU/ml), FIG. 10B) as well as with 100 µl of DAPTTIN reagent, in a KC10A clotting analyzer. In addition, a total amount of 50 ng activated FIXa was included in the reaction mixture. After a 4 minute incubation, the reaction was started by the addition of 100 µl CaCl$_2$ (25 mM). To ensure equal conditions, the experiments employing FVIII deficient plasma and FVIII inhibitor plasma were done side by side. The results are shown in FIGS. 10A and 10B. As already shown in Example 6, there is a clear dose-dependent reduction of the clotting time in samples supplemented with antibody 193/AD3 in the presence of FVIII inhibitors.

Example 8

Anti-FIX/FIXa-antibodies are Procoagulant in the Presence of Defective FVIII and FIXa To demonstrate that certain anti-FIXa-antibodies have FVIII-like activity in the presence of defective FVIII, the following experiment may be carried out. Increasing amounts of antibody 193/AD3 or, as a control, mouse IgG are used in a standard aPTT-based one stage clotting assay. In this clotting assay, a hemophilia A patient's plasma having very low clotting activity due to the presence of defective FVIII (DF8) is used. Briefly, 100 µl antibody samples are incubated with either 100 µl of DF8 plasma or FVIII deficient plasma as well as with 100 µl of DAPTTIN reagent, in a KC10A clotting analyzer. In addition, a total amount of 50 ng activated FIXa is included in the reaction mixture. After a short incubation, the reaction will be started by the addition of 100 µl CaCl$_2$ (25 mM). To ensure equal conditions, the experiment employing FVIII deficient plasma and DF8 plasma is done side by side.

Example 9

Anti-FIX/FIXa-antibodies with Procoagulant Activity in the Presence of FIXa Distinguish Between Human and Bovine FIXa FIX/FIXa specific monoclonal antibodies selected from the 198$^{th}$ fusion experiment were purified from the respective hybridoma supernatant and quantified as described in Example 3. These antibodies were analyzed in a modified one-stage clotting assay (as described in Example 6) and some showed procoagulant activity.

The chromogenic activity of these antibody preparations was measured in the following FXa generation kinetic assay: 10 µg of monoclonal antibody (in 25 µl) were transferred to microtiter plate wells and warmed to 37° C. Chromogenic substrate (S-2222), synthetic thrombin inhibitor (I-2581), factor IXa and FX were reconstituted in sterile water and FIXa/FX (both bovine) were mixed with phospholipids according to the supplier's protocol. Per reaction, 50 µl of the phospholipid/FIXa/FX solution were combined with 25 µl CaCl$_2$ (25 mM) and 50 µl of the substrate/inhibitor cocktail. To start the reaction, 125 µl of the premix were added to the monoclonal antibody solution in the microtiter plates and incubated at 37° C. Absorbance at 405 nm and 490 nm of the samples was read at various times (5 min to 2 h) against a reagent blank (25 ml TBS instead of monoclonal antibodies) in a Labsystems iEMS Reader MF™ microtiter plate reader using GENESIS™ software. In parallel, the same reactions were performed except that 50 ng human FIXa were added per reaction. Those antibodies that showed procoagulant activity had no chromogenic activity in the case of bovine FIX, but displayed high activity when human FIXa was present.

Figure 11:
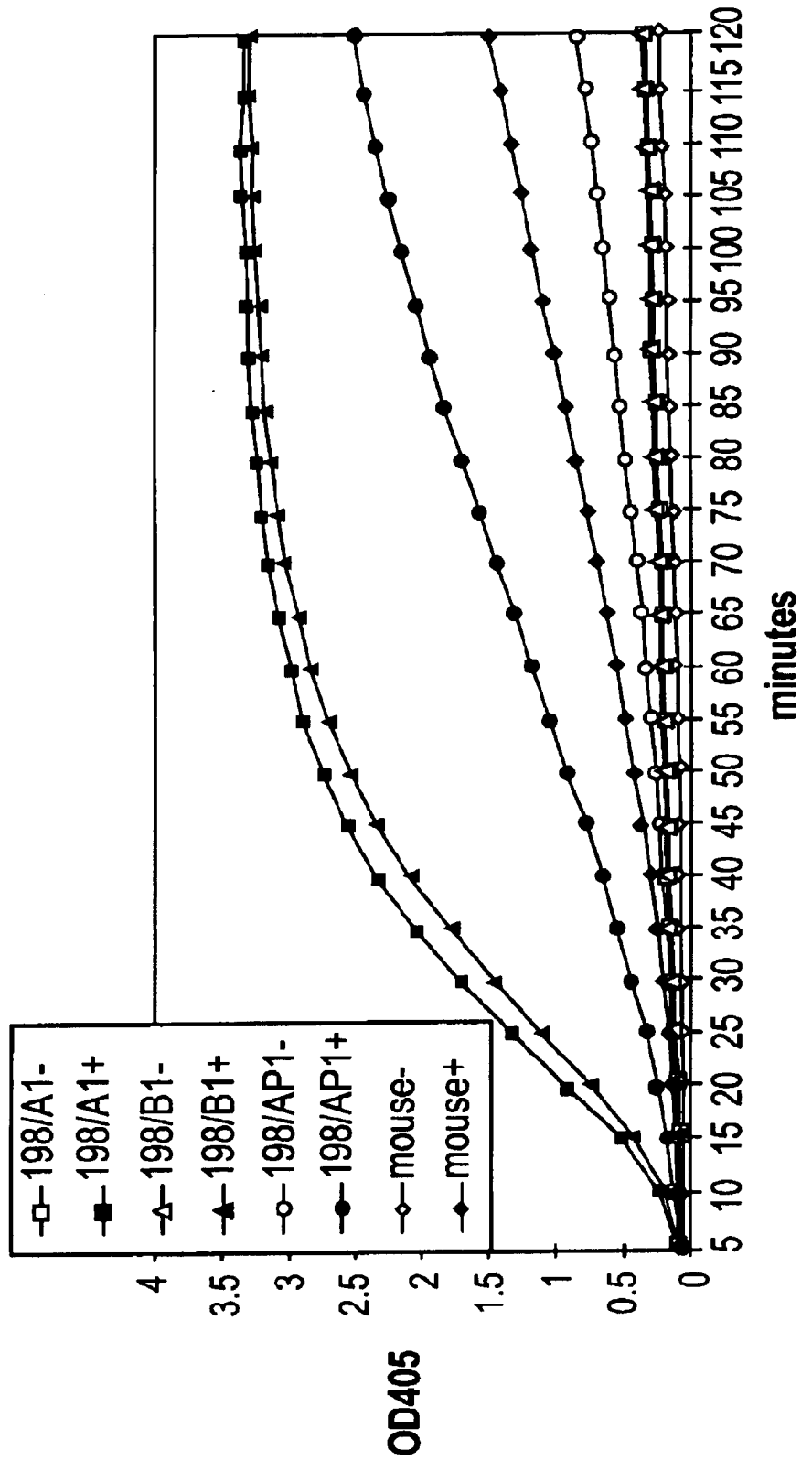
FIG. 11 shows the chromogenic activity of antibodies 198/A1, 198/B1 and 198/AP1 in the presence and absence of human FIXaβ.

FIG. 11 shows the time course of the FVIII-like activity exhibited by the monoclonal antibodies 198/A1, 198/B1 and 198/AP1 with (+) and without (−) addition of 50 ng human FIXaβ. Non-specific polyclonal mouse IgG was used as a control. 198/A1 and 198/B1 show procoagulant activity (similar as 193/AD3 in example 6) whereas 198/AP1 does not. Antibody 198/BB1 had the same activity pattern (data not shown).

Further monoclonal antibodies selected from the 198$^{th}$ fusion experiment include 198/Dl (ECACC NO. 99121616), 198/T2 (ECACC No. 99121617), 198/G2 (ECACC No.9912118), 198/U2 (ECACC No. 99121620).

Example 10

Structure and Procoagulant Activity of Antibody Derivatives Derived from Anti-FIX/FIXa-antibodies; Subcloning Antibody Variable Domains from Hybridoma Cell Lines 193/AD3, 193/K2, 198/A1 and 198/B1 (Clone AB2)

Cloning procedure: Messenger RNA was prepared from $1 \times 10^{-6}$ hybridoma cells of the respective cell line (either 193/AD3, 193/K2, 198/A1 or 198/B1 (clone AB2)) employing the "QickPrep® Micro mRNA Purification Kit" (Pharmacia) according to the manufacturer's instructions. The corresponding cDNA was produced by retro transcription of mRNA using the "Ready-To-Go-You-Prime-First-Strand Beads kit" (Pharmacia) according to the manufacturer's instructions. Heavy and light chain encoding sequences were converted to the corresponding cDNA employing a set of primers. To reverse transcribe heavy chain-specific mRNA (VH), an equimolar mixture of the oligonucleotides MOCG1-2FOR (5' CTC AAT TTT CTT GTC CAC CTT GGT GC 3') (SEQ.ID.NO. 1), MOCG3FOR (5'CTC GAT TCT CTT GAT CAA CTC AGT CT 3') (SEQ.ID.NO. 2) and MOCMFOR (5' TGG AAT GGG CAC ATG CAG ATC TCT 3') (SEQ.ID.NO. 3) was used (RTmix1). In the same reaction tube, light chain-specific cDNA (VL) was synthesized using primer MOCKFOR-(5'CTC ATT CCT GTT GAA GCT CTT GAC 3') (SEQ.ID.NO. 4).

The coding sequences for VH were amplified by PCR using the primer-sets depicted in FIG. 12 and the specific cDNA, derived from the reverse transcription mixture (RTmix1) described above, as the template. VK-chain genes were amplified using the primer sets depicted in FIG. 13 and also employing Rtmix1 as a template. The VF-PCR product was cleaved SfiI-AscI and inserted into SfiI-AscI digested vector pDAP2 (GeneBank accession no.: U35316). The pDAP2-VH constructs obtained thereby were named pDAP2-193AD3/VH, pDAP2-198A1/VH, pDAP2-198AB2/VH (derived from antibody 198/B1) and pDAP2-193/K2/VH, respectively. The plasmids were subsequently cleaved with AscI-NotI and the corresponding AscI-NotI digested VK-gene PCR product was inserted. The resultant vectors were designated pDAP2-193/AD3scFv, pDAP2-198/A1scFv, pDAP2-198/AB2scFv (derived from antibody 198/B1) and pDAP2-193/K2scFv and code for the VH-gene and the VL-gene of the monoclonal antibodies 193/AD3, 198/A1, 198/AB2 (derived from antibody 198/B1) and 193/K2. Heavy and light chains are linked by the coding sequence for an artificial, flexible linker ($G_4SGGRASG_4S$ (SEQ ID NO:111); Engelhardt et al., 1994) and enables expression of the scFv variant of the respective antibody.

In FIG. 14, the DNA and the deduced protein sequence of the scFv derived from the hybridoma cell line 193/AD3 are depicted. Nucleotides 1 to 357 code for the heavy chain variable domain, nucleotides 358 to 402 code for the artificial flexible linker and nucleotides 403 to 726 code for the light chain variable region. The protein sequence of the CDR3 region of the heavy chain has the sequence YGNSPKGFAY (SEQ ID NO:5) and is given in bold letters. The artificial linker sequence ($G_4SGGRASG_4S$; SEQ ID NO:111) is shown.

In FIG. 15, the DNA and the deduced protein sequence of the scFv derived from the hybridoma cell line 193/K2 is shown. Nucleotides 1 to 363 code for the heavy chain variable domain, nucleotides 364 to 408 code for the artificial flexible linker, and nucleotides 409 to 747 code for the light chain variable region. The protein sequence of the CDR3 of the heavy chain has the sequence DGGHGYGSSFDY (SEQ ID NO:6), and is given in bold letters. The artificial linker sequence ($G_4SGGRASG_4S$; SEQ ID NO:111) is shown.

In FIG. 16, the DNA and the deduced protein sequence of the scFv derived from the hybridoma cell line 198/AB2 (derived from antibody 198/B1) are depicted. Nucleotides 1 to 366 code for the heavy chain variable domain, nucleotides 367 to 411 code for the artificial flexible linker, and nucleotides 412–747 code for the light chain variable region. The protein sequence of the CDR3 region of the heavy chain has the sequence EGGGFTVNWYFDV (SEQ ID NO:7) and is given in bold letters. The artificial linker sequence ($G_4SGGRASG_4S$; SEQ ID NO:111) is also shown.

In FIG. 17, the DNA and the deduced protein sequence of the scFv derived from the hybridoma cell line 198/A1 are depicted. Nucleotides 1 to 366 code for the heavy chain variable domain, nucleotides 367 to 411 code for an artificial flexible linker, and nucleotides 412–747 code for the light chain variable region. The protein sequence of the CDR3 region of the heavy chain has the sequence EGGGYYVNWYFDV (SEQ ID NO:8) and is given in bold letters. The artificial linker sequence ($G_4SGGRASG_4S$; SEQ ID NO:111) is also shown.

Example 11

Procoagulant Activity of Peptides Derived from CDR3 Regions of Anti-FIX/FIXa-Antibodies In principle, the antibody molecule can be envisioned as a biological device for the presentation of a combinatorial array of peptide elements in three dimensional space (see Gao et al., 1999, PNAS, 96:6025). Therefore, an antibody (or an antibody derivative, e.g. scFv, Fab, etc.) can be used either as a tool for the detection of functionally important domains of a specific target protein, or on the other hand, for the delineation of amino acid sequences specifically mediating certain interactions, i.e. activating or enhancing the activity of FIXa towards the physiological substrate FX. The latter process has led to the evaluation of a number of heavy chain CDR3 region (CDR3H) derived peptide sequences as FIXa enhancing agents.

Enhancing the procoagulant activity of peptides which exhibit such activity may be accomplished through sequence variation within the peptide regions critical for mediating the FIXa activity enhancement. As a possible step towards peptide sequences with enhanced procoagulant activity, the binding site of an antibody, i.e. 198/A1 or 198/B1, on the FIXa molecule is mapped by employing sequence comparison analyses, competitive binding assays, Western blot analyses and competitive ELISA analyses. Since the crystal structure of FIX is known, molecular modeling is subsequently used to improve the fitting of i.e. 198/B1 derived peptides in the 198/B1 binding site on human FIXa.

On the other hand, methodical mutational analysis of a given peptide sequence such as 198/A1 or 198/B1 CDR3H derived peptide sequences by, e.g., "alanine scanning mutational analysis" allows for the identification of peptide residues critical for procoagulant activity. Another way to improve the activity of a certain peptide sequence is the use of peptide libraries combined with high throughput screening.

The antigen binding site of an antibody is derived from the juxtaposition of the six "complement determining regions (CDR's)" at the N-terminal end of the VL-HL dimer (or Fv region). The contribution of a single CDR to the antibody specificity for a given antigen may vary considerably, but in general it is thought that the CDR3 region of the heavy chain (CDR3H) is of special influence, i.e. the particular protein sequence of $CDR3_H$ region may be highly important for antigen recognition. The length of CDR3H regions has been reported to vary considerably and is in the range of 4–25 amino acids (Borrebaeck, p. 16).

An example of a methodical mutational analysis of peptide sequences is given below. To improve the solubility/procoagulant efficacy of peptides derived from the CD3-region of anti FIX/FIXa antibodies, the N-terminal as well as the C-terminal amino acid sequences were changed. In addition, a series of mutated peptides was constructed and analyzed.

The principle of such a study is exemplified by a series of peptides derived from CDR3H region of antibodies 198/A1 and 198/B1. The original peptide A1 (see table 2) is derived from the CDR3H region of antibody 198/A1 and peptide B1 is derived from the CDR3H region of antibody 198/B1, respectively (see example 10, FIGS. 16 and 17). The term "scrambled version" means that a peptide has the same amino acids but in random order.

FVIII assay was developed (see examples 2 and 4). The basic principle is, that without a cofactor, FIXa will have very limited activity towards its natural substrate FX. Only in the presence of a substance having FIXa activation properties, i.e. FVIII or a substance exhibiting FVIII-like activity, a substantial amount of FXa is produced by cleavage of FX through the FIXa/activator complex. The amount of FXa generated is monitored by cleavage of a chromogenic substrate. The principle of the revised chromogenic assay is described for two representative peptides: A1/3 and A1/5 (Table 2). Briefly, 25 μl aliquots of peptide stock solution (in imidazole buffer (IZ) 50 mM imidazole, 100 mM NaCl, pH7.2) were transferred to microtiter plate wells and warmed to 37° C. Chromogenic FXa substrate (S-2222), synthetic thrombin inhibitor (I-2581), bovine FIXa and bovine FX were reconstituted in sterile water and FIXa/FX mixed with phospholipids according to the supplier's protocol. Since the peptides do not react with bovine FIXa, (which comes as a mixture with bovine FX in the Test Kit) 2,9 nM (in most cases 2.3 nM) human FIXa (ERL) were added (see Example 11, FIG. 19). Per reaction, 50 μl of the phospholipid/FIXa/FX solution were combined with 251 $CaCl_2$ (25 mM) and 50 μl of the substrate/inhibitor cocktail. To start the reaction, 125 μl of the premix were added to the

| Peptide | Sequence | Amino-acids | MW (D) | pI | Remark |
|---|---|---|---|---|---|
| A1 | EGGGYYVNWYFDV (SEQ ID NO:8) | (13aa) | 1569 | 7.2 | Decreased solubility |
| A1/1 | VYGFGWGYEVNDY (SEQ ID NO:10) | (13aa) | 1569 | 7.1 | Scrambled version of A1, |
| A1/2 | EEEEGGGYYVNWYFDEEE (SEQ ID NO:11) | (18aa) | 2244 | 5.8 | Acidic pI, soluble, |
| A1/3 | RRREGGGYYVNWYFDRRR (SEQ ID NO:12) | (18aa) | 2407 | 9.9 | Basic pI, soluble, |
| A1/4 | EYGEGYGEVNEYDEFEWE (SEQ ID NO:13) | (18aa) | 2244 | 5.8 | Scrambled version of A1/2 |
| A1/5 | VRYRNRYRWGYRGRFGDE (SEQ ID NO:14) | (18aa) | 2407 | 9.9 | Scrambled version of A1/3 |
| A1/3-scr3 | RRRGEYGVYWNGDFYRRR (SEQ ID NO:15) | (18aa) | 2407 | 9.9 | Scrambled version of A1/3 |
| A1/3-Rd | RdRdRdEGGGYYVNWYFDRdRdRd | (18aa) | 2407 | 9.9 | Peptide A1/3 but substitute D-Arg for L-Arg |
| A1/3-Rd-srmb | RdRdRdGEYGVYWNGDFYRdRdRd | (18aa) | 2407 | 9.9 | Scrambled version of A1/3-Rd |

Table 2

List of a series of antibody 198/A1 derived peptizes. Listed are the length of the peptide (aa, amino acids #), the calculated molecular weight (MW, in Dalton (D) and the statistical isoelectric point (pI).D-Arg is abbreviated as Rd.

In a first series of experiments we improved the solubility of the original CDR3H peptide sequence (A1; EGGGYYVNWYFDV; SEQ ID NO:8) by removing the C-terminal Val residue and adding several charged residues at the N— as well as the C-terminal end of the peptide. The resulting peptides, A1/2 (acidic pI), A1/3 (basic pI) and their respective scrambled versions A1/4, A1/5 and A1/3scr3 were readily soluble in a variety of buffer systems at physiological pH.

To analyze the FVIII-like (FIXa activating) activity of the peptides, an assay system based on a commercial available peptide solution in the microtiter plate and incubated at 37° C. Absorbance at 405 nm and 490 nm of the samples was read at various times (5 min to 2 h) against a reagent blank in a Labsystems iEMS Reader MF™ microtiter plate reader using GENESIS™ software.

The result of this experiment are shown in Example 11, FIG. 18. Peptide A1/3 induced a readily measurable FXa generation in the presence of 2.9 nM human FIXa, whereas the scrambled version A1/5 was inactive. In addition, the acidic peptide A1/2 as well as the scrambled versions A1/4 and A1/3-scr3 did not give any significant chromogenic activity when tested under comparable conditions (data not shown). To prove that the peptide A1/3 like the parental antibody 198/A1 does not react with bovine FIXa and FX the experiment shown in FIG. 19 was done. The peptide A1/3 was incubated as described above with (A1/3 (24 µM), +hFIXa) and without (A1/3 (24 µM), w/o hFIXa) 2.3 nM human FIXa (hFIXa). In a control experiment we added plain dilution buffer (IZ) supplemented with 2.3 nM hFIXa to the reaction mixture. As shown in FIG. 19, the reaction takes place only in the presence of human FIXa.

FIG. 18 demonstrates the chromogenic FVIII-like activity of peptide A1/3 in the presence of 2.9 nM human FIXa (hFIXa). The scrambled version of peptide A1/3, peptide A1/5 does not give rise to any FXa generation. FIG. 19 demonstrates the dependence of the chromogenic FVIII-like activity of peptide A1/3 on the presence of human FIXa (hFIXa). In the absence of human FIXa, peptide A1/3 does not give rise to any FXa generation. The buffer control, plain imidazole buffer is designated IZ.

The peptides were also analyzed for their potential to reduce the clotting time in a FVIII deficient plasma. The aPTT based one stage clotting assay was essentially done as described (see example 6). Clotting times (time from starting the reaction to the "clot"-formation were compared either against FVIII, a buffer control (IZ) or a control peptide (scrambled version). The results of two typical clotting experiments done with two different aPTT reagents (DAPTTIN and Pathromtin SL) are shown in table 3A and table 3B.

| | peptide conc. | w/o FIXa sec | w/o FIXa sec | average sec | 2.2 nM FIXa sec | 2.2 nM FIXa sec | average sec |
|---|---|---|---|---|---|---|---|
| Exp. 1 | | | | | | | |
| IZ | 0 | 107.7 | 106.8 | 107 | 93.1 | 94.5 | 94 |
| A1/3 | 15 µM | 78.2 | 77.1 | 78 | 59.3 | 59.9 | 60 |
| | 12.5 µM | 80.2 | 80.6 | 80 | 60.2 | 58.9 | 60 |
| | 7.5 µM | 97.8 | 97.9 | 98 | 73.1 | 72.7 | 73 |
| | 2.5 µM | 105.2 | 104.8 | 105 | 91.1 | 91 | 91 |
| A1/3-scr3 | 15 µM | 122.5 | 122 | 122 | 106.1 | 105.5 | 106 |
| | 12.5 µM | 116 | 117.6 | 117 | 103.1 | 104.5 | 104 |
| | 7.5 µM | 114.2 | 113.9 | 114 | 100.8 | 100.6 | 101 |
| | 2.5 µM | 107.8 | 107.4 | 108 | 96.3 | 95.2 | 96 |
| Exp. 2 | | | | | | | |
| IZ | 0 | 111 | 109.7 | 110 | 94.7 | 95.5 | 95 |
| A1/3 | 12.5 µM | 83.6 | 85.5 | 85 | 56.7 | 56.7 | 57 |
| | 10 µM | 79.1 | 78.5 | 79 | 63.1 | 62.5 | 63 |
| | 7.5 µM | 100.1 | 100.5 | 100 | 71.6 | 73.9 | 73 |
| | 5 µM | 103.4 | 104.8 | 104 | 77 | 76 | 77 |
| | 2.5 µM | 110.1 | 108.9 | 110 | 88 | 88.8 | 88 |
| | 1.25 µM | 108.7 | 109.3 | 109 | 90.7 | 90.8 | 91 |

Table 3A. Clotting activity of peptides A1/3 and A1/3-scr (scrambled version of A1/3) in FVIII deficient plasma either in the presence or in the absence (w/o) of 2.2 nM human FIXa. Shown are two independent representative experiments (Exp. 1 and Exp. 2). All clotting experiments have been done in duplicate. Given are the clotting times for the individual experiments and the average clotting time in seconds (sec). Experiments shown in table 3A have been done employing the aPTT reagent DAPTTIN (Baxter Hyland Immuno). Compared to the buffer control (IZ, imidazole buffer) the peptide A1/3 gave rise to a dose dependent reduction in the clotting time. The reduction in the clotting time became much more pronounced by the addition of 2.2 nM activated human FIX to the reaction mix. The scrambled version of peptide A1/3, A1/3-scr3 did not show any reduction of the clotting time. In fact, at concentrations above 2.5 µM, the scrambled peptide became inhibitory and therefore prolonged the clotting time. Peptides A1/1, A1/2, A1/4 and A1/5 did not give any reduction in the clotting time indicating that they lack procoagulant activity (data not shown).

| | Final conc. | w/o FIXa sec | w/o FIXa sec | average sec | 2.2 nM FIXa sec | 2.2 nM FIXa sec | average sec |
|---|---|---|---|---|---|---|---|
| IZ | 0 | 131.8 | 132.1 | 132 | 107.9 | 108.7 | 108 |
| FVIII | 12.5 mU/ml | 68.9 | 69 | 69 | 52.9 | 53.6 | 53 |
| | 6.25 mU/ml | 77.8 | 77.9 | 78 | 58.6 | 58.9 | 59 |
| A1/3 | 15 µM | 152.8 | 149.3 | 151 | 75.4 | 75.2 | 75 |
| | 10 µM | 135.7 | 134.6 | 135 | 76.2 | 79.8 | 78 |
| | 5 µM | 152.6 | 155.6 | 154 | 86.6 | 90.2 | 88 |
| | 1 µM | 138.3 | 138.8 | 139 | 103.7 | 105.9 | 105 |

Table 3B. Clotting activity of peptide A1/3 in FVIII deficient plasma when Pathromtin SL (DADE Behring) is used as an aPTT reagent. The experiments were done in duplicate, either in the presence or in the absence (w/o) of 2.2 nM human FIXa. Given are the clotting times for the individual experiments and the average clotting time in seconds (sec). Factor VIII and imidazole buffer (IZ) were included as positive and negative control respectively.

In contrast to the experiments shown in table 3A the experiments shown in table 3B have been done employing the aPTT reagent Pathromtin SL. In the presence of FIXa, the peptide A1/3 gave rise to a dose dependent reduction in the clotting time whereas in the absence of FIXa no reduction of the clotting time was detectable.

In another series of experiments we set out to improve the plasma stability (protection from, e.g., proteolytic degradation) of peptide A1/3. One approach was to substitute the N- and C-terminal L-Arg residues with D-Arg residues (exemplified by peptides A1/3-rd and A1/3-Rd-srmb). Peptides A1/3-rd and A1/3-Rd-srmb (scrambled version of the peptide) were then analyzed in a chromogenic as well as in the aPTT based clotting assay. These experiments revealed that exchanging the terminal L-Arg residues for D-Arg residues did not change the FVIII-like activity as measured in the chromogenic assay, indicating that chirality of the Arg-residues does not play a major role in chromogenic activity (FIG. 20). In addition, the aPTT based one-stage clotting activity, although somewhat reduced, was still easily detectable (Table 4).

| | Peptide conc. | w/o FIXa sec | w/o FIXa, sec | average sec | 2.2 nM FIXa sec | 2.2 nM FIXa sec | average sec |
|---|---|---|---|---|---|---|---|
| IZ | 0 | 110 | 109.1 | 110 | 96 | 96 | 96 |
| A1/3 | 15 µM | 77.8 | 78 | 78 | 56.1 | 55.5 | 56 |
| | 12.5 µM | 99.4 | 100.5 | 100 | 65 | 68 | 67 |
| | 10 µM | 104.4 | 104.5 | 104 | 72 | 73.2 | 73 |
| | 7.5 µM | 105.2 | 105.2 | 105 | 80.7 | 80.5 | 81 |
| | 5 µM | 108.4 | 107.7 | 108 | 89.7 | 88.3 | 89 |
| | 2.5 µM | 107.9 | 107.6 | 108 | 93.6 | 93.3 | 93 |
| | 1.25 µM | 106.7 | 107 | 107 | 94.4 | 95 | 95 |
| A1/3-Rd | 15 µM | 96.4 | 95.4 | 96 | 76.1 | 74.4 | 75 |
| | 12.5 µM | 98 | 98.6 | 98 | 72.3 | 73.7 | 73 |
| | 10 µM | 93.5 | 95.8 | 95 | 74.2 | 77.2 | 76 |
| | 7.5 µM | 97.6 | 98.1 | 98 | 80.9 | 82.2 | 82 |
| | 5 µM | 99.2 | 99.1 | 99 | 86 | 85.1 | 86 |
| | 2.5 µM | 102.7 | 103.4 | 103 | 94.4 | 94.7 | 95 |
| | 1.25 µM | 107.5 | 107.7 | 108 | 96.6 | 96 | 96 |
| A1/3-Rd srmb | 15 µM | 121.9 | 121.3 | 122 | 112.7 | 112.4 | 113 |
| | 12.5 µM | 117.2 | 118 | 118 | 108.1 | 107.8 | 108 |
| | 10 µM | 115.8 | 115.3 | 116 | 107.2 | 107.8 | 108 |
| | 7.5 µM | 114.6 | 113.6 | 114 | 107.6 | 106.6 | 107 |
| | 5 µM | 113.1 | 112.4 | 113 | 108.5 | 108.2 | 108 |

-continued

| Peptide conc. | w/o FIXa sec | w/o FIXa, average sec | 2.2 nM FIXa sec | 2.2 nM FIXa sec | average sec |
|---|---|---|---|---|---|
| 2.5 μM | 111.9 | 111.9 | 112 | 105 | 104.2 | 105 |
| 1.25 μM | 107.2 | 107.1 | 107 | 101.1 | 105.3 | 103 |

Table 4. One stage clotting activity of peptides A1/3, A1/3-Rd and A1/3-Rd-srmb (sequences see table 2). IZ, buffer control.

FIG. 20 demonstrates the unchanged chromogenic activity of peptide A1/3-Rd. Peptides at a final concentration of 12 μM or the buffer control (IZ) were incubated in the presence of 2.3 nM human FIXa (+). The chromogenic activity of peptide A1/3 and A1/3-Rd was found to be virtually unchanged and gave almost identical results in the chromogenic assay. The scrambled version of peptide A1/3, A1/5 as well as the buffer gave no significant FXa generation.

In the next series of experiments we set out to determine the individual role of any amino acid of the peptide core sequence by substituting each residue for the amino acid Alanine (Table 5).

100 mM NaCl, 1% human albumin, pH7.4) to the desired final concentration. The peptides were analyzed for their chromogenic activity as well as for their potential to reduce the clotting time in a FVIII deficient plasma. The one-stage clotting assay was essentially done as described (see example 6). Clotting times (time from starting the reaction to the "clot"-formation were compared either against a buffer control or a control peptide (scrambled version).

Some of the results of the "Alanine scan" are given for the peptides A1/3-2 and A1/3-3. The change of $G_3$-$A_3$ as exemplified in the peptide A1/3-2 yields high chromogenic activity and a strong reduction of the one-stage clotting time (34 seconds at a concentration of 12.5 μM) in the presence of 2.2 nM human FIXa. Peptide A1/3-3 ($G_4$-$A_4$) exhibits an optimum of chromogenic activity around a final concentration of 12 μM with decreased activity at either higher or lower concentrations. The peptide is somewhat inhibitory in a one-stage clotting assay at higher concentrations (12.5 μM) in the absence of FIXa but becomes strongly active in the presence of 2.2 nM FIXa (31 seconds, 12.5 μM).

In the next series of experiments we set out to determine the individual role of any amino acid of the peptide core sequence by substituting each core residue for the amino acid glutamic acid (E) (see Table 6).

| Peptide | Sequence | Amino acid # | MW (D) | pI | Remark |
|---|---|---|---|---|---|
| A1/3 | RRREGGGYYVNWYFDRRR (SEQ ID NO:12) | (18aa) | 2407 | 9.9 | Basic pI, soluble. |
| A1/3-13 | RRRAGGGYYVNWYFDRRR (SEQ ID NO:19) | (18aa) | 2349 | 10.4 | $E_1$-$A_1$ |
| A1/3-1 | RRREAGGYYVNWYFDRRR (SEQ ID NO:20) | (18aa) | 2421 | 9.9 | $G_2$-$A_2$ |
| A1/3-2 | RRREGAGYYVNWYFDRRR (SEQ ID NO:21) | (18aa) | 2421 | 9.9 | $G_3$-$A_3$ |
| A1/3-3 | RRREGGAYYVNWYFDRRR (SEQ ID NO:22) | (18aa) | 2421 | 9.9 | $G_4$-$A_4$ |
| A1/3-4 | RRREGGGAYVNWYFDRRR (SEQ ID NO:23) | (18aa) | 2315 | 9.9 | $Y_5$-$A_5$ |
| A1/3-5 | RRREGGGYAVNWYFDRRR (SEQ ID NO:24) | (18aa) | 2315 | 9.9 | $Y_6$-$A_6$ |
| A1/3-6 | RRREGGGYYANWYFDRRR (SEQ ID NO:25) | (18aa) | 2379 | 9.9 | $V_7$-$A_7$ |
| A1/3-7 | RRREGGGYYVAWYFDRRR (SEQ ID NO:26) | (18aa) | 2364 | 9.9 | $N_8$-$A_8$ |
| A1/3-8 | RRREGGGYYVNAYFDRRR (SEQ ID NO:27) | (18aa) | 2292 | 9.9 | $W_8$-$A_9$ |
| A1/3-9 | RRREGGGYYVNWAFDRRR (SEQ ID ND:28) | (18aa) | 2315 | 9.9 | $Y_{10}$-$A_{10}$ |
| A1/3-10 | RRREGGGYYVNWYADRRR (SEQ ID NO:29) | (18aa) | 2331 | 9.9 | $F_{11}$-$A_{11}$ |
| A1/3-11 | RRREGGGYYVNWYFARRR (SEQ ID NO:30) | (18aa) | 2363 | 10.5 | $D_{12}$-$A_{12}$ |
| A1/3-12srmb | RRRYVYNGWGYFEGARRR (SEQ ID NO:31) | (18aa) | 2363 | 10.4 | Scrambled version |

Table 5. Listed are the peptides designed to elucidate the role of any single amino acid within the peptide core sequence ($E_1G_2G_3G_4Y_5Y_6V_7N_8W_9Y_{10}F_{11}D_{12}$; SEQ ID NO:112). The subscripted numbers describe the position of the amino acid within the peptide. Alanine, an uncharged small amino acid, was substituted for each amino acid ("Alanine scan"). Also listed are the lengths of the peptides (amino acids #), the calculated molecular weights (MW, in Dalton (D) and the statistical isoelectric points (pI).

Each of the peptides was dissolved individually in imidazole buffer (50 mM imidazole, 100 mM NaCl, pH7.2) and subsequently diluted in clotting buffer (50 mM imidazole,

| Peptide | Sequence | Amino-Acids | MW (D) | pI | Remark |
|---|---|---|---|---|---|
| A1/3 | RRREGGGYYVNWYFDRRR (SEQ ID NO:12) | (18aa) | 2407 | 9.9 | Basic pI, soluble, |
| A1/3-22 | RRREEGGYYVNWYFDRRR (SEQ ID NO:32) | (18aa) | 2479 | 9.5 | $G_2$-$E_2$ |
| A1/3-23 | RRREGEGYYVNWYFDRRR | (18aa) | 2479 | 9.5 | $G_3$-$E_3$ |

-continued

| Peptide | Sequence | Amino-Acids | MW (D) | pI | Remark |
|---|---|---|---|---|---|
| | (SEQ ID NO:33) | | | | |
| A1/3-24 | RRREGGEYYVNWYFDRRR (SEQ ID NO:34) | (18aa) | 2479 | 9.5 | $G_4$–$E_4$ |
| A1/3-26 | RRREGGGEYVNWYFDRRR (SEQ ID NO:35) | (18aa) | 2373 | 9.4 | $Y_5$–$E_5$ |
| A1/3-27 | RRREGGGYEVNWYFDRRR (SEQ ID NO:36) | (18aa) | 2373 | 9.4 | $Y_6$–$E_6$ |
| A1/3-28 | RRREGGGYYENWYFDRRR (SEQ ID NO:37) | (18aa) | 2437 | 9.5 | $V_7$–$E_7$ |
| A1/3-29 | RRREGGGYYVEWYFDRRR (SEQ ID NO:38) | (18aa) | 2422 | 9.5 | $N_8$–$E_8$ |
| A1/3-30 | RRREGGGYYVNEYFDRRR (SEQ ID NO:39) | (18aa) | 2350 | 9.5 | $W_9$–$E_9$ |
| A1/3-31 | RRREGGGYYVNWEFDRRR (SEQ ID NO:40) | (18aa) | 2373 | 9.4 | $Y_{10}$–$E_{10}$ |
| A1/3-32 | RRREGGGYYVNWYEDRRR (SEQ ID NO:41) | (18aa) | 2389 | 9.5 | $F_{11}$–$E_{11}$ |
| A1/3-33 | RRREGGGYYVNWYFERRR (SEQ ID NO:42) | (18aa) | 2421 | 9.9 | $D_{12}$–$E_{12}$ |
| A1/3-34srmb | RRRGEYGEYWNGDFYRRR (SEQ ID NO:43) | (18aa) | 2437 | 9.5 | Scrambled version |

Table 6. Listed are the peptides designed to elucidate the role of any single amino acid within the peptide core sequence ($E_1G_2G_3G_4Y_5Y_6V_7N_8W_9Y_{10}F_{11}D_{12}$; SEQ ID NO:112). The subscripted numbers describe the position of the amino acid within the peptide. Glutamic acid, a negatively charged large amino acid, was substituted for each amino acid of the core sequence ("Glutamic acid scan"). Also listed are the lengths of the peptide (amino acids #), the calculated molecular weights (MW, in Dalton (D) and the statistical isoelectric points (pI).

Each of the peptides was solved individually in imodazole buffer (50 mM imidazole, 100 mM NaCl, pH7.2) and subsequently diluted in clotting buffer (50 mM imidazole, 100 mM NaCl, 1% human albumin, pH7.4) to the desired final concentration. The peptides derived from the "Glutamic acid scan" series were analyzed for their chromogenic FVIII-like activity as well as for their potential to reduce the clotting time in a FVIII deficient plasma. The one-stage clotting assay was essentially done as described (see example 6).

The peptide A1/3-24 showed some interesting properties. The molecule exhibited high chromogenic FVIII-like activity at concentrations between 6.5 µM-12 µM but lost activity at higher concentrations (up to 24 µM). The peptide had no procoagulant activity in the absence of human FIXa but was strongly active in the presence of 2.2 nM hFIXa.

In a second series of experiments we set out to improve the procoagulant activity of the antibody-198/B1 CDR3H derived peptide sequence B1. In a first step we improved the solubility of the original peptide sequence (B1; EGGG-FTVNWYFDV; SEQ ID NO:7) by removing the C-terminal Val residue and adding several charged residues at the N- as well as the —C-terminal end of the peptide. The resulting peptides B1/4, B1/6 (acidic pI), B1/7 (basic pI) and their scrambled versions B1/5, B1/7scr3 are readily soluble in a variety of buffer systems at physiological pH.

| Peptide | Sequence | Amino-acids | MW (D) | pI | Remark |
|---|---|---|---|---|---|
| B1 | EGGGFTVNWYFDV (SEQ ID NO:7) | (13aa) | 1491 | 6.0 | Decreased solubility |
| B1/4 | REGGGFTVNWYFDR (SEQ ID NO:45) | (14aa) | 1704 | 7.9 | Soluble, |
| B1/5 | FGVGYRGETRNFDW (SEQ ID NO:46) | (14aa) | 1704 | 8.0 | Scrambled version, soluble |
| B1/6 | EEEEGGGFTVNWYFDEEE (SEQ ID NO:47) | (18aa) | 2166 | 5.0 | Acidic pI soluble |
| B1/7 | RRREGGGFTVNWYFDRRR (SEQ ID NO:48) | (18aa) | 2329 | 9.9 | Basic pI soluble |
| B1/7 scr3 | RRRFGVGYGETNFDWRRR (SEQ ID NO:49) | (18aa) | 2329 | 9.9 | Basic pI, soluble, scrambled version |

Table 7 is a list of a series of antibody 198/B1 derived peptides. Listed are the length of the peptide (aa, amino acids #), the calculated molecular weight (MW, in Dalton (D) and the statistical isoelectric point (pI).

Peptides B1/4 and B1/5 were soluble in 50 mM Tris, 100 mM NaCl, pH=6.5. Both peptides were analyzed in a chromogenic FVIII assay. Peptide B1/4 but not the scrambled version B1/5 was found to have some chromogenic activity (data not shown).

Subsequently peptides B1/6, B1/7 and B1/7scr3 were analyzed. Each of the peptides was solved individually in 50 mM imidazole, 100 mM NaCl, pH7.2 and subsequently diluted either in clotting buffer (50 mM imidazole, 100 mM NaCl, 1% human albumin, pH7.4) or in imidazole buffer to the desired final concentration. The peptides were analyzed for their chromogenic activity as well as for their potential to reduce the clotting time in a FVIII deficient plasma (table 8 & 9). The one stage clotting assay was essentially done as described (see example 6). Clotting times (time from starting the reaction to the "clot"-formation were compared either against a buffer control or a control peptide (scrambled version).

The FIXa activating activity (FVIII cofactor-like activity) from peptide B1/7 was first measured in the chromogenic assay described above.

As shown in FIG. 21, the addition of 2.4 µM peptide B1/7 to the reaction mixture led to a well measurable generation of FXa. In contrast, the addition of 35 µM Pefabloc Xa, a specific inhibitor of FXa protease activity, resulted in a significant reduction of the chromogenic substrate cleavage reaction (FIG. 22) thereby proving that there was indeed a peptide-FIXa mediated FXa generation. If there was no addition of FIXa and FX to the reaction mixture, no FXa was synthesized (FIG. 22). Peptide B1/6 and the control peptides B1/5 and B1/7scr3 exhibited no activity (data not shown).

FIG. 21 demonstrates the chromogenic activity of peptide B1/7. The peptide at a final concentration of 2.4 µM or the buffer control (IZ) were incubated in the presence of 2.3 nM human FIXa.

In FIG. 22 peptide B1/7 at a final concentration of 2.4 µM or the buffer control (IZ) were incubated in the presence of 2.3 nM human FIXa (as indicated either as "+2.3 nM hFIXa" or "+") The chromogenic activity of peptide B1/7 was found to be dependent on the presence of FIXa and FX since no reaction is detectable when FIXa and FX are left out of the reaction (w/o FIXa/FX). To prove that the peptide B1/7 mediates indeed FXa generation, the FXa specific protease inhibitor Pefabloc Xa was added to the reaction mix (35 µM Pefabloc Xa). In a second set of experiments, the procoagulant effect of peptides B1/6, B1/7 and B1/7scr3 were tested in a aPTT based one-step coagulation assay. The experiments were done essentially as described in Example 6. The results are shown in tables 8 and 9.

| Peptide | 12.5 µM (−) | 1.25 µM (−) | 0.125 µM (−) | 12.5 nM (−) | Buffer (−) | remarks |
|---|---|---|---|---|---|---|
| B1/6 | 115 | 110 | 111 | 111 | 110 | |
| B1/7 | 157 | 112 | 109 | 110 | 110 | |
| B1/7 scr3 | 115 | 105 | 106 | 105 | 107 | |

Table 8: FVIII deficient plasma was incubated either with peptides B1/6, B1/7scr3 or B1/7 in the absence of activated human FIX. As a negative control, plain buffer was added to the deficient plasma. The clotting times for the various combinations are given. Under these conditions, peptide B1/7 at its highest concentration (12.5 µM) becomes inhibitory to the coagulation process as indicated by the extended clotting time of 157 seconds.

| Peptide | 12.5 µM (+) | 1.25 µM (+) | 0.125 µM (+) | 12.5 nM (+) | Buffer (+) | remarks |
|---|---|---|---|---|---|---|
| B1/6 | 103 | 100 | 101 | 100 | 100 | |
| B1/7 | 83 | 92 | 99 | 99 | 100 | |
| B1/7 scr3 | 102 | 94 | 94 | 94 | 94 | |

Table 9: FVIII deficient plasma was incubated either with peptides B1/6, B1/7scr3 or B1/7 in the presence of activated human FIX. As a negative control, plain buffer was added to the deficient plasma. The clotting times for the various combinations are given. In the presence of FIXa, peptide B1/7 becomes procoagulant as indicated by the reduced clotting time (83 seconds compared to 102 seconds for the scrambled peptide and 100 seconds for the buffer control).

Example 12

Procoagulant Activity of Peptide Derivatives Obtained from CDR3 Regions of Anti-FIX/FIXa-Antibodies in FVIII Inhibitor Plasma To assay for the procoagulant activity of peptide A1/3 in FVIII inhibitor plasma the following experiment was carried out. We performed a standard aPTT based one stage clotting assay, but instead of FVIII deficient plasma we employed FVIII inhibitor plasma. The inhibitory potency of the plasma was 8.1 Bethesda Units per ml.

TABLE 10

| Peptide conc. | w/o FIXa sec | w/o FIXa sec | Average sec | FIXa sec | FIXa sec | average sec |
|---|---|---|---|---|---|---|
| IZ | 0 | 104.9 | 103.6 | 104 | 94.2 | 94.1 | 94 |
| A1/3 | 12.5 µM | 85.8 | 85.3 | 86 | 61 | 60.2 | 61 |
| | 10 µM | 88.4 | 87.9 | 88 | 61.3 | 61.8 | 62 |
| | 7.5 µM | 93.7 | 92.7 | 93 | 68.8 | 70.9 | 70 |
| | 5 µM | 101.5 | 101.1 | 101 | 81 | 82 | 82 |
| | 2.5 µM | 106.1 | 105.3 | 106 | 90.2 | 90.5 | 90 |
| | 1.25 µM | 104.5 | 104.3 | 104 | 91.3 | 91.4 | 91 |

Table 10: Various amounts of peptide A1/3 (12.5 µM-1.25 µM) were added to FVIII inhibitor plasma (either in the presence (FIXa) of 2.2 nM FIXa or in the absence (w/o FIXa). As a negative control, plain buffer was added to the plasma (IZ). Experiments were done in duplicate and the average (aver.) was calculated. The clotting times (in seconds) for the various combinations are given. It is easily appreciable that the peptide A1/3 reduces (in a dose dependent manner) the clotting time of FVIII inhibitor plasma in the presence of FIXa but, although albeit to a much lesser extent, also in the absence of FIXa.

Example 13

Conversion of the 196/C4 IgM into IgG1

Since some IgM antibodies demonstrate high FVIII-like activity in chromogenic assays, attempts were made to convert such IgM antibodies into IgG antibodies (though antibody derivatives such as Fab, $F(ab)_2$, scFv, etc. could also be produced). Described in detail below is the rescue of the IgM variable region genes. Expression vector pBax-IgG1 (FIG. 23) was first constructed from vectors pSI (Promega) and pEF/Bsd (Invitrogen) through multiple cloning steps. B-lymphocytes of a donor are purified from blood and mature mRNA purified from these cells using the "micro-mRNA purification-kit" (Pharmacia). The cDNA of a human kappa chain and a human gamma 1 chain are prepared employing the "you-primefirst-strand-cDNA-"kit" (Pharmacia) using specific primers.

The coding sequence of a human kappa light chain constant domain is amplified from the cDNA by PCR using specific primers.

The gene of a human gamma 1 chain constant region (CH1-hinge-CH2—CH3) is amplified from the cDNA by PCR using specific primers.

The PCR product of the light chain constant domain is digested with XbaI and NheI and inserted into digested pSI. The resultant vector is cleaved with EcoRI and XbaI and annealed oligonucleotides are inserted, resulting in vector pSI-Ckappa. The annealed oligonucleotides provide for the leader and the SacI-XbaI sites for insertion of the kappa chain variable region. The PCR product of the human gamma 1 chain constant region is digested with SpeI and BamHI and inserted into digested pSI. The resultant vector is cleaved with SpeI and NotI and annealed oligonucleotides are inserted resulting in vector pSI-Cgamma. The annealed oligonucleotides provide for the leader and the XhoI-BstEI sites for insertion of the heavy chain variable region. Vector pEF/Bsd is digested NheI and SfiI, blunt ended by Klenow treatment and the whole expression cassette of pSI-Ckappa, excised with BglII and BamHI, is inserted (after Klenow treatment). The resultant vector is digested with EcoRI and HindIII and treated with Klenow. The whole expression cassette of pSI-Cgamma is excised with BglII and BamHI and is inserted (after Klenow treatment). The resultant vector is named pBax-IgG1.

The light chain variable region can be inserted in between the SacI-XbaI sites, yielding the complete coding-sequence of a kappa light chain. The heavy chain variable region can be cloned in between the XhoI-BstEI sites, resulting in a complete IgG1 heavy chain gene. Both open reading frames are expressed under the control of the SV40-promoter and harbour the coding sequence of a signal peptide at the 5' end of the genes for secretion of the heavy and light chains into the endoplasmatic reticulum. Transfection into COS cells allows the expression of an IgG1 with the same binding properties as the parental IgM.

Construction of the plasmid pBax-196/C4 is further accomplished by amplifying the VH of the 196/C4 scFv (subcloned as described in Experiment 10) by PCR using specific primers. The PCR product is digested with XhoI and BstEII and inserted into XhoI and BstEII digested pBax IgG1. The VL of the 196/C4 scFv is amplified by PCR using specific primers. The PCR product is digested with SacI and XbaI and inserted into SacI and XbaI-digested pBax IgG1-VH. The resultant vector (pBax-196/C4) is transfected into COS cells by electroporation, and hybrid IgG1 molecules (murine variable region and human constant region) with the same specificity as the parental IgM is expressed.

Example 14

Activation of FIXa Amydolytic Activity by Anti-FIXa Antibodies

Briefly, 20±1 factor IXa (containing 20 mU FIXa (Stago)) were incubated at 37° C., with 200 µl of reaction buffer (50 mM Tris HCl pH7.4, 100 mM NaCl, 5 mM $CaCl_2$ and 40% Ethyleneglycol), 25 µl of FIXa substrate ($CH_3SO_2$-D-CHG-Gly-Arg-pNA, AcOH, 10M/ml, Pentapharm LTD) in the absence or presence of various amounts of anti-FIX antibodies 198/B1 (IgG isotype) or 196/AF1 (IgM isotype). Specific cleavage of FIXa substrate was monitored at 405 nm in an ELISA reader.

The presence of the anti-FIX antibodies enhanced the amydolytic activity of FIXa at least 2 fold. FIG. 24 shows the increase of the amidolytic activity of FIXa in the presence of antibody 198/B1 (FIG. 24A) and antibody 198/AF1 (FIG. 24B).

Example 15

FVIII-like Activity Exhibited by Fab Fragments Derived from Anti FIX/FIXa-antibodies Fab fragments of anti-FIX/FIXa antibodies were prepared and purified according to standard protocols. Briefly, 1 ml antibody 198/A1(4 mg/ml in 50 mM imidazole, 100 mM NaCl, pH7.4) was incubated overnight with 87 µl fragmentation buffer (1M Na Acetate, 10 mM EDTA 67.5 mg/ml L-cysteine) and 0.25 mg papain (immobilized on agarose beads), at 37° C. The preparation was filtered to remove the papain. L-histidine was added (final concentration 50 mM) and afterwards the pH was adjusted to 7.0. Finally, solid NaCl is added to give a final concentration of 1M.

Subsequently, the 198/A1 Fab fragment was purified by binding to protein L: we used ImmunoPure Immobilized PROTEIN L Plus (Pierce) in a PHARMACIA XK 16/20 Column (gel-volume: 2 ml) Buffers for chromatography were: 1) equilibration-buffer: 50 mM L-histidine pH 7.0; 1M NaCl; 0,1% (w/v) $NaN_3$; 2) wash-buffer: 50 mM L-Histidine pH 7.0; 0.1 (w/v) $NaN_3$; 3) elution-buffer: 100 mM glycine pH 2.5; 0.1% (w/v) $NaN_3$; and 4) neutralization buffer: 2M Tris/Cl pH 8,0;

Chromatography was essentially done by following steps 1 to 7 described in table 11. In order to neutralize the low pH of the elution buffer "Fraction-tubes" were pre-loaded with 0.2 ml 2M Tris pH 8.0.

TABLE 11

| STEP | BUFFER | Flow rate | Vol. | CV | Fractions |
|---|---|---|---|---|---|
| 1. column-wash | elution-buffer | 2.0 ml/min | 10 ml | 5 | waste |
| 2. equilibration | equi-buffer | 2.0 ml/min | 10 ml | 5 | waste |

TABLE 11-continued

| STEP | BUFFER | Flow rate | Vol. | CV | Fractions |
|---|---|---|---|---|---|
| 3. sample-load | sample | 1.0 ml/min | x ml | x | flow-through |
| 4. wash 1 | equi-buffer | 1.0 ml/min | 20 ml | 10 | flow-through |
| 5. wash 2 | wash-buffer | 1.0 ml/min | 10 ml | 5 | flow-through |
| 6. elution | elution-buffer | 1.0 ml/min | 15 ml | 7.5 | 1,0 ml fractions- |
| 7. neutralization | wash-buffer | 2.0 ml/min | 10 ml | 5 | waste |

Table 11

The final 198/A1 Fab preparation was dialyzed against 50 mM imidazole, 100 mM NaCl, pH7.4 and analyzed in a chromogenic FVIII assay as described above (FIG. 25). Compared to an intact antibody, the 198/A1 Fab fragment has somewhat less activity; however, the Fab fragment still gives rise to FIX dependent FXa generation.

FIG. 25 demonstrates the chromogenic FVIII-like activity of the antibody 198/A1 Fab fragment in the presence of 2.3 nM human FIXa. As a positive control we used the intact antibody 198/A1 as well as 7.5 pM FVIII. Buffer control (IZ) instead of 198/A1 Fab fragment or FVIII was used as a negative control.

Example 16

FVIII-like Activity Exhibited by Fusion Proteins Between scFv Fragments of Anti-FIX/FIXa Antibodies and E. coli Alkaline Phosphatase The single chain Fv fragment (see example 10) of antibody 198/B1 (subclone AB2) was fused to the N-terminus of E. coli alkaline phosphatase employing the pDAP2 vector system (Kerschbaumer et al., 1996). Two identical clones were isolated and designated pDAP2-198AB2#1 and pDAP2-198AB2#100 (FIG. 26). The resulting fusion proteins were expressed in E. coli, purified by metal affinity chromatography (Kerschbaumer et al., 1997) and analysed in a standard chromogenic assay (FIG. 27).

FIG. 27 demonstrates the chromogenic FVIII-like activity of two antibody 198/B1 (subclone AB2) scFv fragment-alkaline phosphatase fusion proteins (198AB2#1 and 198AB2#100) in the presence of 2.3 nM human FIXa. As a positive control we used 7.5 pM FVIII.

Example 17

FVIII-like Activity Exhibited by a Bivalent Miniantibody

In order to obtain a bivalent miniantibody, the scFv fragment of antibody 198/B1 (subclone AB2) was fused to a amphipatic helical structure employing the pZip1 vector system (Kerschbaumer et al. (Analytical Biochemistry 249, 219–227, 1997). Briefly, the gene of the 198/B1 scFv fragment was isolated from the plasmid pDAP-198AB2#100 (example 16) by digestion with SfiI and NotI. The DNA fragment was gel purified and inserted in the SfiI/NotI digested vector pZip1. The resulting plasmid was sequenced and designated pZip-198AB2#102 (FIG. 28). In parallel, we constructed a miniantibody version from an irrelevant monoclonal antibody termed #8860. In a first step, the single chain Fv fragment of antibody #8860 was assembled in the vector pDAP2. The cloning was done essentially as described in example 10. The construct was named pDAP2-8860scFv#11 (FIG. 29). Subcloning of the scFv fragment contained within pDAP2-8860scFv#11 into plasmid pZip1 (see above) yielded the miniantibody construct p8860-Zip#1.2 (FIG. 30). Since antibody #8860 does not react with FIX/FIXa (as judged by Western Blot and ELISA analysis) it represents an appropriate negative control. Subsequently, the miniantibody proteins were expressed in *E. coli* and purified from bacterial supernatants by binding to Protein L according to the following protocol: For affinity chromatography we used ImmunoPure Immobilized PROTEIN L Plus (Pierce) in a PHARMACIA XK 16/20 Columns having a gel-volume of 4 ml Buffers employed were: 1) equilibration-buffer: 5 mM L-Histidine pH 7.0, 1M NaCl, 0.1% (w/v) NaN$_3$, wash-buffer: 50 mM L-histidine pH 7.0, 0.1% (w/v) NaN$_3$; elution-buffer: 100 mM glycine pH 2.5, 0.1% (w/v) NaN$_3$; and neutralization buffer: 2M Tris/Cl pH 8.0.

Samples were prepared as follows: The bacterial culture supernatant was obtained by centrifugation of the bacterial expression culture (11,000×g, 4° C., 10 minutes). 470 g of ammonium-sulphate was added to 1 liter of supernatant and the solution stirred on ice for 1 hour to precipitate the protein. The precipitate was pelleted at 14,000×g for 35 minutes at 2° C. and re-dissolved in 100 ml 20 mM Tris pH 7.0. Subsequently the concentrate was dialyzed against 20 mM Tris pH 7.0, L-histidine was added to a final concentration of 50 mM and the pH was adjusted to 7.0. Finally, solid NaCl was added to give a final concentrations of 1M. Before loading on the column, a sample was first centrifuged at 16,000×g for 15 min at room temperature and then filtered through a 0.45 µm sterile filter.

Chromatography was essentially done by following steps 1 to 7 described in table 12. In order to neutralize the low pH of the elution buffer "Fraction-tubes" were pre-loaded with 0.2 ml 2M Tris pH 8.0.

| STEP | BUFFER | Flow rate | Vol. | CV | Fractions |
|---|---|---|---|---|---|
| 1. column-wash | elution-buffer | 2.0 ml/min | 20 ml | 5 | waste |
| 2. equilibration | equi-buffer | 2.0 ml/min | 20 ml | 5 | waste |
| 3. sample-load | sample | 1.0 ml/min | x ml | x | flow-through |
| 4. wash 1 | equi-buffer | 1.0 ml/min | 40 ml | 10 | flow-through |
| 5. wash 2 | wash-buffer | 1.0 ml/min | 20 ml | 5 | flow-through |
| 6. elution | elution-buffer | 1.0 ml/min | 30 ml | 7.5 | 1.0 ml fractions- |
| 7. neutralization | wash-buffer | 2.0 ml/min | 20 ml | 5 | waste |

Table 12. The final 198/B1 (subclone AB2) miniantibody preparation (designated 198AB-Zip#102) and the negative control 8860-Zip#1.2 were dialyzed against 50 mM imidazole, 100 mM NaCl, pH7.4 and analyzed in a chromogenic FVIII assay as described above (FIG. 31).

As can be seen in FIG. 31, the miniantibody construct 198AB-Zip#102 gives rise to substantial FXa generation (compare to FVIII) whereas the negative control miniantibody 8860-Zip#1.2 does not.

FIG. 31 demonstrates the chromogenic FVIII-like activity of the 198/B1 (subclone AB2) miniantibody 198AB-Zip#102 in the presence of 2.3 nM human FIXa. As a positive control we used 4.8 pM FVIII whereas an unrelated miniantibody (8860-Zip#1.2) and plain reaction buffer (IZ) served as negative controls.

Example 18

FVIII-like Activity Exhibited by Anti-FIXa/FIX Antibody scFv Fragments

The single chain Fv fragment of antibody 198/B1 (subclone AB2) as well as the scfv fragment of antibody #8860 were expressed employing the pMycHis6 vector system. Vector pMycHis6 (FIGS. 32 & 33) was constructed by cleaving vector pCOCK (Engelhardt et al., 1994, Biotechniques, 17: 44–46) with NotI and EcoRI and insertion of the following oligonucleotides: mychis6-co: 5' ggc-cgcagaacaaaaactcatctcagaagaggatct gaatggggcggcacatcac-catcaccatcactaataag 3' (SEQ. ID.NO.

79) and mycchis-ic: 5'aattcttattagtgatggtgatggtgat-gtgccgccccattcagatcctct tctgagatgagtttttgttctgc 3' (SEQ.ID.NO. 80) FIG. 32 shows a schematic representation of the plasmid pMycHis6. The c-myc-tag sequence is used to detect the scFv fragment in an ELISA or a Western Blot analysis (Evan et al., Mol.Cell.Biol., 1985, 5(12), pp. 3610–6). The His6-tag sequence was included to facilitate the purification of scFv fragments by metal ion chromatography (Hochuli et al., 1988. Biotechnology, 6: 1321–1325). The plasmid contains the lacZ gene promoter (PlacZ) the PelB-leader sequence (see legend FIG. 26) an *E. coli* origin of replication (colElori) and a M13 phage origin of replication (M13ori). To allow for specific selection, the plasmid also carries the gene for the enzyme β-lactamase (AmpR) mediating resistance against the antibiotic ampicillin.

The gene of the 198/B1 (clone AB2)-scFv was rescued from plasmid pDAP2-198AB2#100 (example 16) by digestion with SfiI and NotI and inserted into SfiI/NotI cleaved pMycHis6. The resultant plasmid was designated pMycHis-198AB2#102. FIG. 34 shows the nucleotide and amino acid sequence of 198AB2 scFv (linked to the c-myc-tag and the His6tag):the resulting ORF of the expression vector is named pMycHisG-198AB2#102. Vector pMycHis6 was constructed by cleaving vector pCOCK (Engelhardt O. et al, BioTechniques 17, 44–46, 1994) NotI-EcoRI and inserting the following annealed oligonucleotides: (5'-GGCCGCAGAACAAAAACTCATCTCAGAA-GAGGATCTGAATGGG GCGGCACATCACCATCACCATCACTAATAAG-3' (SEQ.ID.No. 103) and 5'-TTATTAGTGATGGTGATGGT GATGTGCCGCCCCATTCAGATCCTCTTCTGAGATGA GTTTTTGTTCTGC-3'(SEQ.ID.NO. 104)). The resultant vector, named pMycHis6, was cleaved SfiI-NotI and the gene of scFv 198AB2 was swapped into this vector from vector pDAP2-198AB2#100.

In analogy to the 198AB2 construct, the #8860 scFv fragment was cloned from a plasmid designated pDAP2-8860scFv clone 11. The pure scFv protein of #8860 was designated 8860-M/H#4c (plasmid p8860-M/H#4c, FIG. 35). The scFv proteins were expressed in *E. coli* and affinity purified from bacterial supernatants on Protein L columns (see example 17). The final MycHis-198AB2#102 and 8860-M/H#4c preparations were dialyzed against 50 mM imidazole, 100 mM NaCl, pH7.4 and analyzed in a chromogenic FVIII assay as described above (FIG. 36).

As can be seen in FIG. 36, the scfv construct MycHis-198AB2#102 gave rise to a substantial FXa generation whereas the negative controls 8860-M/H#4c and plain reaction buffer (IZ) did not.

FIG. 36 demonstrates the chromogenic FVIII-like activity of the 198/B1 (subclone AB2) scFv fragment (MycHis-198AB2#102) in the presence of 2.3 nM human FIXa. As a positive control we used 4.8 pM FVIII whereas a unrelated scfv (8860-M/H#4c) and plain reaction buffer (IZ) served as negative controls.

What is claimed is:

1. An isolated antibody or antibody fragment thereof that binds Factor IX or Factor IXa and increases the procoagulant activity of Factor IXa.

2. The antibody or antibody fragment according to claim 1 that increases the procoagulant activity of Factor IXa in the presence of Factor VIII inhibitors.

3. The antibody or antibody fragment according to claim 1 wherein the antibody is an IgG, IgM, IgA or IgE antibody.

4. The antibody or antibody fragment according to claim 1, wherein said antibody or antibody fragment is selected from the group consisting of a monoclonal antibody, a chimeric antibody, a humanized antibody, a single chain antibody, a bispecific antibody, a diabody, and di-, oligo- or multimers thereof.

5. A CDR3 peptide of the antibody or antibody fragment according to claim 1 consisting of an amino acid sequence selected from the group consisting of:

Tyr-Gly-Asn-Ser-Pro-Lys-Gly-Phe-Ala-Tyr (SEQ ID NO:5); and

Asp-Gly-Gly-His-Gly-Tyr-Gly-Ser-Ser-Phe-Asp-Tyr (SEQ ID NO:6).

6. The antibody or antibody fragment according to claim 1, wherein the variable region of said antibody or antibody fragment comprises amino acids 1–119 and amino acids 135–242 as listed in SEQ ID NO:82.

7. The antibody or antibody fragment according to claim 6 that additionally comprises an artificial linker sequence.

8. The antibody or antibody fragment according to claim 1, wherein the variable region of said antibody or antibody fragment comprises amino acids 1–121 and amino acids 137–249 as listed in SEQ ID NO:84.

9. The antibody or antibody fragment according to claim 8 that additionally comprises an artificial linker sequence.

10. The antibody or antibody fragment according to claim 1, wherein the variable region of said antibody or antibody fragment comprises amino acids 1–122 and amino acids 138–249 as listed in SEQ ID NO:86.

11. The antibody or antibody fragment according to claim 10 that additionally comprises an artificial linker sequence.

12. A hybridoma cell line secreting an antibody that binds Factor LX or Factor IXa and increases the procoagulant activity of Factor IXa.

13. The hybridoma cell line according to claim 12 that is selected from the group consisting of cell lines having ECACC deposit numbers 99090924, 99090925, 99090926, 99121614, 99121615, 99121616, 99121617, 99121618, 99121619 and 99121620.

14. An antibody that is secreted by a hybridoma cell line according to claim 12.

15. A preparation comprising an antibody or antibody fragment according to claim 1 and a pharmaceutically acceptable carrier.

16. The preparation according to claim 15, additionally comprising Factor IXaα and/or Factor IXaβ.

17. A method of obtaining an antibody that interacts with Factor IX or Factor IXa and increases the procoagulant activity of Factor IXa, comprising the steps of:
  immunizing an immunocompetent mouse with an antigen selected from the group consisting of FIX, FIXaα, FIXaβ or fragments thereof,
  isolating spleen cells of the immunized mouse,
  producing hybridoma cells,
  screening the hybridoma cell supernatants for an increase in the procoagulant activity of Factor IXa, isolating and purifying the antibody from a supernatant from the hybridoma cells which exhibit an increase in the procoagulant activity of Factor IXa.

18. The antibody or antibody fragment according to claim 4, wherein the antibody fragment is a single chain antibody.

19. The antibody or antibody fragment according to claim 4, wherein the antibody is a humanized antibody.

20. The antibody or antibody fragment according to claim 2 wherein the antibody is selected from the group consisting of an IgG, IgM, IgA or IgE antibody.

21. The antibody or antibody fragment of claim 1, wherein the antibody fragment comprises a CDR3 peptide.

22. The antibody or antibody fragment of claim 1, wherein the antibody fragment is a CDR3 peptide.

* * * * *

SEQUENCE LISTING

<160> NUMBER OF SEQ ID NOS: 112

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:primer
      oligonucleotide MOCG1-2FOR

<400> SEQUENCE: 1
ctcaattttc ttgtccacct tggtgc                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:primer
      oligonucleotide MOCG3FOR

<400> SEQUENCE: 2
ctcgattctc ttgatcaact cagtct                                          26

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:primer
      oligonucleotide MOCMFOR

<400> SEQUENCE: 3
tggaatgggc acatgcagat ctct                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:primer
      MOCKFOR

<400> SEQUENCE: 4
ctcattcctg ttgaagctct tgac                                            24

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:hybridoma
      cell line 193/AD3 heavy chain CDR3 region

<400> SEQUENCE: 5

Tyr Gly Asn Ser Pro Lys Gly Phe Ala Tyr
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:hybridoma
      cell line 193/K2 heavy chain CDR3 region

```
<400> SEQUENCE: 6

Asp Gly Gly His Gly Tyr Gly Ser Ser Phe Asp Tyr
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:hybridoma
      cell line 193/AB2 (derived from antibody 198/B1) heavy chain CDR3
      region, peptide B1

<400> SEQUENCE: 7

Glu Gly Gly Gly Phe Thr Val Asn Trp Tyr Phe Asp Val
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence:hybridoma
      cell line 198/A1 heavy chain CDR3 region, peptide A1

<400> SEQUENCE: 8

Glu Gly Gly Gly Tyr Tyr Val Asn Trp Tyr Phe Asp Val
 1               5                  10

<210> SEQ ID NO 9

<400> SEQUENCE: 9

000

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:antibody
      198/A1 derived mutated peptide A1/1 scrambled versioon of A1

<400> SEQUENCE: 10

Val Tyr Gly Phe Gly Trp Gly Tyr Glu Val Asn Asp Tyr
 1               5                  10

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutated peptide A1/2

<400> SEQUENCE: 11

Glu Glu Glu Glu Gly Gly Gly Tyr Tyr Val Asn Trp Tyr Phe Asp Glu
 1               5                  10                  15

Glu Glu

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutated peptide A1/3
```

-continued

```
<400> SEQUENCE: 12

Arg Arg Arg Glu Gly Gly Gly Tyr Tyr Val Asn Trp Tyr Phe Asp Arg
 1               5                  10                  15

Arg Arg

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutated peptide A1/4 scrambled version of A1/2

<400> SEQUENCE: 13

Glu Tyr Gly Glu Gly Tyr Gly Glu Val Asn Glu Tyr Asp Glu Phe Glu
 1               5                  10                  15

Trp Glu

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutated peptide A1/5 scrambled version of A1/3

<400> SEQUENCE: 14

Val Arg Tyr Arg Asn Arg Tyr Arg Trp Gly Tyr Arg Gly Arg Phe Gly
 1               5                  10                  15

Asp Glu

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutated peptide A1/3-scr3 scrambled version of A1/3

<400> SEQUENCE: 15

Arg Arg Arg Gly Glu Tyr Gly Val Tyr Trp Asn Gly Asp Phe Tyr Arg
 1               5                  10                  15

Arg Arg

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19
```

```
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-13 Alanine scan E-1-A-1

<400> SEQUENCE: 19

Arg Arg Arg Ala Gly Gly Gly Tyr Tyr Val Asn Trp Tyr Phe Asp Arg
 1               5                  10                  15

Arg Arg

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-1 Alanine scan G-2-A-2

<400> SEQUENCE: 20

Arg Arg Arg Glu Ala Gly Gly Tyr Tyr Val Asn Trp Tyr Phe Asp Arg
 1               5                  10                  15

Arg Arg

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-2 Alanine scan G-3-A-3

<400> SEQUENCE: 21

Arg Arg Arg Glu Gly Ala Gly Tyr Tyr Val Asn Trp Tyr Phe Asp Arg
 1               5                  10                  15

Arg Arg

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-3 Alanine scan G-4-A-4

<400> SEQUENCE: 22

Arg Arg Arg Glu Gly Gly Ala Tyr Tyr Val Asn Trp Tyr Phe Asp Arg
 1               5                  10                  15

Arg Arg

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-4 Alanine scan Y-5-A-5

<400> SEQUENCE: 23

Arg Arg Arg Glu Gly Gly Gly Ala Tyr Val Asn Trp Tyr Phe Asp Arg
 1               5                  10                  15

Arg Arg
```

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-5 Alanine scan Y-6-A-6

<400> SEQUENCE: 24

Arg Arg Arg Glu Gly Gly Gly Tyr Ala Val Asn Trp Tyr Phe Asp Arg
 1               5                  10                  15

Arg Arg

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-6 Alanine scan V-7-A-7

<400> SEQUENCE: 25

Arg Arg Arg Glu Gly Gly Gly Tyr Tyr Ala Asn Trp Tyr Phe Asp Arg
 1               5                  10                  15

Arg Arg

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-7 Alanine scan N-8-A-8

<400> SEQUENCE: 26

Arg Arg Arg Glu Gly Gly Gly Tyr Tyr Val Ala Trp Tyr Phe Asp Arg
 1               5                  10                  15

Arg Arg

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-8 Alanine scan W-9-A-9

<400> SEQUENCE: 27

Arg Arg Arg Glu Gly Gly Gly Tyr Tyr Val Asn Ala Tyr Phe Asp Arg
 1               5                  10                  15

Arg Arg

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-9 Alanine scan Y-10-A-10

<400> SEQUENCE: 28

Arg Arg Arg Glu Gly Gly Gly Tyr Tyr Val Asn Trp Ala Phe Asp Arg
 1               5                  10                  15

Arg Arg

```
<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-10 Alanine scan F-11-A-11

<400> SEQUENCE: 29

Arg Arg Arg Glu Gly Gly Gly Tyr Tyr Val Asn Trp Tyr Ala Asp Arg
 1               5                  10                  15

Arg Arg

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-11 Alanine scan D-12-A-12

<400> SEQUENCE: 30

Arg Arg Arg Glu Gly Gly Gly Tyr Tyr Val Asn Trp Tyr Phe Ala Arg
 1               5                  10                  15

Arg Arg

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-12srmb scrambled version

<400> SEQUENCE: 31

Arg Arg Arg Tyr Val Tyr Asn Gly Trp Gly Tyr Phe Glu Gly Ala Arg
 1               5                  10                  15

Arg Arg

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-22 Glutamic acid scan G-2-E-2

<400> SEQUENCE: 32

Arg Arg Arg Glu Glu Gly Gly Tyr Tyr Val Asn Trp Tyr Phe Asp Arg
 1               5                  10                  15

Arg Arg

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-23 Glutamic acid scan G-3-E-3

<400> SEQUENCE: 33

Arg Arg Arg Glu Gly Glu Gly Tyr Tyr Val Asn Trp Tyr Phe Asp Arg
 1               5                  10                  15

Arg Arg
```

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence:antibody
198/A1 derived mutant peptide A1/3-24 Glutamic acid scan G-4-E-4

<400> SEQUENCE: 34

Arg Arg Arg Glu Gly Gly Glu Tyr Tyr Val Asn Trp Tyr Phe Asp Arg
1               5                   10                  15

Arg Arg

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence:antibody
198/A1 derived mutant peptide A1/3-26 Glutamic acid scan Y-5-E-5

<400> SEQUENCE: 35

Arg Arg Arg Glu Gly Gly Gly Glu Tyr Val Asn Trp Tyr Phe Asp Arg
1               5                   10                  15

Arg Arg

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence:antibody
198/A1 derived mutant peptide A1/3-27 Glutamic acid scan Y-6-E-6

<400> SEQUENCE: 36

Arg Arg Arg Glu Gly Gly Gly Tyr Glu Val Asn Trp Tyr Phe Asp Arg
1               5                   10                  15

Arg Arg

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence:antibody
198/A1 derived mutant peptide A1/3-28 Glutamic acid scan V-7-E-7

<400> SEQUENCE: 37

Arg Arg Arg Glu Gly Gly Gly Tyr Tyr Glu Asn Trp Tyr Phe Asp Arg
1               5                   10                  15

Arg Arg

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence:antibody 198/A1 derived mutant peptide A1/3-29 Glutamic acid scan N-8-E-8

<400> SEQUENCE: 38

```
Arg Arg Arg Glu Gly Gly Gly Tyr Tyr Val Glu Trp Tyr Phe Asp Arg
  1               5                  10                  15
```

Arg Arg

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-30 Glutamic acid scan W-9-E-9

<400> SEQUENCE: 39

Arg Arg Arg Glu Gly Gly Gly Tyr Tyr Val Glu Trp Tyr Phe Asp Arg
 1               5                  10                  15

Arg Arg

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-31 Glutamic acid scan Y-10-E-10

<400> SEQUENCE: 40

Arg Arg Arg Glu Gly Gly Gly Tyr Tyr Val Asn Trp Glu Phe Asp Arg
 1               5                  10                  15

Arg Arg

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-32 Glutamic acid scan F-11-E-11

<400> SEQUENCE: 41

Arg Arg Arg Glu Gly Gly Gly Tyr Tyr Val Asn Trp Tyr Glu Asp Arg
 1               5                  10                  15

Arg Arg

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-33 Glutamic acid scan D12-E-12

<400> SEQUENCE: 42

Arg Arg Arg Glu Gly Gly Gly Tyr Tyr Val Asn Trp Tyr Phe Glu Arg
 1               5                  10                  15

Arg Arg

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence:antibody
      198/A1 derived mutant peptide A1/3-34srmb scrambled version

<400> SEQUENCE: 43

Arg Arg Arg Gly Glu Tyr Gly Glu Tyr Trp Asn Gly Asp Phe Tyr Arg
 1               5                  10                  15

Arg Arg

<210> SEQ ID NO 44

<400> SEQUENCE: 44

000

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence:antibody
      198/B1 derived mutated peptide B1/4

<400> SEQUENCE: 45

Arg Glu Gly Gly Gly Phe Thr Val Asn Trp Tyr Phe Asp Arg
 1               5                  10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence:antibody
      198/B1 derived mutated peptide B1/5 scrambled version

<400> SEQUENCE: 46

Phe Gly Val Gly Tyr Arg Gly Glu Thr Arg Asn Phe Asp Trp
 1               5                  10

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence:antibody
      198/B1 derived mutated peptide B1/6

<400> SEQUENCE: 47

Glu Glu Glu Glu Gly Gly Gly Phe Thr Val Asn Trp Tyr Phe Asp Glu
 1               5                  10                  15

Glu Glu

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence:antibody
      198/B1 derived mutated peptide B1/7

<400> SEQUENCE: 48

Arg Arg Arg Glu Gly Gly Gly Phe Thr Val Asn Trp Tyr Phe Asp Arg
 1               5                  10                  15

Arg Arg

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence:antibody
      198/B1 derived mutated peptide B1/7scr3 scrambled version -continued

```
<400> SEQUENCE: 49

Arg Arg Arg Phe Gly Val Gly Tyr Gly Glu Thr Asn Phe Asp Trp Arg
  1               5                  10                  15

Arg Arg

<210> SEQ ID NO 50
<211> LENGTH: 57
<212> TYPE: DNA
<213> ORGANISM: Artificial Sequence
<220> FEATURE:
<223> OTHER INFORMATION: Description of Artificial Sequence:mouse V-H
      back primer VH1BACK-SfiI

<400> SEQUENCE: 50
catgccatga ctcgcggccc agccggccat ggccsaggts marctgcags agtcwgg        57

<210> SEQ ID NO 51
<211> LENGTH: 56
<212> TYPE: DNA
<213> ORGANISM: Artificial Sequence
<220> FEATURE:
<223> OTHER INFORMATION: Description of Artificial Sequence:mouse V-H
      back primer VH1BACKSfi

<400> SEQUENCE: 51
gtcctcgcaa ctgcggccca gccggccatg gccgaggtgc agcttcagga gtcagg         56

<210> SEQ ID NO 52
<211> LENGTH: 56
<212> TYPE: DNA
<213> ORGANISM: Artificial Sequence
<220> FEATURE:
<223> OTHER INFORMATION: Description of Artificial Sequence:mouse V-H
      back primer VH2BACKSfi

<400> SEQUENCE: 52
gtcctcgcaa ctgcggccca gccggccatg gccgatgtgc agcttcagga gtcrgg         56

<210> SEQ ID NO 53
<211> LENGTH: 56
<212> TYPE: DNA
<213> ORGANISM: Artificial Sequence
<220> FEATURE:
<223> OTHER INFORMATION: Description of Artificial Sequence:mouse V-H
      back primer VH3BACKSfi

<400> SEQUENCE: 53
gtcctcgcaa ctgcggccca gccggccatg gcccaggtgc agctgaagsa gtcagg         56

<210> SEQ ID NO 54
<211> LENGTH: 56
<212> TYPE: DNA
<213> ORGANISM: Artificial Sequence
<220> FEATURE:
<223> OTHER INFORMATION: Description of Artificial Sequence:mouse V-H
      back primer VH4/6BACKSfi

<400> SEQUENCE: 54
gtcctcgcaa ctgcggccca gccggccatg gccgaggtyc agctgcarca rtctgg         56

<210> SEQ ID NO 55
<211> LENGTH: 56
<212> TYPE: DNA
<213> ORGANISM: Artificial Sequence
<220> FEATURE:
<223> OTHER INFORMATION: Description of Artificial Sequence:mouse V-H
``` back primer VH5/9BACKSfi

<400> SEQUENCE: 55
gtcctcgcaa ctgcggccca gccggccatg gcccaggtyc arctgcagca gyctgg    56

<210> SEQ ID NO 56
<211> LENGTH: 56
<212> TYPE: DNA
<213> ORGANISM: Artificial Sequence
<220> FEATURE:
<223> OTHER INFORMATION: Description of Artificial Sequence:mouse V-H back primer VH7BACKSfi

<400> SEQUENCE: 56
gtcctcgcaa ctgcggccca gccggccatg gccgargtga agctggtgga rtctgg    56

<210> SEQ ID NO 57
<211> LENGTH: 56
<212> TYPE: DNA
<213> ORGANISM: Artificial Sequence
<220> FEATURE:
<223> OTHER INFORMATION: Description of Artificial Sequence:mouse V-H back primer VH8BACKSfi

<400> SEQUENCE: 57
gtcctcgcaa ctgcggccca gccggccatg gccgaggttc agcttcagca gtctgg    56

<210> SEQ ID NO 58
<211> LENGTH: 56
<212> TYPE: DNA
<213> ORGANISM: Artificial Sequence
<220> FEATURE:
<223> OTHER INFORMATION: Description of Artificial Sequence:mouse V-H back primer VH10BACKSfi

<400> SEQUENCE: 58
gtcctcgcaa ctgcggccca gccggccatg gccgaagtgc agctgktgga gwctgg    56

<210> SEQ ID NO 59
<211> LENGTH: 56
<212> TYPE: DNA
<213> ORGANISM: Artificial Sequence
<220> FEATURE:
<223> OTHER INFORMATION: Description of Artificial Sequence:mouse V-H back primer VH11BACKSfi

<400> SEQUENCE: 59
gtcctcgcaa ctgcggccca gccggccatg gcccagatcc agttgctgca gtctgg    56

<210> SEQ ID NO 60
<211> LENGTH: 68
<212> TYPE: DNA
<213> ORGANISM: Artificial Sequence
<220> FEATURE:
<223> OTHER INFORMATION: Description of Artificial Sequence:mouse J-H forward primer VH1FOR2LiAsc

<400> SEQUENCE: 60
accgccagag gcgcgcccac ctgaaccgcc tccacctgag gagacggtga ccgtggtccc    60
ttggcccc    68

<210> SEQ ID NO 61
<211> LENGTH: 60
<212> TYPE: DNA
<213> ORGANISM: Artificial Sequence
<220> FEATURE:

```
<223> OTHER INFORMATION: Description of Artificial Sequence:mouse J-H
      forward primer JH1FORLiAsc

<400> SEQUENCE: 61
accgccagag gcgcgcccac ctgaaccgcc tccacctgag gagacggtga ccgtggtccc      60

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence:mouse J-H
      forward primer JH2FORLiAsc

<400> SEQUENCE: 62
accgccagag gcgcgcccac ctgaaccgcc tccacctgag gagactgtga gagtggtgcc      60

<210> SEQ ID NO 63
<211> LENGTH: 60
<212> TYPE: DNA
<213> ORGANISM: Artificial Sequence
<220> FEATURE:
<223> OTHER INFORMATION: Description of Artificial Sequence:mouse J-H
      forward primer JH3FORLiAsc

<400> SEQUENCE: 63
accgccagag gcgcgcccac ctgaaccgcc tccacctgca gagacagtga ccagagtccc      60

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence:mouse J-H
      forward primer JH4FORLiAsc

<400> SEQUENCE: 64
accgccagag gcgcgcccac ctgaaccgcc tccacctgag gagacggtga ctgaggttcc      60

<210> SEQ ID NO 65
<211> LENGTH: 60
<212> TYPE: DNA
<213> ORGANISM: Artificial Sequence
<220> FEATURE:
<223> OTHER INFORMATION: Description of Artificial Sequence:mouse
      V-kappa back primer VK2BACK-LiAscI

<400> SEQUENCE: 65
ggttcagatg ggcgcgcctc tggcggtggc ggatcggaca ttgagctcac ccagtctcca      60

<210> SEQ ID NO 66
<211> LENGTH: 59
<212> TYPE: DNA
<213> ORGANISM: Artificial Sequence
<220> FEATURE:
<223> OTHER INFORMATION: Description of Artificial Sequence:mouse
      V-kappa back primer VK1BACKLi Asc

<400> SEQUENCE: 66
ggttcagatg ggcgcgcctc tggcggtggc ggatcggaca ttgtgatgwc acagtctcc       59

<210> SEQ ID NO 67
<211> LENGTH: 59
<212> TYPE: DNA
<213> ORGANISM: Artificial Sequence
<220> FEATURE:
<223> OTHER INFORMATION: Description of Artificial Sequence:mouse
```

V-kappa back primer VK2BACKLi Asc

<400> SEQUENCE: 67
ggttcagatg ggcgcgcctc tggcggtggc ggatcggatg ttktgatgac ccaaactcc        59

<210> SEQ ID NO 68
<211> LENGTH: 59
<212> TYPE: DNA
<213> ORGANISM: Artificial Sequence
<220> FEATURE:
<223> OTHER INFORMATION: Description of Artificial Sequence:mouse
      V-kappa back primer VK3BACKLi Asc

<400> SEQUENCE: 68
ggttcagatg ggcgcgcctc tggcggtggc ggatcggata ttgtgatrac bcaggcwgc        59

<210> SEQ ID NO 69
<211> LENGTH: 59
<212> TYPE: DNA
<213> ORGANISM: Artificial Sequence
<220> FEATURE:
<223> OTHER INFORMATION: Description of Artificial Sequence:mouse
      V-kappa back primer VK4BACKLi Asc

<400> SEQUENCE: 69
ggttcagatg ggcgcgcctc tggcggtggc ggatcggaca ttgtgctgac mcartctcc        59

<210> SEQ ID NO 70
<211> LENGTH: 59
<212> TYPE: DNA
<213> ORGANISM: Artificial Sequence
<220> FEATURE:
<223> OTHER INFORMATION: Description of Artificial Sequence:mouse
      V-kappa back primer VK5BACKLi Asc

<400> SEQUENCE: 70
ggttcagatg ggcgcgcctc tggcggtggc ggatcgsaaa wtgtkctcac ccagtctcc        59

<210> SEQ ID NO 71
<211> LENGTH: 59
<212> TYPE: DNA
<213> ORGANISM: Artificial Sequence
<220> FEATURE:
<223> OTHER INFORMATION: Description of Artificial Sequence:mouse
      V-kappa back primer VK6BACKLi Asc

<400> SEQUENCE: 71
ggttcagatg ggcgcgcctc tggcggtggc ggatcggaya tyvwgatgac mcagwctcc        59

<210> SEQ ID NO 72
<211> LENGTH: 59
<212> TYPE: DNA
<213> ORGANISM: Artificial Sequence
<220> FEATURE:
<223> OTHER INFORMATION: Description of Artificial Sequence:mouse
      V-kappa back primer VK7BACKLi Asc

<400> SEQUENCE: 72
ggttcagatg ggcgcgcctc tggcggtggc ggatcgcaaa ttgttctcac ccagtctcc        59

<210> SEQ ID NO 73
<211> LENGTH: 59
<212> TYPE: DNA
<213> ORGANISM: Artificial Sequence
<220> FEATURE:
<223> OTHER INFORMATION: Description of Artificial Sequence:mouse
      V-kappa back primer VK8BACKLi Asc

<400> SEQUENCE: 73
ggttcagatg ggcgcgcctc tgcggtggc ggatcgtcat tattgcaggt gcttgtggg    59

<210> SEQ ID NO 74
<211> LENGTH: 42
<212> TYPE: DNA
<213> ORGANISM: Artificial Sequence
<220> FEATURE:
<223> OTHER INFORMATION: Description of Artificial Sequence:mouse
      J-kappa forward primer JK1NOT10

<400> SEQUENCE: 74
gagtcattct gcggccgccc gtttgatttc cagcttggtg cc    42

<210> SEQ ID NO 75
<211> LENGTH: 42
<212> TYPE: DNA
<213> ORGANISM: Artificial Sequence
<220> FEATURE:
<223> OTHER INFORMATION: Description of Artificial Sequence:mouse
      J-kappa forward primer JK2NOT10

<400> SEQUENCE: 75
gagtcattct gcggccgccc gttttatttc cagcttggtc cc    42

<210> SEQ ID NO 76
<211> LENGTH: 42
<212> TYPE: DNA
<213> ORGANISM: Artificial Sequence
<220> FEATURE:
<223> OTHER INFORMATION: Description of Artificial Sequence:mouse
      J-kappa forward primer JK3NOT10

<400> SEQUENCE: 76
gagtcattct gcggccgccc gttttatttc cagtctggtc cc    42

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence:mouse
      J-kappa forward primer JK4NOT10

<400> SEQUENCE: 77
gagtcattct gcggccgccc gttttatttc caactttgtc cc    42

<210> SEQ ID NO 78
<211> LENGTH: 42
<212> TYPE: DNA
<213> ORGANISM: Artificial Sequence
<220> FEATURE:
<223> OTHER INFORMATION: Description of Artificial Sequence:mouse
      J-kappa forward primer JK5NOT10

<400> SEQUENCE: 78
gagtcattct gcggccgccc gtttcagctc cagcttggtc cc    42

<210> SEQ ID NO 79
<211> LENGTH: 74
<212> TYPE: DNA
<213> ORGANISM: Artificial Sequence
<220> FEATURE:
<223> OTHER INFORMATION: Description of Artificial Sequence:
      oligonucleotide mychis6-co -continued

```
<400> SEQUENCE: 79
ggccgcagaa caaaaactca tctcagaaga ggatctgaat ggggcggcac atcaccatca      60
ccatcactaa taag                                                        74

<210> SEQ ID NO 80
<211> LENGTH: 74
<212> TYPE: DNA
<213> ORGANISM: Artificial Sequence
<220> FEATURE:
<223> OTHER INFORMATION: Description of Artificial Sequence:
      oligonucleotide mycchis-ic

<400> SEQUENCE: 80
aattcttatt agtgatggtg atggtgatgt gccgccccat tcagatcctc ttctgagatg      60 agttttttgtt ctgc                                                       74

<210> SEQ ID NO 81
<211> LENGTH: 726
<212> TYPE: DNA
<213> ORGANISM: Artificial Sequence
<220> FEATURE:
<223> OTHER INFORMATION: Description of Artificial Sequence:scFv from
      hybridoma cell line 193/AD3

<400> SEQUENCE: 81
gaggtgaagc tggtggagtc tggacctgag ctgaagaagc ctggagagac agtcaagatc      60
tcctgcaagg cttctgggta tatcttcaca aactatggaa tgaactgggt gaagcaggct     120
ccaggaaagg gtttaaagtg gatgggctgg ataaacacct acactggaga gccaacatat     180
gctgatgact caagggacg gtttgccttc tctttggaaa cctctgccag cactgcctat     240
ttgcagatca acaacctcaa aaatgaggac acggctacat atttctgtgc attatatggt     300
aactccccta aggggtttgc ttactggggc caagggactc tggtcactgt ctctgcaggt     360
ggaggcggtt caggtgggcg cgcctctggc ggtggcggat cggatattca gatgacacag     420
tctcccaaat tcctgcttgt atcagcagga gacagggtta ccataacctg caaggccagt     480
cagagtgtga gtaatgatgt agcttggtac aacagaagc cggggcagtc tcctaaacta     540
ctgatgtact atgcatccaa tcgctacact ggagtccctg atcgcttcac tggcagtgga     600
tatgggacgg atttcacttt caccatcagc actgtgcagg ctgaagacct ggcagtttat     660
ttctgtcagc aggattatgg ctctcctccc acgttcggag ggggcaccaa gctggaaatt     720
aaacgg                                                               726

<210> SEQ ID NO 82
<211> LENGTH: 242
<212> TYPE: PRT
<213> ORGANISM: Artificial Sequence
<220> FEATURE:
<223> OTHER INFORMATION: Description of Artificial Sequence:scFv from
      hybridoma cell line 193/AD3

<400> SEQUENCE: 82

Glu Val Lys Leu Val Glu Ser Gly Pro Glu Leu Lys Lys Pro Gly Glu
  1               5                  10                  15

Thr Val Lys Ile Ser Cys Lys Ala Ser Gly Tyr Ile Phe Thr Asn Tyr
                 20                  25                  30

Gly Met Asn Trp Val Lys Gln Ala Pro Gly Lys Gly Leu Lys Trp Met
             35                  40                  45

Gly Trp Ile Asn Thr Tyr Thr Gly Glu Pro Thr Tyr Ala Asp Asp Phe
```

```
                50                  55                  60
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Leu Tyr Gly Asn Ser Pro Lys Gly Phe Ala Tyr Trp Gly Gln Gly
                100                 105                 110

Thr Leu Val Thr Val Ser Ala Gly Gly Gly Ser Gly Gly Arg Ala
                115                 120                 125

Ser Gly Gly Gly Ser Asp Ile Gln Met Thr Gln Ser Pro Lys Phe
    130                 135                 140

Leu Leu Val Ser Ala Gly Asp Arg Val Thr Ile Thr Cys Lys Ala Ser
145                 150                 155                 160

Gln Ser Val Ser Asn Asp Val Ala Trp Tyr Gln Lys Pro Gly Gln
                165                 170                 175

Ser Pro Lys Leu Leu Met Tyr Tyr Ala Ser Asn Arg Tyr Thr Gly Val
                180                 185                 190

Pro Asp Arg Phe Thr Gly Ser Gly Tyr Gly Thr Asp Phe Thr Phe Thr
                195                 200                 205

Ile Ser Thr Val Gln Ala Glu Asp Leu Ala Val Tyr Phe Cys Gln Gln
    210                 215                 220

Asp Tyr Gly Ser Pro Pro Thr Phe Gly Gly Gly Thr Lys Leu Glu Ile
225                 230                 235                 240

Lys Arg

<210> SEQ ID NO 83
<211> LENGTH: 747
<212> TYPE: DNA
<213> ORGANISM: Artificial Sequence
<220> FEATURE:
<223> OTHER INFORMATION: Description of Artificial Sequence:scFv from
      hybridoma cell line 193/K2

<400> SEQUENCE: 83
gaagtgcagc tggtggagtc tgggggaggc ctagtgaagc tggagggtc cctgaaactc        60 tcctgtgcag cctctggatt cactttcagt acctatacca tgtcttgggt tcgccagact      120
ccggagaaga ggctggagtg ggtcgcaacc attagtagtg gtggtagtta cacctactat      180
ccagacagtg tgaggggccg attcaccatc tccagagaca atgccaagaa caccctgtac      240
ctgcaaatga gcagtctgaa gtctgaggac acagccatgt attactgtac aagagatggg      300
ggacacgggt acgtagtag cttttgactac tggggccaag gcaccactct cacagtctcc      360
tcaggtggag gcggttcagg tgggcgcgcc tctggcggtg gcggatcgca aattgtgctc      420
acccagtctc cactctccct gcctgtcagt cttggagatc aagcctccat ctcttgcaga      480
tctagtcaga gcattgtaca tagtaatgga aacacctatt tagaatggta cctgcagaaa      540
ccaggccagt ctccaaagct cctgatctac aaagtttcca accgattttc tggggtccca      600
gacaaattca gtggcagtgg atcagggaca gatttcacac tcaagatcag cagagtggag      660
gctgaggatc tgggagttta ttactgcttt caaggttcac atgttccgtg gacgttcggt      720
ggaggcacca agctggaaat caaacgg                                          747

<210> SEQ ID NO 84
<211> LENGTH: 249
<212> TYPE: PRT
<213> ORGANISM: Artificial Sequence
```

```
<220> FEATURE:
<223> OTHER INFORMATION: Description of Artificial Sequence:scFv from
      hybridoma cell line 193/K2

<400> SEQUENCE: 84

Glu Val Gln Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Thr Tyr
             20                  25                  30

Thr Met Ser Trp Val Arg Gln Thr Pro Glu Lys Arg Leu Glu Trp Val
         35                  40                  45

Ala Thr Ile Ser Ser Gly Gly Ser Tyr Thr Tyr Tyr Pro Asp Ser Val
     50                  55                  60

Arg Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Thr Arg Asp Gly Gly His Gly Tyr Gly Ser Ser Phe Asp Tyr Trp Gly
            100                 105                 110

Gln Gly Thr Thr Leu Thr Val Ser Ser Gly Gly Gly Ser Gly Gly
        115                 120                 125

Arg Ala Ser Gly Gly Gly Ser Gln Ile Val Leu Thr Gln Ser Pro
    130                 135                 140

Leu Ser Leu Pro Val Ser Leu Gly Asp Gln Ala Ser Ile Ser Cys Arg
145                 150                 155                 160

Ser Ser Gln Ser Ile Val His Ser Asn Gly Asn Thr Tyr Leu Glu Trp
                165                 170                 175

Tyr Leu Gln Lys Pro Gly Gln Ser Pro Lys Leu Leu Ile Tyr Lys Val
            180                 185                 190

Ser Asn Arg Phe Ser Gly Val Pro Asp Lys Phe Ser Gly Ser Gly Ser
        195                 200                 205

Gly Thr Asp Phe Thr Leu Lys Ile Ser Arg Val Glu Ala Glu Asp Leu
    210                 215                 220

Gly Val Tyr Tyr Cys Phe Gln Gly Ser His Val Pro Trp Thr Phe Gly
225                 230                 235                 240

Gly Gly Thr Lys Leu Glu Ile Lys Arg
                245

<210> SEQ ID NO 85
<211> LENGTH: 747
<212> TYPE: DNA
<213> ORGANISM: Artificial Sequence
<220> FEATURE:
<223> OTHER INFORMATION: Description of Artificial Sequence:scFv from
      hybridoma cell line 198/AB2 (subclone of 198/B1)

<400> SEQUENCE: 85
gaggtgcagc ttcaggagtc agggggaggc ttagtgaagc ctggagggtc cctgaaactc      60
tcctgtgcag cctctggatt cactttcagt agctatacca tgtcttgggt tcgccagact     120
ccggagaaga ggctggagtg ggtcgcaacc attagtagtg gtggtagttc cacctactat     180
ccagacagtg tgaagggccg attcaccatc tccagagaca tgccaagaa cacccctgtac     240 ctgcaaatga gcagtctgag gtctgaggac acagccatgt attactgtac aagagagggg     300
ggtggtttca ccgtcaactg gtacttcgat gtctggggcg cagggactct ggtcactgtc     360
tctgcaggtg gaggcggttc aggtgggcgc gcctctggcg gtggcggatc ggaaaatgtg     420
```

-continued

```
ctcacccagt ctccagcttc tttggctgtg tctctagggc agagggccac catatcctgc    480
agagccagtg aaagtgttga tagttatggc tataatttta tgcactggta tcagcagata    540
ccaggacagc cacccaaact cctcatctat cgtgcatcca acctagagtc tgggatccct    600
gccaggttca gtggcagtgg gtctaggaca gacttcaccc tcaccattaa tcctgtggag    660
gctgatgatg ttgcaaccta ttactgtcag caaagtaatg aggatccgct cacgttcggt    720
actgggacca gactggaaat aaaacgg                                        747
```

<210> SEQ ID NO 86
<211> LENGTH: 249
<212> TYPE: PRT
<213> ORGANISM: Artificial Sequence
<220> FEATURE:
<223> OTHER INFORMATION: Description of Artificial Sequence:scFv from hybridoma cell line 198/AB2 (subclone of 198/B1)

<400> SEQUENCE: 86

```
Glu Val Gln Leu Gln Glu Ser Gly Gly Gly Leu Val Lys Pro Gly Gly
  1               5                  10                  15

Ser Leu Lys Leu Ser Cys Ala Ala Ser Gly Phe Thr Phe Ser Ser Tyr
             20                  25                  30

Thr Met Ser Trp Val Arg Gln Thr Pro Glu Lys Arg Leu Glu Trp Val
         35                  40                  45

Ala Thr Ile Ser Ser Gly Gly Ser Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Thr Arg Glu Gly Gly Gly Phe Thr Val Asn Trp Tyr Phe Asp Val Trp
            100                 105                 110

Gly Ala Gly Thr Leu Val Thr Val Ser Ala Gly Gly Gly Ser Gly
        115                 120                 125

Gly Arg Ala Ser Gly Gly Gly Ser Glu Asn Val Leu Thr Gln Ser
    130                 135                 140

Pro Ala Ser Leu Ala Val Ser Leu Gly Gln Arg Ala Thr Ile Ser Cys
145                 150                 155                 160

Arg Ala Ser Glu Ser Val Asp Ser Tyr Gly Tyr Asn Phe Met His Trp
                165                 170                 175

Tyr Gln Gln Ile Pro Gly Gln Pro Pro Lys Leu Leu Ile Tyr Arg Ala
            180                 185                 190

Ser Asn Leu Glu Ser Gly Ile Pro Ala Arg Phe Ser Gly Ser Gly Ser
        195                 200                 205

Arg Thr Asp Phe Thr Leu Thr Ile Asn Pro Val Glu Ala Asp Asp Val
    210                 215                 220

Ala Thr Tyr Tyr Cys Gln Gln Ser Asn Glu Asp Pro Leu Thr Phe Gly
225                 230                 235                 240

Thr Gly Thr Arg Leu Glu Ile Lys Arg
                245
```

<210> SEQ ID NO 87
<211> LENGTH: 747
<212> TYPE: DNA
<213> ORGANISM: Artificial Sequence
<220> FEATURE:
<223> OTHER INFORMATION: Description of Artificial Sequence:scFv derived from hybridima cell line 198/A1

-continued

<220> FEATURE:
<221> NAME/KEY: modified_base
<222> LOCATION: (1)..(747)
<223> OTHER INFORMATION: n = g, a, c or t

<400> SEQUENCE: 87

```
gaggtgcagc ttcaggagtc agggggaggc ttagtgaagc ctggagggtc cctgaaactc      60
tcctgtgcag cctctggatt cattttagt agttatacca tgtcttgggt tcgccagact      120
ccggagaaga ggctggagtg ggtcgcaacc attagtagtg gtggtagttc cacctactat     180
ccagacagtg tgaagggccg attcaccatc tccagagaca tgccaagaa caccctgtac      240
ctgcaaatga gcagtctgaa gtctgaggac acagccatgt atcactgtac aagagagggg     300
ggtggttatt acgtcaactg gtacttcgat gtctggggcg caggcaccac tctcacagtc     360
tcctcaggtg gaggcggttc aggtgggcgc gcctctggcg gtggcggatc ggacattgag     420
ctcacncagt ctccagcttc tttggctgtg tctctaggc agagggccac catatcctgc      480
agagccagtg aaagtgttga tagttatggc aagagtttta tgcactggta ccagcagaaa     540
ccagggcagc cacccaaact cctcatctat cgtgcatcca acctagaatc tgggatccct     600
gccaggttca gtggcagtgg gtctaggaca gacttcaccc tcaccattaa tcctgtggag     660
gctgatgatg ttgcnaccta ttactgtcag caaagtaatg aggatcccct cacgttcggt     720
gctgggacca gactggaaat aaaacgg                                         747
```

<210> SEQ ID NO 88
<211> LENGTH: 249
<212> TYPE: PRT
<213> ORGANISM: Artificial Sequence
<220> FEATURE:
<223> OTHER INFORMATION: Description of Artificial Sequence:scFv derived
from hybridima cell line 198/A1

<400> SEQUENCE: 88

```
Glu Val Gln Leu Gln Glu Ser Gly Gly Gly Leu Val Lys Pro Gly Gly
 1               5                   10                  15

Ser Leu Lys Leu Ser Cys Ala Ala Ser Gly Phe Ile Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Ser Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr His Cys
                85                  90                  95

Thr Arg Glu Gly Gly Gly Tyr Tyr Val Asn Trp Tyr Phe Asp Val Trp
            100                 105                 110

Gly Ala Gly Thr Thr Leu Thr Val Ser Ser Gly Gly Gly Gly Ser Gly
        115                 120                 125

Gly Arg Ala Ser Gly Gly Gly Gly Ser Asp Ile Glu Leu Thr Gln Ser
    130                 135                 140

Pro Ala Ser Leu Ala Val Ser Leu Gly Gln Arg Ala Thr Ile Ser Cys
145                 150                 155                 160

Arg Ala Ser Glu Ser Val Asp Ser Tyr Gly Lys Ser Phe Met His Trp
                165                 170                 175

Tyr Gln Gln Lys Pro Gly Gln Pro Pro Lys Leu Leu Ile Tyr Arg Ala
            180                 185                 190
```

```
Ser Asn Leu Glu Ser Gly Ile Pro Ala Arg Phe Ser Gly Ser Gly Ser
        195                 200                 205

Arg Thr Asp Phe Thr Leu Thr Ile Asn Pro Val Glu Ala Asp Asp Val
    210                 215                 220

Ala Thr Tyr Tyr Cys Gln Gln Ser Asn Glu Asp Pro Leu Thr Phe Gly
225                 230                 235                 240

Ala Gly Thr Arg Leu Glu Ile Lys Arg
                245

<210> SEQ ID NO 89
<211> LENGTH: 2199
<212> TYPE: DNA
<213> ORGANISM: Artificial Sequence
<220> FEATURE:
<223> OTHER INFORMATION: Description of Artificial Sequence:198A2
      scFv-alkaline phosphatase fusion protein (ORF of expression
      vector pDAP2-198AB2#100)
<220> FEATURE:
<221> NAME/KEY: modified_base
<222> LOCATION: (228)
<223> OTHER INFORMATION: n = g, a, c or t

<400> SEQUENCE: 89
atgaaatacc tattgcctac ggcagccgct ggattgttat tactcgcggc ccagccggcc      60
atggcggagg tgaagctggt ggagtctggg ggaggcttag tgaagcctgg agggtccctg     120
aaactctcct gtgcagcctc tggattcact ttcagtagct ataccatgtc ttgggttcgc     180
cagactccgg agaagaggct ggagtgggtc gcaaccatta gtagtggngg tagttccacc     240
tactatccag acagtgtgaa gggccgattc accatctcca gagacaatgc aagaacacc      300 ctgtacctgc aaatgagcag tctgaggtct gaggacacac catgtatta ctgtacaaga      360 gagggggtg gtttcaccgt caactggtac ttcgatgtct ggggcgcagg aacctcagtc      420
accgtctcct caggtggagg cggttcaggt gggcgcgcct ggcggtgg cggatcggac       480 attgtgctga cacagtctcc agcttctttg gctgtgtctc tagggcagag ggccaccata     540
tcctgcagag ccagtgaaag tgttgatagt tatggcgtata attttatgca ctggtatcag    600
cagataccag acagccacc caaactcctc atctatcgtg catccaacct agagtctggg     660
atccctgcca ggttcagtgg cagtgggtct aggacagact tcaccctcac cattaatcct     720
gtggaggctg atgatgttgc aacctattac tgtcagcaaa gtaatgagga tccgctcacg     780
ttcggtactg ggaccagact ggaaataaaa cgggcggccg cagcccgggc accagaaatg     840
cctgttctgg aaaaccgggc tgctcagggc gatattactg caccggcgg tgctcgccgt     900 ttaacgggtg atcagactgc cgctctgcgt gattctctta gcgataaacc tgcaaaaaat     960
attattttgc tgattggcga tgggatgggg gactcggaaa ttactgccgc acgtaattat    1020
gccgaaggtg cgggcggctt ttttaaggt atagatgcct accgcttac cgggcaatac     1080 actcactatg cgctgaataa aaaaaccggc aaaccggact acgtcaccga ctcggctgca    1140
tcagcaaccg cctggtcaac cggtgtcaaa acctataacg gcgcgctggg cgtcgatatt    1200
cacgaaaaag atcacccaac gattctggaa atggcaaaag ccgcaggtct ggcgaccggt    1260
aacgtttcta ccgcagagtt gcaggatgcc acgcccgctg cgctggtggc acatgtgacc    1320
tcgcgcaaat gctacggtcc gagcgcgacc agtgaaaaat gtccgggtaa cgctctggaa    1380
aaaggcggaa aaggatcgat taccgaacag ctgcttaacg ctcgtgccga cgttacgctt    1440
ggcggcggcg caaaaacctt tgctgaaacg gcaaccgctg tgaatggca gggaaaaacg    1500
```

-continued

```
ctgcgtgaac aggcacaggc gcgtggttat cagttggtga gcgatgctgc ctcactgaat    1560
tcggtgacgg aagcgaatca gcaaaaaccc ctgcttggcc tgtttgctga cggcaatatg    1620
ccagtgcgct ggctaggacc gaaagcaacg taccatggca atatcgataa gcccgcagtc    1680
acctgtacgc caaatccgca acgtaatgac agtgtaccaa ccctggcgca gatgaccgac    1740
aaagccattg aattgttgag taaaaatgag aaaggctttt tcctgcaagt tgaaggtgcg    1800
tcaatcgata acaggatca tgctgcgaat ccttgtgggc aaattggcga gacggtcgat    1860
ctcgatgaag ccgtacaacg ggcgctggaa ttcgctaaaa aggagggtaa cacgctggtc    1920
atagtcaccg ctgatcacgc ccacgccagc cagattgttg cgccggatac caaagctccg    1980
ggcctcaccc aggcgctaaa taccaaagat ggcgcagtga tggtgatgag ttacgggaac    2040
tccgaagagg attcacaaga acataccggc agtcagttgc gtattgcggc gtatggcccg    2100
catgccgcca atgttgttgg actgaccgac cagaccgatc tcttctacac catgaaagcc    2160
gctctggggg atatcgcaca ccatcaccat caccattaa                           2199
```

<210> SEQ ID NO 90
<211> LENGTH: 732
<212> TYPE: PRT
<213> ORGANISM: Artificial Sequence
<220> FEATURE:
<223> OTHER INFORMATION: Description of Artificial Sequence:198A2 scFv-alkaline phosphatase fusion protein (ORF of expression vector pDAP2-198AB2#100)

<400> SEQUENCE: 90

```
Met Lys Tyr Leu Leu Pro Thr Ala Ala Ala Gly Leu Leu Leu Leu Ala
 1               5                  10                  15

Ala Gln Pro Ala Met Ala Glu Val Lys Leu Val Glu Ser Gly Gly Gly
                20                  25                  30

Leu Val Lys Pro Gly Gly Ser Leu Lys Leu Ser Cys Ala Ala Ser Gly
            35                  40                  45

Phe Thr Phe Ser Ser Tyr Thr Met Ser Trp Val Arg Gln Thr Pro Glu
        50                  55                  60

Lys Arg Leu Glu Trp Val Ala Thr Ile Ser Gly Gly Ser Ser Thr
 65                  70                  75                  80

Tyr Tyr Pro Asp Ser Val Lys Gly Arg Phe Thr Ile Ser Arg Asp Asn
                85                  90                  95

Ala Lys Asn Thr Leu Tyr Leu Gln Met Ser Ser Leu Arg Ser Glu Asp
            100                 105                 110

Thr Ala Met Tyr Tyr Cys Thr Arg Glu Gly Gly Phe Thr Val Asn
        115                 120                 125

Trp Tyr Phe Asp Val Trp Gly Ala Gly Thr Ser Val Thr Val Ser Ser
    130                 135                 140

Gly Gly Gly Gly Ser Gly Gly Arg Ala Ser Gly Gly Gly Ser Asp
145                 150                 155                 160

Ile Val Leu Thr Gln Ser Pro Ala Ser Leu Ala Val Ser Leu Gly Gln
                165                 170                 175

Arg Ala Thr Ile Ser Cys Arg Ala Ser Glu Ser Val Asp Ser Tyr Gly
            180                 185                 190

Tyr Asn Phe Met His Trp Tyr Gln Gln Ile Pro Gly Gln Pro Pro Lys
        195                 200                 205

Leu Leu Ile Tyr Arg Ala Ser Asn Leu Glu Ser Gly Ile Pro Ala Arg
    210                 215                 220

Phe Ser Gly Ser Gly Ser Arg Thr Asp Phe Thr Leu Thr Ile Asn Pro
```

-continued

```
            225                 230                 235                 240
        Val Glu Ala Asp Asp Val Ala Thr Tyr Tyr Cys Gln Gln Ser Asn Glu
                        245                 250                 255

Asp Pro Leu Thr Phe Gly Thr Gly Thr Arg Leu Glu Ile Lys Arg Ala
                    260                 265                 270

Ala Ala Ala Arg Ala Pro Glu Met Pro Val Leu Glu Asn Arg Ala Ala
                275                 280                 285

Gln Gly Asp Ile Thr Ala Pro Gly Gly Ala Arg Arg Leu Thr Gly Asp
            290                 295                 300

Gln Thr Ala Ala Leu Arg Asp Ser Leu Ser Asp Lys Pro Ala Lys Asn
        305                 310                 315                 320

Ile Ile Leu Leu Ile Gly Asp Gly Met Gly Asp Ser Glu Ile Thr Ala
                        325                 330                 335

Ala Arg Asn Tyr Ala Glu Gly Ala Gly Gly Phe Phe Lys Gly Ile Asp
                    340                 345                 350

Ala Leu Pro Leu Thr Gly Gln Tyr Thr His Tyr Ala Leu Asn Lys Lys
                355                 360                 365

Thr Gly Lys Pro Asp Tyr Val Thr Asp Ser Ala Ala Ser Ala Thr Ala
            370                 375                 380

Trp Ser Thr Gly Val Lys Thr Tyr Asn Gly Ala Leu Gly Val Asp Ile
        385                 390                 395                 400

His Glu Lys Asp His Pro Thr Ile Leu Glu Met Ala Lys Ala Ala Gly
                        405                 410                 415

Leu Ala Thr Gly Asn Val Ser Thr Ala Glu Leu Gln Asp Ala Thr Pro
                    420                 425                 430

Ala Ala Leu Val Ala His Val Thr Ser Arg Lys Cys Tyr Gly Pro Ser
                435                 440                 445

Ala Thr Ser Glu Lys Cys Pro Gly Asn Ala Leu Glu Lys Gly Gly Lys
            450                 455                 460

Gly Ser Ile Thr Glu Gln Leu Leu Asn Ala Arg Ala Asp Val Thr Leu
        465                 470                 475                 480

Gly Gly Gly Ala Lys Thr Phe Ala Glu Thr Ala Thr Ala Gly Glu Trp
                        485                 490                 495

Gln Gly Lys Thr Leu Arg Glu Gln Ala Gln Ala Arg Gly Tyr Gln Leu
                    500                 505                 510

Val Ser Asp Ala Ala Ser Leu Asn Ser Val Thr Glu Ala Asn Gln Gln
                515                 520                 525

Lys Pro Leu Leu Gly Leu Phe Ala Asp Gly Asn Met Pro Val Arg Trp
            530                 535                 540

Leu Gly Pro Lys Ala Thr Tyr His Gly Asn Ile Asp Lys Pro Ala Val
        545                 550                 555                 560

Thr Cys Thr Pro Asn Pro Gln Arg Asn Asp Ser Val Pro Thr Leu Ala
                        565                 570                 575

Gln Met Thr Asp Lys Ala Ile Glu Leu Leu Ser Lys Asn Glu Lys Gly
                    580                 585                 590

Phe Phe Leu Gln Val Glu Gly Ala Ser Ile Asp Lys Gln Asp His Ala
                595                 600                 605

Ala Asn Pro Cys Gly Gln Ile Gly Glu Thr Val Asp Leu Asp Glu Ala
            610                 615                 620

Val Gln Arg Ala Leu Glu Phe Ala Lys Lys Glu Gly Asn Thr Leu Val
        625                 630                 635                 640

Ile Val Thr Ala Asp His Ala His Ala Ser Gln Ile Val Ala Pro Asp
                        645                 650                 655
```

```
Thr Lys Ala Pro Gly Leu Thr Gln Ala Leu Asn Thr Lys Asp Gly Ala
            660                 665                 670

Val Met Val Met Ser Tyr Gly Asn Ser Glu Glu Asp Ser Gln Glu His
        675                 680                 685

Thr Gly Ser Gln Leu Arg Ile Ala Ala Tyr Gly Pro His Ala Ala Asn
    690                 695                 700

Val Val Gly Leu Thr Asp Gln Thr Asp Leu Phe Tyr Thr Met Lys Ala
705                 710                 715                 720

Ala Leu Gly Asp Ile Ala His His His His His His
                725                 730

<210> SEQ ID NO 91
<211> LENGTH: 978
<212> TYPE: DNA
<213> ORGANISM: Artificial Sequence
<220> FEATURE:
<223> OTHER INFORMATION: Description of Artificial Sequence:plasmid
      pZip-198AB2#102
<220> FEATURE:
<221> NAME/KEY: modified_base
<222> LOCATION: (1)..(978)
<223> OTHER INFORMATION: n = g, a, c or t

<400> SEQUENCE: 91
```

| | | | |
|---|---|---|---|
| atgaaatacc tattgcctac ggcagccgct ggattgttat tactcgcggc ccagccggcc | 60 |
| atggcggagg tgaagctggt ggagtctggg ggaggcttag tgaagcctgg agggtccctg | 120 |
| aaactctcct gtgcagcctc tggattcact ttcagtagct ataccatgtc ttgggttcgc | 180 |
| cagactccgg agaagaggct ggagtgggtc gcaaccatta gtagtggngg tagttccacc | 240 |
| tactatccag acagtgtgaa gggccgattc accatctcca gagacaatgc caagaacacc | 300 |
| ctgtacctgc aaatgagcag tctgaggtct gaggacacag ccatgtatta ctgtacaaga | 360 |
| gagggggtg gtttcaccgt caactggtac ttcgatgtct ggggcgcagg aacctcagtc | 420 |
| accgtctcct caggtggagg cggttcaggt gggcgcgcct ctggcggtgg cggatcggac | 480 |
| attgtgctga cacagtntcc agcttctttg gctgtgtctc tagggcagag ggccaccata | 540 |
| tcntgcagag ccagtgaaag tgttgatagt tatggctata attttatgca ctggtatcag | 600 |
| cagataccag acagccacc caaactcctc atctatcgtg catccaacct agagtctggg | 660 |
| atccctgcca ggttcagtgg cagtgggtct aggacagact tcaccctcac cattaatcct | 720 |
| gtggaggctg atgatgttgc aacctattac tgtcagcaaa gtaatgagga tccgctcacg | 780 |
| ttcggtactg ggaccagact ggaaataaaa cgggcggccg caccgaagcc ttccactccg | 840 |
| cccgggtctt cccgtatgaa acagctgaa gacaaagtag aggagctcct tagcaagaac | 900 |
| taccatctag aaaacgaggt agctcgtctg aaaaagcttg ttggtgaacg tggtggtcac | 960 |
| catcaccatc accattaa | 978 |

```
<210> SEQ ID NO 92
<211> LENGTH: 325
<212> TYPE: PRT
<213> ORGANISM: Artificial Sequence
<220> FEATURE:
<223> OTHER INFORMATION: Description of Artificial Sequence:plasmid
      pZip-198AB2#102
<220> FEATURE:
<221> NAME/KEY: MOD_RES
<222> LOCATION: (166)
<223> OTHER INFORMATION: Xaa = Cys, Tyr, Ser or Phe

<400> SEQUENCE: 92
```

```
Met Lys Tyr Leu Leu Pro Thr Ala Ala Ala Gly Leu Leu Leu Ala
 1               5                  10                  15

Ala Gln Pro Ala Met Ala Glu Val Lys Leu Val Glu Ser Gly Gly Gly
                20                  25                  30

Leu Val Lys Pro Gly Gly Ser Leu Lys Leu Ser Cys Ala Ala Ser Gly
            35                  40                  45

Phe Thr Phe Ser Ser Tyr Thr Met Ser Trp Val Arg Gln Thr Pro Glu
        50                  55                  60

Lys Arg Leu Glu Trp Val Ala Thr Ile Ser Ser Gly Gly Ser Ser Thr
 65              70                  75                  80

Tyr Tyr Pro Asp Ser Val Lys Gly Arg Phe Thr Ile Ser Arg Asp Asn
                85                  90                  95

Ala Lys Asn Thr Leu Tyr Leu Gln Met Ser Ser Leu Arg Ser Glu Asp
            100                 105                 110

Thr Ala Met Tyr Tyr Cys Thr Arg Glu Gly Gly Gly Phe Thr Val Asn
        115                 120                 125

Trp Tyr Phe Asp Val Trp Gly Ala Gly Thr Ser Val Thr Val Ser Ser
130                 135                 140

Gly Gly Gly Gly Ser Gly Gly Arg Ala Ser Gly Gly Gly Ser Asp
145                 150                 155                 160

Ile Val Leu Thr Gln Xaa Pro Ala Ser Leu Ala Val Ser Leu Gly Gln
            165                 170                 175

Arg Ala Thr Ile Ser Cys Arg Ala Ser Glu Ser Val Asp Ser Tyr Gly
            180                 185                 190

Tyr Asn Phe Met His Trp Tyr Gln Gln Ile Pro Gly Gln Pro Pro Lys
        195                 200                 205

Leu Leu Ile Tyr Arg Ala Ser Asn Leu Glu Ser Gly Ile Pro Ala Arg
        210                 215                 220

Phe Ser Gly Ser Gly Ser Arg Thr Asp Phe Thr Leu Thr Ile Asn Pro
225                 230                 235                 240

Val Glu Ala Asp Asp Val Ala Thr Tyr Tyr Cys Gln Gln Ser Asn Glu
                245                 250                 255

Asp Pro Leu Thr Phe Gly Thr Gly Thr Arg Leu Glu Ile Lys Arg Ala
            260                 265                 270

Ala Ala Pro Lys Pro Ser Thr Pro Pro Gly Ser Ser Arg Met Lys Gln
        275                 280                 285

Leu Glu Asp Lys Val Glu Glu Leu Leu Ser Lys Asn Tyr His Leu Glu
        290                 295                 300

Asn Glu Val Ala Arg Leu Lys Lys Leu Val Gly Glu Arg Gly Gly His
305                 310                 315                 320

His His His His His
            325
```

<210> SEQ ID NO 93
<211> LENGTH: 2190
<212> TYPE: DNA
<213> ORGANISM: Artificial Sequence
<220> FEATURE:
<223> OTHER INFORMATION: Description of Artificial Sequence:mAB#8860
      scFv-alkaline phosphatase fusion protein (vector construct
      pDAP2-8860scFv#11)

<400> SEQUENCE: 93
atgaaatacc tattgcctac ggcagccgct ggattgttat tactcgcggc ccagccggcc      60
atggccgagg ttcagcttca gcagtctgga cctgagctgg tgaagcccgg ggcctcagtg     120

-continued

```
aagatttcct gcaaagcttc tggctacgca ttcagtagct cttggatgaa ctgggtgaag      180
cagaggcctg acagggtct tgagtggatt ggacggattt atcctggaaa tggagatact       240
aactacaatg ggaagttcaa gggcaaggcc acactgactg cagacaaatc ctccagcaca      300
gcctacatgc agctcagcag cctgacctct gtggactctg cggtctattt ctgtgcagat      360
ggtaacgtat attactatgc tatggactac tggggtcaag aacctcagt caccgtctcc       420 tcaggtggag gcggttcagg tgggcgcgcc tctggcggtg gcggatcgca aattgttctc      480
acccagtctc ctgcttcctt agctgtatct ctggggcaga gggccaccat ctcatgcagg      540
gccagcaaaa gtgtcagtac atctggctat agttatatgc actggtacca acagaaacca     600
ggacagccac ccaaactcct catctatctt gcatccaacc tagaatctgg ggtccctgcc      660
aggttcagtg gcagtgggtc tgggacagac ttcaccctca acatccatcc tgtggaggag      720
gaggatgctg caacctatta ctgtcagcac agtagggagc ttcctcggac gttcggtgga     780
ggcaccaagc tggaaatcaa acgggcggcc gcagcccggg caccagaaat gcctgttctg     840
gaaaaccggg ctgctcaggg cgatattact gcacccggcg tgctcgccg tttaacgggt     900 gatcagactg ccgctctgcg tgattctctt agcgataaac ctgcaaaaaa tattattttg     960
ctgattggcg atgggatggg ggactcggaa attactgccg cacgtaatta tgccgaaggt    1020
gcgggcggct ttttaaagg tatagatgcc ttaccgctta ccgggcaata cactcactat     1080
gcgctgaata aaaaaaccgg caaaccggac tacgtcaccg actcggctgc atcagcaacc   1140
gcctggtcaa ccggtgtcaa aacctataac ggcgcgctgg gcgtcgatat tcacgaaaaa  1200
gatcacccaa cgattctgga atggcaaaa gccgcaggtc tggcgaccgg taacgtttct    1260
accgcagagt tgcaggatgc cacgcccgct gcgctggtgg cacatgtgac ctcgcgcaaa  1320
tgctacggtc cgagcgcgac cagtgaaaaa tgtccgggta acgctctgga aaaggcgga   1380 aaaggatcga ttaccgaaca gctgcttaac gctcgtgccg acgttacgct ggcggcggc    1440 gcaaaaacct tgctgaaaac ggcaaccgct ggtgaatggc agggaaaaac gctgcgtgaa  1500
caggcacagg cgcgtggtta tcagttggtg agcgatgctg cctcactgaa ttcggtgacg   1560
gaagcgaatc agcaaaaacc cctgcttggc ctgtttgctg acggcaatat gccagtgcgc  1620
tggctaggac cgaaagcaac gtaccatggc aatatcgata gcccgcagt cacctgtacg    1680 ccaaatccgc aacgtaatga cagtgtacca ccctggcgc agatgaccga caaagccatt    1740
gaattgttga gtaaaaatga gaaggctttt tcctgcaag ttgaaggtgc gtcaatcgat    1800
aaacaggatc atgctgcgaa tccttgtggg caaattggcg agacggtcga tctcgatgaa  1860
gccgtacaac gggcgctgga attcgctaaa aaggaggta acacgctggt catagtcacc   1920
gctgatcacg cccacgccag ccagattgtt gcgccggata ccaaagctcc gggcctcacc  1980
caggcgctaa ataccaaaga tggcgcagtg atggtgatga gttacgggaa ctccgaagag  2040
gattcacaag aacataccgg cagtcagttg cgtattgcgg cgtatggccc gcatgccgcc  2100
aatgttgttg gactgaccga ccagaccgat ctcttctaca ccatgaaagc cgctctgggg  2160
gatatcgcac accatcacca tcaccattaa                                     2190
```

<210> SEQ ID NO 94
<211> LENGTH: 729
<212> TYPE: PRT
<213> ORGANISM: Artificial Sequence
<220> FEATURE:
<223> OTHER INFORMATION: Description of Artificial Sequence:mAB#8860
      scFv-alkaline phosphatase fusion protein (vector construct pDAP2-8860scFv#11)

<400> SEQUENCE: 94

```
Met Lys Tyr Leu Leu Pro Thr Ala Ala Ala Gly Leu Leu Leu Ala
  1               5                  10                  15

Ala Gln Pro Ala Met Ala Glu Val Gln Leu Gln Gln Ser Gly Pro Glu
             20                  25                  30

Leu Val Lys Pro Gly Ala Ser Val Lys Ile Ser Cys Lys Ala Ser Gly
             35                  40                  45

Tyr Ala Phe Ser Ser Ser Trp Met Asn Trp Val Lys Gln Arg Pro Gly
         50                  55                  60

Gln Gly Leu Glu Trp Ile Gly Arg Ile Tyr Pro Gly Asn Gly Asp Thr
 65                  70                  75                  80

Asn Tyr Asn Gly Lys Phe Lys Gly Lys Ala Thr Leu Thr Ala Asp Lys
                 85                  90                  95

Ser Ser Ser Thr Ala Tyr Met Gln Leu Ser Ser Leu Thr Ser Val Asp
                100                 105                 110

Ser Ala Val Tyr Phe Cys Ala Asp Gly Asn Val Tyr Tyr Ala Met
                115                 120                 125

Asp Tyr Trp Gly Gln Gly Thr Ser Val Thr Val Ser Ser Gly Gly Gly
    130                 135                 140

Gly Ser Gly Gly Arg Ala Ser Gly Gly Gly Ser Gln Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Lys Ser Val Ser Thr Ser Gly Tyr Ser Tyr
                180                 185                 190

Met His Trp Tyr Gln Gln Lys Pro Gly Gln Pro Pro Lys Leu Leu Ile
    195                 200                 205

Tyr Leu Ala Ser Asn Leu Glu Ser Gly Val Pro Ala Arg Phe Ser Gly
    210                 215                 220

Ser Gly Ser Gly Thr Asp Phe Thr Leu Asn Ile His Pro Val Glu Glu
225                 230                 235                 240

Glu Asp Ala Ala Thr Tyr Tyr Cys Gln His Ser Arg Glu Leu Pro Arg
                245                 250                 255

Thr Phe Gly Gly Gly Thr Lys Leu Glu Ile Lys Arg Ala Ala Ala Ala
                260                 265                 270

Arg Ala Pro Glu Met Pro Val Leu Glu Asn Arg Ala Ala Gln Gly Asp
    275                 280                 285

Ile Thr Ala Pro Gly Gly Ala Arg Arg Leu Thr Gly Asp Gln Thr Ala
    290                 295                 300

Ala Leu Arg Asp Ser Leu Ser Asp Lys Pro Ala Lys Asn Ile Ile Leu
305                 310                 315                 320

Leu Ile Gly Asp Gly Met Gly Asp Ser Glu Ile Thr Ala Ala Arg Asn
                325                 330                 335

Tyr Ala Glu Gly Ala Gly Gly Phe Phe Lys Gly Ile Asp Ala Leu Pro
                340                 345                 350

Leu Thr Gly Gln Tyr Thr His Tyr Ala Leu Asn Lys Lys Thr Gly Lys
        355                 360                 365

Pro Asp Tyr Val Thr Asp Ser Ala Ala Ser Ala Thr Ala Trp Ser Thr
    370                 375                 380

Gly Val Lys Thr Tyr Asn Gly Ala Leu Gly Val Asp Ile His Glu Lys
385                 390                 395                 400
```

```
Asp His Pro Thr Ile Leu Glu Met Ala Lys Ala Ala Gly Leu Ala Thr
                405                 410                 415

Gly Asn Val Ser Thr Ala Glu Leu Gln Asp Ala Thr Pro Ala Ala Leu
            420                 425                 430

Val Ala His Val Thr Ser Arg Lys Cys Tyr Gly Pro Ser Ala Thr Ser
        435                 440                 445

Glu Lys Cys Pro Gly Asn Ala Leu Glu Lys Gly Lys Gly Ser Ile
450                 455                 460

Thr Glu Gln Leu Leu Asn Ala Arg Ala Asp Val Thr Leu Gly Gly
465                 470                 475                 480

Ala Lys Thr Phe Ala Glu Thr Ala Thr Ala Gly Glu Trp Gln Gly Lys
                485                 490                 495

Thr Leu Arg Glu Gln Ala Gln Ala Arg Gly Tyr Gln Leu Val Ser Asp
            500                 505                 510

Ala Ala Ser Leu Asn Ser Val Thr Glu Ala Asn Gln Gln Lys Pro Leu
        515                 520                 525

Leu Gly Leu Phe Ala Asp Gly Asn Met Pro Val Arg Trp Leu Gly Pro
530                 535                 540

Lys Ala Thr Tyr His Gly Asn Ile Asp Lys Pro Ala Val Thr Cys Thr
545                 550                 555                 560

Pro Asn Pro Gln Arg Asn Asp Ser Val Pro Thr Leu Ala Gln Met Thr
                565                 570                 575

Asp Lys Ala Ile Glu Leu Leu Ser Lys Asn Glu Lys Gly Phe Phe Leu
            580                 585                 590

Gln Val Glu Gly Ala Ser Ile Asp Lys Gln Asp His Ala Ala Asn Pro
        595                 600                 605

Cys Gly Gln Ile Gly Glu Thr Val Asp Leu Asp Glu Ala Val Gln Arg
610                 615                 620

Ala Leu Glu Phe Ala Lys Lys Glu Gly Asn Thr Leu Val Ile Val Thr
625                 630                 635                 640

Ala Asp His Ala His Ala Ser Gln Ile Val Ala Pro Asp Thr Lys Ala
                645                 650                 655

Pro Gly Leu Thr Gln Ala Leu Asn Thr Lys Asp Gly Ala Val Met Val
            660                 665                 670

Met Ser Tyr Gly Asn Ser Glu Glu Asp Ser Gln Glu His Thr Gly Ser
        675                 680                 685

Gln Leu Arg Ile Ala Ala Tyr Gly Pro His Ala Ala Asn Val Val Gly
690                 695                 700

Leu Thr Asp Gln Thr Asp Leu Phe Tyr Thr Met Lys Ala Ala Leu Gly
705                 710                 715                 720

Asp Ile Ala His His His His His His
                725
```

<210> SEQ ID NO 95
<211> LENGTH: 969
<212> TYPE: DNA
<213> ORGANISM: Artificial Sequence
<220> FEATURE:
<223> OTHER INFORMATION: Description of Artificial Sequence:mAB #8860
     scFv-leucine zipper fusion protein (miniantibody vector construct
     p8860-Zip#1.2)

<400> SEQUENCE: 95
atgaaatacc tattgcctac ggcagccgct ggattgttat tactcgcggc ccagccggcc      60
atggcggagg ttcagcttca gcagtctgga cctgagctgg tgaagcccgg ggcctcagtg     120

```
aagatttcct gcaaagcttc tggctacgca ttcagtagct cttggatgaa ctgggtgaag      180
cagaggcctg gacagggtct tgagtggatt ggacggattt atcctggaaa tggagatact      240
aactacaatg gaagttcaa gggcaaggcc acactgactg cagacaaatc ctccagcaca       300
gcctacatgc agctcagcag cctgacctct gtggactctg cggtctattt ctgtgcagat      360
ggtaacgtat attactatgc tatggactac tggggtcaag gaacctcagt caccgtctcc      420
tcaggtggag gcggttcagg tgggcgcgcc tctggcggtg gcggatcgca aattgttctc      480
acccagtctc ctgcttcctt agctgtatct ctggggcaga gggccaccat ctcatgcagg      540
gccagcaaaa gtgtcagtac atctggctat agttatatgc actggtacca acagaaacca      600
ggacagccac ccaaactcct catctatctt gcatccaacc tagaatctgg ggtccctgcc      660
aggttcagtg gcagtgggtc tgggacagac ttcaccctca acatccatcc tgtggaggag      720
gaggatgctg caacctatta ctgtcagcac agtagggagc ttcctcggac gttcggtgga      780
ggcaccaagc tggaaatcaa acgggcggcc gcaccgaagc cttccactcc gcccgggtct      840
tcccgtatga acagctgga agacaaagta gaggagctcc ttagcaagaa ctaccatcta       900
gaaaacgagg tagctcgtct gaaaaagctt gttggtgaac gtggtggtca ccatcaccat      960
caccattaa                                                              969

<210> SEQ ID NO 96
<211> LENGTH: 322
<212> TYPE: PRT
<213> ORGANISM: Artificial Sequence
<220> FEATURE:
<223> OTHER INFORMATION: Description of Artificial Sequence:mAB #8860
      scFv-leucine zipper fusion protein (miniantibody vector construct
      p8860-Zip#1.2)

<400> SEQUENCE: 96

Met Lys Tyr Leu Leu Pro Thr Ala Ala Gly Leu Leu Leu Leu Ala
 1               5                  10                  15

Ala Gln Pro Ala Met Ala Glu Val Gln Leu Gln Gln Ser Gly Pro Glu
                20                  25                  30

Leu Val Lys Pro Gly Ala Ser Val Lys Ile Ser Cys Lys Ala Ser Gly
            35                  40                  45

Tyr Ala Phe Ser Ser Ser Trp Met Asn Trp Val Lys Gln Arg Pro Gly
        50                  55                  60

Gln Gly Leu Glu Trp Ile Gly Arg Ile Tyr Pro Gly Asn Gly Asp Thr
65                  70                  75                  80

Asn Tyr Asn Gly Lys Phe Lys Gly Lys Ala Thr Leu Thr Ala Asp Lys
                85                  90                  95

Ser Ser Ser Thr Ala Tyr Met Gln Leu Ser Ser Leu Thr Ser Val Asp
            100                 105                 110

Ser Ala Val Tyr Phe Cys Ala Asp Gly Asn Val Tyr Tyr Ala Met
        115                 120                 125

Asp Tyr Trp Gly Gln Gly Thr Ser Val Thr Val Ser Ser Gly Gly Gly
    130                 135                 140

Gly Ser Gly Gly Arg Ala Ser Gly Gly Gly Ser Gln Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Lys Ser Val Ser Thr Ser Gly Tyr Ser Tyr
            180                 185                 190

Met His Trp Tyr Gln Gln Lys Pro Gly Gln Pro Pro Lys Leu Leu Ile
```

```
                195            200              205
Tyr Leu Ala Ser Asn Leu Glu Ser Gly Val Pro Ala Arg Phe Ser Gly
    210                 215                 220

Ser Gly Ser Gly Thr Asp Phe Thr Leu Asn Ile His Pro Val Glu Glu
225                 230                 235                 240

Glu Asp Ala Ala Thr Tyr Tyr Cys Gln His Ser Arg Glu Leu Pro Arg
                245                 250                 255

Thr Phe Gly Gly Gly Thr Lys Leu Glu Ile Lys Arg Ala Ala Ala Pro
                260                 265                 270

Lys Pro Ser Thr Pro Pro Gly Ser Ser Arg Met Lys Gln Leu Glu Asp
    275                 280                 285

Lys Val Glu Glu Leu Leu Ser Lys Asn Tyr His Leu Glu Asn Glu Val
    290                 295                 300

Ala Arg Leu Lys Lys Leu Val Gly Glu Arg Gly Gly His His His His
305                 310                 315                 320

His His
```

<210> SEQ ID NO 97
<211> LENGTH: 270
<212> TYPE: DNA
<213> ORGANISM: Artificial Sequence
<220> FEATURE:
<223> OTHER INFORMATION: Description of Artificial Sequence:part of
      plasmid pMycHis6 differing from vector pCOCK

<400> SEQUENCE: 97

```
caggaaacag ctatgaccat gattacgcca agcttccatg aaaattctat ttcaaggaga     60
cagtcataat gaaatacctà ttgcctacgg cagccgctgg attgttatta ctcgcggccc    120
agccggccat ggcccaggtg cagctgcagg cgcgcctgca ggtcgacctc gagatcaaac    180
gggcggccgc agaacaaaaa ctcatctcag aagaggatct gaatggggcg gcacatcacc    240
atcaccatca ctaataagaa ttcactggcc                                     270
```

<210> SEQ ID NO 98
<211> LENGTH: 61
<212> TYPE: PRT
<213> ORGANISM: Artificial Sequence
<220> FEATURE:
<223> OTHER INFORMATION: Description of Artificial Sequence:part of
      plasmid pMycHis6 differing from vector pCOCK

<400> SEQUENCE: 98

```
Met Lys Tyr Leu Leu Pro Thr Ala Ala Ala Gly Leu Leu Leu Leu Ala
  1               5                  10                  15

Ala Gln Pro Ala Met Ala Gln Val Gln Leu Gln Ala Arg Leu Gln Val
                 20                  25                  30

Asp Leu Glu Ile Lys Arg Ala Ala Ala Glu Gln Lys Leu Ile Ser Glu
         35                  40                  45

Glu Asp Leu Asn Gly Ala Ala His His His His His His
     50                  55                  60
```

<210> SEQ ID NO 99
<211> LENGTH: 888
<212> TYPE: DNA
<213> ORGANISM: Artificial Sequence
<220> FEATURE:
<223> OTHER INFORMATION: Description of Artificial Sequence:198AB2 scFv
      linked to c-myc-tag and His6 tag (ORF of expression vector
      pMycHis6-198AB2#102)
<220> FEATURE:

<221> NAME/KEY: modified_base
<222> LOCATION: (228)
<223> OTHER INFORMATION: n = g, a, c or t

<400> SEQUENCE: 99

```
atgaaatacc tattgcctac ggcagccgct ggattgttat tactcgcggc ccagccggcc      60
atggccgagg tgaagctggt ggagtctggg ggaggcttag tgaagcctgg agggtccctg     120
aaactctcct gtgcagcctc tggattcact ttcagtagct ataccatgtc ttgggttcgc     180
cagactccgg agaagaggct ggagtgggtc gcaaccatta gtagtggngg tagttccacc     240
tactatccag acagtgtgaa gggccgattc accatctcca gagacaatgc caagaacacc     300
ctgtacctgc aaatgagcag tctgaggtct gaggacacag ccatgtatta ctgtacaaga     360
gagggggtg tttcaccgt caactggtac ttcgatgtct ggggcgcagg aacctcagtc     420
accgtctcct caggtggagg cggttcaggt gggcgcgcct ctggcggtgg cggatcggac     480
attgtgctga cacagtctcc agcttctttg gctgtgtctc tagggcagag ggccaccata     540
tcctgcagag ccagtgaaag tgttgatagt tatggctata attttatgca ctggtatcag     600
cagataccag acagccacc caaactcctc atctatcgtg catccaacct agagtctggg     660
atccctgcca ggttcagtgg cagtgggtct aggacagact tcaccctcac cattaatcct     720
gtggaggctg atgatgttgc aacctattac tgtcagcaaa gtaatgagga tccgctcacg     780
ttcggtactg ggaccagact ggaaataaaa cgggcggccg cagaacaaaa actcatctca     840
gaagaggatc tgaatggggc ggcacatcac catcaccatc actaataa                  888
```

<210> SEQ ID NO 100
<211> LENGTH: 294
<212> TYPE: PRT
<213> ORGANISM: Artificial Sequence
<220> FEATURE:
<223> OTHER INFORMATION: Description of Artificial Sequence:198AB2 scFv linked to c-myc-tag and His6 tag (ORF of expression vector pMycHis6-198AB2#102)

<400> SEQUENCE: 100

```
Met Lys Tyr Leu Leu Pro Thr Ala Ala Ala Gly Leu Leu Leu Leu Ala
  1               5                  10                  15

Ala Gln Pro Ala Met Ala Glu Val Lys Leu Val Glu Ser Gly Gly Gly
                 20                  25                  30

Leu Val Lys Pro Gly Gly Ser Leu Lys Leu Ser Cys Ala Ala Ser Gly
             35                  40                  45

Phe Thr Phe Ser Ser Tyr Thr Met Ser Trp Val Arg Gln Thr Pro Glu
         50                  55                  60

Lys Arg Leu Glu Trp Val Ala Thr Ile Ser Ser Gly Gly Ser Ser Thr
 65                  70                  75                  80

Tyr Tyr Pro Asp Ser Val Lys Gly Arg Phe Thr Ile Ser Arg Asp Asn
                 85                  90                  95

Ala Lys Asn Thr Leu Tyr Leu Gln Met Ser Ser Leu Arg Ser Glu Asp
            100                 105                 110

Thr Ala Met Tyr Tyr Cys Thr Arg Glu Gly Gly Phe Thr Val Asn
            115                 120                 125

Trp Tyr Phe Asp Val Trp Gly Ala Gly Thr Ser Val Thr Val Ser Ser
        130                 135                 140

Gly Gly Gly Gly Ser Gly Gly Arg Ala Ser Gly Gly Gly Gly Ser Asp
145                 150                 155                 160

Ile Val Leu Thr Gln Ser Pro Ala Ser Leu Ala Val Ser Leu Gly Gln
```

```
                    165                 170                 175
Arg Ala Thr Ile Ser Cys Arg Ala Ser Glu Ser Val Asp Ser Tyr Gly
            180                 185                 190

Tyr Asn Phe Met His Trp Tyr Gln Gln Ile Pro Gly Gln Pro Pro Lys
        195                 200                 205

Leu Leu Ile Tyr Arg Ala Ser Asn Leu Glu Ser Gly Ile Pro Ala Arg
        210                 215                 220

Phe Ser Gly Ser Gly Ser Arg Thr Asp Phe Thr Leu Thr Ile Asn Pro
225                 230                 235                 240

Val Glu Ala Asp Asp Val Ala Thr Tyr Tyr Cys Gln Gln Ser Asn Glu
                245                 250                 255

Asp Pro Leu Thr Phe Gly Thr Gly Thr Arg Leu Glu Ile Lys Arg Ala
            260                 265                 270

Ala Ala Glu Gln Lys Leu Ile Ser Glu Glu Asp Leu Asn Gly Ala Ala
            275                 280                 285

His His His His His His
        290

<210> SEQ ID NO 101
<211> LENGTH: 876
<212> TYPE: DNA
<213> ORGANISM: Artificial Sequence
<220> FEATURE:
<223> OTHER INFORMATION: Description of Artificial Sequence:mAB #8860
      scFv linked to c-myc-tag and His6-tag designated 8860-M/H#4c
      (plasmid vector p8860-M/H#4c)

<400> SEQUENCE: 101
atgaaatacc tattgcctac ggcagccgct ggattgttat tactcgcggc ccagccggcc      60
atggccgagg ttcagcttca gcagtctgga cctgagctgg tgaagcccgg ggcctcagtg     120
aagatttcct gcaaagcttc tggctacgca ttcagtagct cttggatgaa ctgggtgaag     180
cagaggcctg gacagggtct tgagtggatt ggacggattt atcctggaaa tggagatact     240
aactacaatg gaagttcaa gggcaaggcc acactgactg cagacaaatc ctccagcaca     300
gcctacatgc agctcagcag cctgacctct gtggactctg cggtctattt ctgtgcagat     360
ggtaacgtat attactatgc tatggactac tggggtcaag gaacctcagt caccgtctcc     420
tcaggtggag gcggttcagg tgggcgcgcc tctggcggtg gcggatcgca aattgttctc     480
acccagtctc ctgcttcctt agctgtatct ctggggcaga gggccaccat ctcatgcagg     540
gccagcaaaa gtgtcagtac atctggctat agttatatgc actggtacca acagaaacca     600
ggacagccac ccaaactcct catctatctt gcatccaacc tagaatctgg ggtccctgcc     660
aggttcagtg gcagtgggtc tgggacagac ttcaccctca acatccatcc tgtggaggag     720
gaggatgctg caacctatta ctgtcagcac agtagggagc ttcctcggac gttcggtgga     780
ggcaccaagc tggaaatcaa acgggcggcc gcagaacaaa aactcatctc agaagaggat     840
ctgaatgggg cggcacatca ccatcaccat cactaa                               876

<210> SEQ ID NO 102
<211> LENGTH: 291
<212> TYPE: PRT
<213> ORGANISM: Artificial Sequence
<220> FEATURE:
<223> OTHER INFORMATION: Description of Artificial Sequence:mAB #8860
      scFv linked to c-myc-tag and His6-tag designated 8860-M/H#4c
      (plasmid vector p8860-M/H#4c)

<400> SEQUENCE: 102
```

```
Met Lys Tyr Leu Leu Pro Thr Ala Ala Gly Leu Leu Leu Ala
 1               5                  10                  15

Ala Gln Pro Ala Met Ala Glu Val Gln Leu Gln Gln Ser Gly Pro Glu
            20                  25                  30

Leu Val Lys Pro Gly Ala Ser Val Lys Ile Ser Cys Lys Ala Ser Gly
        35                  40                  45

Tyr Ala Phe Ser Ser Ser Trp Met Asn Trp Val Lys Gln Arg Pro Gly
    50                  55                  60

Gln Gly Leu Glu Trp Ile Gly Arg Ile Tyr Pro Gly Asn Gly Asp Thr
65                  70                  75                  80

Asn Tyr Asn Gly Lys Phe Lys Gly Lys Ala Thr Leu Thr Ala Asp Lys
                85                  90                  95

Ser Ser Ser Thr Ala Tyr Met Gln Leu Ser Ser Leu Thr Ser Val Asp
            100                 105                 110

Ser Ala Val Tyr Phe Cys Ala Asp Gly Asn Val Tyr Tyr Ala Met
        115                 120                 125

Asp Tyr Trp Gly Gln Gly Thr Ser Val Thr Val Ser Ser Gly Gly Gly
130                 135                 140

Gly Ser Gly Gly Arg Ala Ser Gly Gly Gly Ser Gln Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Lys Ser Val Ser Thr Ser Gly Tyr Ser Tyr
            180                 185                 190

Met His Trp Tyr Gln Gln Lys Pro Gly Gln Pro Pro Lys Leu Leu Ile
    195                 200                 205

Tyr Leu Ala Ser Asn Leu Glu Ser Gly Val Pro Ala Arg Phe Ser Gly
    210                 215                 220

Ser Gly Ser Gly Thr Asp Phe Thr Leu Asn Ile His Pro Val Glu Glu
225                 230                 235                 240

Glu Asp Ala Ala Thr Tyr Tyr Cys Gln His Ser Arg Glu Leu Pro Arg
                245                 250                 255

Thr Phe Gly Gly Gly Thr Lys Leu Glu Ile Lys Arg Ala Ala Ala Glu
            260                 265                 270

Gln Lys Leu Ile Ser Glu Glu Asp Leu Asn Gly Ala Ala His His
        275                 280                 285

His His His
    290

<210> SEQ ID NO 103
<211> LENGTH: 74
<212> TYPE: DNA
<213> ORGANISM: Artificial Sequence
<220> FEATURE:
<223> OTHER INFORMATION: Description of Artificial Sequence:annealed
      oligonucleotide

<400> SEQUENCE: 103
ggccgcagaa caaaaactca tctcagaaga ggatctgaat ggggcggcac atcaccatca     60
ccatcactaa taag                                                       74

<210> SEQ ID NO 104
<211> LENGTH: 69
<212> TYPE: DNA
<213> ORGANISM: Artificial Sequence
<220> FEATURE:
```

```
<223> OTHER INFORMATION: Description of Artificial Sequence:annealed
      oligonucleotide

<400> SEQUENCE: 104
ttattagtga tggtgatggt gatgtgccgc cccattcaga tcctcttctg agatgagttt      60
ttgttctgc                                                              69

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence:CDR3 peptide
<220> FEATURE:
<221> NAME/KEY: MOD_RES
<222> LOCATION: (1)..(16)
<223> OTHER INFORMATION: Xaa = any amino acid

<400> SEQUENCE: 105

Cys Xaa Xaa Tyr Gly Asn Ser Pro Lys Gly Phe Ala Tyr Xaa Xaa Cys
 1               5                  10                  15

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence:CDR3 peptide

<400> SEQUENCE: 106

Phe Arg Asn Arg Gly Met Thr Ala Leu Leu Lys Val Ser Ser Cys Asp
 1               5                  10                  15

<210> SEQ ID NO 107
<211> LENGTH: 30
<212> TYPE: PRT
<213> ORGANISM: Artificial Sequence
<220> FEATURE:
<223> OTHER INFORMATION: Description of Artificial Sequence:portion of
      plasmid pMycHis6 with pelB-leader, polylinker and c-myc tag

<400> SEQUENCE: 107

Leu Ala Ala Gln Pro Ala Met Ala Gln Val Gln Leu Gln Ala Arg Leu
 1               5                  10                  15

Gln Val Asp Leu Glu Ile Lys Arg Ala Ala Ala Glu Gln Lys
            20                  25                  30

<210> SEQ ID NO 108
<211> LENGTH: 90
<212> TYPE: DNA
<213> ORGANISM: Artificial Sequence
<220> FEATURE:
<223> OTHER INFORMATION: Description of Artificial Sequence:portion of
      plasmid pMycHis6 with pelB-leader, polylinker and c-myc tag

<400> SEQUENCE: 108
ctcgcggccc agccggccat ggcccaggtg cagctgcagg cgcgcctgca ggtcgacctc      60
gagatcaaac gggcggccgc agaacaaaaa                                       90

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence:c-myc-tag
```

```
<400> SEQUENCE: 109

Glu Gln Lys Leu Ile Ser Glu Glu Asp Leu Asn Gly
 1               5                  10

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence:His6-tag

<400> SEQUENCE: 110

His His His His His His
 1               5

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence:flexible
      linker

<400> SEQUENCE: 111

Gly Gly Gly Gly Ser Gly Gly Arg Ala Ser Gly Gly Gly Gly Ser
 1               5                  10                  15

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence:A1 peptide
      core sequence

<400> SEQUENCE: 112

Glu Gly Gly Gly Tyr Tyr Val Asn Trp Tyr Phe Asp
 1               5                  10
```